US008466102B2

(12) United States Patent
Krieger et al.

(10) Patent No.: US 8,466,102 B2
(45) Date of Patent: *Jun. 18, 2013

(54) ANTIMICROBIAL CATIONIC PEPTIDES AND FORMULATIONS THEREOF

(75) Inventors: Timothy J. Krieger, Lowell, MA (US); Patricia J. McNicol, Vancouver (CA)

(73) Assignee: Carrus Capital Corporation, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/421,018

(22) Filed: Mar. 15, 2012

(65) Prior Publication Data

US 2012/0202735 A1    Aug. 9, 2012

Related U.S. Application Data

(63) Continuation of application No. 10/865,687, filed on Jun. 10, 2004, now Pat. No. 8,138,144, which is a continuation of application No. 10/225,087, filed on Aug. 20, 2002, now Pat. No. 6,835,536.

(60) Provisional application No. 60/314,232, filed on Aug. 21, 2001.

(51) Int. Cl.
*A61K 38/04* (2006.01)

(52) U.S. Cl.
USPC .......................................................... 514/2

(58) Field of Classification Search
None
See application file for complete search history.

(56) References Cited

U.S. PATENT DOCUMENTS

| | | | |
|---|---|---|---|
| 4,510,132 A | 4/1985 | Vaara | |
| 4,816,449 A | 3/1989 | Hahn | |
| 5,324,716 A | 6/1994 | Selsted et al. | |
| 5,359,030 A | 10/1994 | Ekwuribe | |
| 5,409,898 A | 4/1995 | Darveau et al. | |
| 5,436,222 A | 7/1995 | Kuna et al. | |
| 5,438,040 A | 8/1995 | Ekwuribe | |
| 5,459,235 A | 10/1995 | Selsted et al. | |
| 5,505,949 A | 4/1996 | Benitez | |
| 5,523,288 A | 6/1996 | Cohen et al. | |
| 5,547,939 A | 8/1996 | Selsted | |
| 5,578,572 A | 11/1996 | Horwitz et al. | |
| 5,593,866 A | 1/1997 | Hancock et al. | |
| 5,679,665 A | 10/1997 | Bergamini et al. | |
| 5,776,892 A | 7/1998 | Counts et al. | |
| 5,821,224 A | 10/1998 | Selsted et al. | |
| 5,834,430 A | 11/1998 | Porro et al. | |
| 6,040,435 A | 3/2000 | Hancock et al. | |
| 6,057,291 A | 5/2000 | Hancock et al. | |
| 6,177,471 B1 | 1/2001 | Menander et al. | |
| 6,180,604 B1 | 1/2001 | Fraser et al. | |
| 6,190,691 B1 | 2/2001 | Mak | |
| 6,191,254 B1 | 2/2001 | Falla et al. | |
| 6,248,343 B1 | 6/2001 | Jampani et al. | |
| RE37,263 E | 7/2001 | Kross et al. | |
| 6,303,575 B1 | 10/2001 | Selsted | |
| 6,482,799 B1 | 11/2002 | Tuse et al. | |
| 6,503,881 B2 | 1/2003 | Krieger et al. | |
| 6,538,106 B1 | 3/2003 | Fraser et al. | |
| 6,835,536 B2 | 12/2004 | Krieger et al. | |
| 8,138,144 B2 | 3/2012 | Krieger et al. | |

FOREIGN PATENT DOCUMENTS

| | | |
|---|---|---|
| EP | 0590070 B1 | 4/1994 |
| EP | 0930065 B1 | 9/2004 |
| WO | 91/12815 | 9/1991 |
| WO | 92/15286 | 9/1992 |
| WO | 92/22308 | 12/1992 |
| WO | 93/24513 | 12/1993 |
| WO | 94/12150 | 6/1994 |
| WO | 95/22338 | 8/1995 |
| WO | 96/38473 | 12/1996 |
| WO | 97/04796 | 2/1997 |
| WO | 97/08199 | 3/1997 |
| WO | 97/12601 | 4/1997 |
| WO | 97/31942 | 9/1997 |
| WO | 98/07745 | 2/1998 |
| WO | 98/07745 A2 | 2/1998 |
| WO | 98/40401 | 9/1998 |
| WO | 98/45319 | 10/1998 |
| WO | 99/43357 | 9/1999 |
| WO | 99/58141 | 11/1999 |
| WO | 99/65506 | 12/1999 |
| WO | 99/65510 | 12/1999 |
| WO | 00/00214 | 1/2000 |
| WO | 00/47183 | 8/2000 |
| WO | 00/71175 | 11/2000 |
| WO | 00/72872 | 12/2000 |
| WO | 03/015809 | 2/2003 |

OTHER PUBLICATIONS

Boman, H.G., "Innate Immunity and the Normal Microflora," Immunological Reviews, vol. 173, 2000, pp. 5-16.
Braegger, Acta Paediactrica Supplement, vol. 395, 1994, 18021.
Buku, A., "Mast Cell Degranulating (MCD) Peptide: a Prototypic Peptide in Allergy and Inflammation," Peptides, vol. 20, 1999, pp. 415-420.
Burkhart, C.G. et al., "Acne: a Review of Immunologic and Microbiologic Factors," Postgraduate Medical Journal, vol. 75, Issue 884, Jun. 1999, pp. 328-331.
Chaly, Y.V. et al., "Human Neutrophil α-Defensin Modulates Cytokine Production in Human Monocytes and Adhesion Molecule Expression in Endothelial Cells," European Cytokine Netwok, vol. 11, Issue 2, Jun. 2000, pp. 257-266.
Cole, A.M. et al., "Human Antimicrobial Peptides: Analysis and Application," BioTechniques, vol. 29, Issue 4, Oct. 2000, pp. 822-831.

(Continued)

*Primary Examiner* — Brian J Gangle
(74) *Attorney, Agent, or Firm* — Frommer Lawrence & Haug LLP; Bruce E. Black

(57) ABSTRACT

Compositions and methods for making and using therapeutic formulations of antimicrobial cationic peptides are provided. The antimicrobial cationic peptide formulations may be used, for example, in the treatment of microorganism-caused infections, which infections may be systemic, such as a septicemia, or may be localized, such as in acne or an implanted or indwelling medical device.

39 Claims, 2 Drawing Sheets

OTHER PUBLICATIONS

Creighton T.E., In Proteins: Structures and Molecular Properties, 1984, pp. 314-315.
Creighton T.E., In Proteins: Structures and Molecular Properties, 1984, pp. 184-186.
Cruse, J.M. et al., Illustrated Dictionary of Immunology, Second Edition, CRC Press, 2003, pp. 335-336.
Cutuli, M. et al., "Antimicrobial Effects of α-MSH Peptides," Journal of Leukocyte Biology, vol. 67, Issue 2, Feb. 2000, pp. 233-239.
Dahlberg, P.S. et al., "A Novel Endotoxin Antagonist Attenuates Tumor Necrosis Factor-α Secretion," Journal of Surgical Research, vol. 63, 1996, pp. 44-48.
Dankesreiter, S. et al., "Synthetic: Endotoxin-Binding Peptides Block Endotoxin-Triggered TNF-α Production by Macrophages In Vitro and In Vivo and Prevent Endotoxin-Mediated Toxic Shock," Journal of Immunology, vol. 164, 2000, pp. 4804-4811.
Dorland's Online Medical Dictionary, accessed Jul. 21, 2006, 1 page.
Ek, L. et al., "Tachykinins and Calcitonin Gene-Related Peptide in Oxazolone-Induced Allergic Contact Dermatitis in Mice," Journal of Investigative Dermatology, vol. 94, Issue 6, Jun. 1990, pp. 761-763.
Epand, R.M. et al., "Diversity of Antimicrobial Peptides and Their Mechanisms of Action," Biochemica et Biophysics Acta, vol. 1462, 1999, pp. 11-28.
Fox, J.L., "No Winners Against AIDS," Biotechnology, vol. 12, 1994, 1 page.
Fox, J.G. et al., "A Novel Urease-Negative Helicobacter Species Associated with Colitis and Typhlitis in IL-10-Deficient Mice," Infection and Immunity, vol. 67, Issue 4, Apr. 1999, pp. 1757-1762.
Goebeler, M. et al., "Substance P and Calcitonin Gene-Related Peptide Modulate Leukocyte Infiltration to Mouse Skin During Allergic Contact Dermatitis," Archives of Dermatological Research vol. 286, 1994, pp. 341-346.
Gu, X.X. et al., "Synthesis and Characterization of Lipooligosaccharide-Based Conjugates as Vaccine Candidates for Moraxella (Branharnella) catarrhalis," Infection and Immunity, vol. 66, Issue 5, May 1998, pp. 1891-1897.
Guenther L.C. et al., "A Comparison of Tazarotene 0.1% Gel Once Daily plus Mometasone Furoate 0.1% Cream Once Daily Versus Calcipotriene, 0.005% Ointment Twice Daily in the Treatment of Plaque Psoriasis," Clinical Therapeutics, vol. 22, Issue 10, Oct. 2000, pp. 1225-1238.
Gutwald, J. et al., "Neuropeptides Enhance Irritant and Allergic Contact Dermatitis," Journal of Investigative Dermatology, vol. 96, Issue 5, May 1991, pp. 695-698.
Hancock, R.E. et al., "The Role of Cationic Antimicrobial Peptides in Innate Host Defenses," Trends in Microbiology, vol. 8, Issue 9, Sep. 2000, pp. 402-410.
Hancock, R.E. et al., "Cationic Peptides: a New Source of Antibiotics," Trends in Microbiology, vol. 16, Issue 2, Feb. 1998, pp. 82-88.
Hancock, R.E. et al., "The Role of Antimicrobial Peptides in Animal Defenses," Proceedings of the national Academy of Sciences of the United States of America, vol. 97, Issue 16, Aug. 1, 2000, pp. 8856-8861.
Haworth, D. et al., "Anti-Inflammatory Activity of C(ILDV-NH(CH2)5CO), a Novel, Selective Cyclic Peptide Inhibitor of VLA-4-Mediated Cell Adhesion," British Journal of Pharmacology, vol. 126, Issue 8, Apr. 1999, pp. 1751-1760.
Hiltz, M.E. et al., "Alpha-MSH Peptides Inhibit Acute Inflammation and Contact Sensitivity," Peptides, vol. 11, Issue 5, Sep.-Oct. 1990, pp. 979-982.
Høgåsen, A.K. et al., "Polymyxin B Stimulates Production of Complement Components and Cytokines in Human Monocytes," Antimicrobial Agents and Chemotherapy, vol. 39, Issue 2, Feb. 1995, pp. 529-532.
Kyd, J. et al., "Investigation of Mucosal Immunisation in Pulmonary Clearance of Moraxella (Branhamella) catarrhalis," Vaccine, vol. 18, 2000, pp. 398-406.
Lipton, J.M. et al., "Central Administration of the Peptide α-MSH Inhibits Inflammation in the Skin," Peptides, vol. 12, Issue 4, Jul.-Aug. 1991, pp. 795-798.
Lloret, S. et al., "Effects of an Anti-Inflammatory Peptide (Antiflammin 2) on Cell Influx, Eicosanoid Biosynthesis and Oedema Formation by Arachidonic Acid and Tetradecarioyl Phorbol Dermal Application," Biochemical Pharmacology, vol. 50, Issue 3, 1995, p. 347-353.
Lloret, S. et al., "In Vitro and in Vivo Effects of the Anti-Inflammatory Peptides, Antiflammins," Biochemical Pharmacology, vol. 44, Issue 7, 1992, pp. 1437-1441.
Luger, T.A. et al., "Cutaneous Immunomodulation and Coordination of Skin Stress Responses by α-Melanocyte-Stimulating Hormone," Annals of the New York Academy of Sciences, vol. 840, May 1998, pp. 381-394.
Masera, R.G. et al., "Corticostatins/Defensins Inhibit In Vitro NK Activity and Cytokine Production by Human Peripheral Blood Mononuclear Cells," Regulatory Peptides, vol. 62, Issue 1, Apr. 9, 1996, pp. 13-21.
Nosoh, Y. et al., In Protein Stability and Stabilization through Protein Engineering, 1991, Chapter 7, p. 197, second paragraph.
Odeh, M., "The Role of Tumor Necrosis Factor-Alpha in the Pathogenesis of complicated Falciparum Malaria," Cytokine, vol. 14, Issue 1, Apr. 7, 2001, pp. 11-18.
Olsen, T.G., "Therapy of Acne," Medical Clinics of North America, vol. 66. Issue 4, Jul. 1982, pp. 851-871.
Paulus, H.E. et al., "Nonsteroid Anti-Inflammatory Agents," Annual Review of Pharmacology and Toxicology, vol. 13, 1973, pp. 107-125.
Rheins, L.A. et al., "Alpha-Melanocyte Stimulating Hormone Modulates Contact Hypersensitivity Responsiveness in C57/BL6 Mice," Journal of Investigative Dermatology vol. 93, Issue 4, Oct. 1989, pp. 511-517.
Roszowski, W. et al., "Suppression of Cell-Mediated Immune Reactivity by Peptides Cleaved from Human Fibrinogen," Upsala Journal of Medical Sciences, vol. 90, Issue 3, 1985, pp. 279-291.
Samukawa, T. et al., "Immune Response to Surface Protein A of Streptococcus pneumoniae and to High-Molecular-Weight Outer Membrane Protein A of Moraxella catarrhalis in Children with Acute Otitis Media," The Journal of Infectious Diseases, vol. 181, Issue 5, May 2000, pp. 1842-1845.
Sartor, R.B., "Current Concepts of the Etiology and Pathogenesis of Ulcerative Colitis and Crohn's Disease," Gastroenterology Clinic of North America, vol. 24, No. 3, Sep. 1995, pp. 475-507.
Scott, M.G. et al., "Biological Properties of Structurally Related α-Helical Cationic Antimicrobial Peptides," Infection and Immunity, vol. 67, Issue 4, Apr. 1999, pp. 2005-2009.
Scott, M.G. et al., "Cutting Edge: Cationic Antimicrobial Peptides Block the Binding of Lipopolysaccharide (LPS) to LPS Binding Protein," Journal of Immunology, vol. 164, Issue 2, Jan. 15, 2000, pp. 549-553.
Scott, M.G. et al., "An α-Helical Cationic Antimicrobial Peptide Selectively Modulates Macrophage Responses to Lipopolysaccharide and Directly Alters Macrophage Gene Expression," Journal of Immunology vol. 165, 2000, pp. 3358-3365.
Shi, J. et al., "PR-39, a Proline-Rich Antibacterial Peptide that Inhibits Phagocyte NADPH Oxidase Activity by Binding to SRC Homology 3 Domains of p47Phox," Proceedings of the National Academy of Sciences, vol. 93, Jun. 1996, pp. 6014-6018.
Shkenderov, S., "New Pharmacobiochemical Data on the Anti-Inflammatory Effect of Bee Venom," in Animal, Plant, and Microbial Toxins, vol. 2, 1976, pp. 319-336.
Sigusch, B. et al., "Early-Onset and Adult Periodontitis Associated with Abnormal Cytokine Production by Activated T Lymphocytes," Journal of Periodontology, vol. 69, Issue 10, Oct. 1998, pp. 1998-1104.
Somerfeld, S.D. et al., "Bee Venom Melittin Blocks Neutrophil O2-Production," Inflammation, vol. 10, Issue 2, 1986, pp. 175-182.
Van Wetering, S. et al., "Defensins: Key Players or Bystanders in Infection, Injury, and Repair in the Lung?" Journal of Allergy and Clinical Immunology, vol. 104, Issue 6, Dec. 1999, pp. 1131-1138.
Van Wetering, S. et al., "Effect of Defensins on Interleukin-8 Synthesis in Airway Epithelial Cells," American Journal of Physiology, vol. 272, Issue 5, Part 1, May 1997, pp. L888-L896.
Vowels, B.R. et al., "Induction of Proinflammatory Cytokines by Soluble Factor of Propionibacterium acnes: Implications for Chronic Inflammatory Acne," Infection and Immunity, vol. 63, Issue 8, Aug. 1995, pp. 3158-3165.
Webster's II New Riverside University Dictionary, The Riverside Publishing Company, 1984.

Wei, E.T. et al., "Anti-Inflammatory Peptide Agonists," Annual Review of Pharmacology and Toxicology, vol. 33, 1993, pp. 91-108.
Wright, C.G. et al., "An Animal Model for External Ear Canal Inflammation," The Laryngoscope, vol. 110, Issue 7, Jul. 2000, pp. 1112-1118.
Young et al., "Tachyphylaxis in 12-0-Tetradecanoylphorbol Acetate- and Arachidonic Acid-Induced Ear Edema," Journal of Investigative Dermatology, vol. 80, Issue 1, Jan. 1983, pp. 48-52.
Zunic, M. et al., "MDP(Lysyl)GDP, a Nontoxic Muramyl Dipeptide Derivative, Inhibits Cytokine Production by Activated Macrophages and Protects Mice from Phorbol Ester- and Oxazolone-Induced Inflammation," Journal of Investigative Dermatology, vol. 111, Issue 1, Jul. 1998, pp. 77-82.
Japanese Office Action mailed Oct. 29, 2010 for corresponding Japanese Patent Application No. 2003-520767 filed on Aug. 21, 2002.
European Communication Pursuant to Article 96(2) EPC dated Nov. 6, 2006 for corresponding European Patent Application No. 02759416.7.
European Communication Pursuant to Article 94(3) EPC dated Mar. 13, 2008 for corresponding European Patent Application No. 02759416.7.
Summons to Attend Oral Proceedings Pursuant to Rule 115(1) EPC dated Feb. 26, 2010 for corresponding European Patent Application No. 02759416.7.
U.S. Office Action mailed Aug. 19, 2011 for co-pending U.S. Appl. No. 10/229,368.
U.S. Advisory Action mailed Nov. 10, 2010 for co-pending U.S. Appl. No. 10/229,368.
U.S. Final Office Action mailed Apr. 28, 2010 for co-pending U.S. Appl. No. 10/229,368.
U.S. Office Action mailed Jun. 23, 2009 for co-pending U.S. Appl. No. 10/229,368.
U.S. Office Action mailed Sep. 29, 2008 for co-pending U.S. Appl. No. 10/229,368.
U.S. Final Office Action mailed Jun. 25, 2008 for co-pending U.S. Appl. No. 10/229,368.
U.S. Final Office Action mailed Jan. 2, 2008 for co-pending U.S. Appl. No. 10/229,368.
U.S. Office Action mailed Apr. 9, 2007 for co-pending U.S. Appl. No. 10/229,368.
U.S. Office Action mailed Aug. 1, 2006 for co-pending U.S. Appl. No. 10/229,368.
U.S. Office Action mailed Nov. 7, 2005 for co-pending U.S. Appl. No. 10/229,368.
U.S. Advisory Action mailed Jul. 5, 2005 for co-pending U.S. Appl. No. 10/229,368.
U.S. Final Office Action mailed Jan. 21, 2005 for co-pending U.S. Appl. No. 10/229,368.
U.S. Office Action mailed Jun. 25, 2004 for co-pending U.S. Appl. No. 10/229,368.
U.S. Office Action (Restriction Requirement) mailed Mar. 9, 2004 for co-pending U.S. Appl. No. 10/229,368.
U.S. Notice of Allowance and Fees Due mailed Mar. 23, 2004 for co-pending U.S. Appl. No. 10/225,087.
U.S. Office Action mailed Oct. 3, 2003 for co-pending U.S. Appl. No. 10/225,087.
Remington, "Remington: The Science and Practice of Pharmacy," vol. II, 1995, pp. 1380-1416 and 1495-1523.
Swarbrick et al., "Encyclopedia of Pharmaceutical Technology," vol. 19, Suppl, 2, 1998, pp. 137-172.
Hancock, R. E., "Cationic Antimicrobial Peptides: Towards Clinical Applications," Expert Opinion on Investigational Drugs, vol. 9, No. 8, Aug. 2000, pp. 1723-1729.
Hancock, R. E., "Peptide Antibiotics," The Lancet, vol. 349, No. 9049, Feb. 8, 1997, pp. 418-422.
Canadian Office Action mailed Apr. 30, 2009 for corresponding Canadian Application No. 2,456,477 filed on Aug. 21, 2002.
Japanese Office Action mailed Jul. 1, 2009 for corresponding Japanese Application No. 2003-520767 filed on Aug. 21, 2002, 14 pages.
Scott et al., "Cationic Antimicrobial Peptides an Their Multifunctional Role in the Immune System," Critical Reviews in Immunology vol. 20, 2000, pp. 407-431.

McNicol., P. J. et al., "MBI 594AN is Active Against Acne Vulgaris Organisms, Does Not Induce Resistance and Has Anti-Inflammatory Activity in Vivo," Abstracts of the Interscience Conference on Antimicrobial Agents and Chemotherapy, Interscience Conference on Antimicrobial Agents and Chemotherapy, Dec. 16-17, 2001, Abstract No. F-349.
Gough, M. et al., "Antiendotoxin Actvity of Cationic Peptide Antimicrobial Agents," Infection and Immunity, vol. 64, No. 12, Dec. 1996, pp. 4922-4927.
Masera, R. G. et al., "Coricostatins/defensins Inhibit in vitro NK Activity and Cytokine Production by Human Peripheral Blood Mononuclear Cells," Regulatory Peptides, vol. 62, 1996, pp. 13-21.
Scott, M. G. et al., "Interaction of Cationic Peptides with Lipoteichoic Acid and Gram-Positive Bacteria," Infection and Immunity, vol. 67, No. 12, Dec. 1999, pp. 6445-6453.
Biosequence Searching for the USPTO (STN International), May 1996, pp. 30-31.
Bundgaard, "Design of Prodrugs," Elsevier Publishing, New York, 1985, pp. 1-92.
Chalk et al., "Full Sequence and Characterization of Two Insect Defensins: Immune Peptides from the Mosquito Aedes aegypti," Proceedings of the Royal Society B, Biological Sciences, vol. 261, No. 1361, 1995, pp. 217-221.
Chalk et al., "Purification of an Insect Defensin from Mosquito, Aedes aegypti," Insect Biochemistry and Molecular Biology, vol. 24, No. 4, 1994, pp. 403-410.
Darveau et al., "Beta-Lactam Antibiotics Potentiate Magainin 2 Antimicrobial Activity In Vitro and In Vivo," Antimicrobial Agents and Chemotherapy, vol. 35, No. 6, Jun. 1991, pp. 1153-1159.
Engstrom et al., "The Antibacterial Effect of Attacins from the Silk Moth Hyalophora cecropuia is Directed Against the Outer Membrance of *Eschericia coli*," EMBO Journal, vol. 3, No. 13, 1984, pp. 3347-3351.
Falla et al., "Improved Activity of Synthetic Indolicidin Analog," Antimicrobial Agents and Chemotherapy, vol. 41, No. 4, Apr. 1997, pp. 771-775.
Falla et al., "Mode of Action of the Antimicrobial Peptide Indolicidin," Journal of Biological Chemistry, vol. 271, No. 32, Aug. 1996, pp. 19298-19303.
Hancock, "The Role of Fundamental Research and Biotechnology in Finding Solutions to the Global Problem of Antibiotic Resistance," Clinical Infection Diseases, vol. 24, Suppl. 1, 1997, pp. S148-S150.
Haas, D. W. et al., "Antimicrobial Prophylaxis of Infections Associated with Foreign Bodies," in Infections Associated with Indweliing Medical Devices, 3rd ed., F.A. Waldvogel et al., (eds.), ASM Press, Washington, D.C., 2000, pp. 395-406.
Ladokhin et al., "CD Spectra of Indolicidin Antimicrobial Peptides Suggest Turns, Not Polyproline Helix," Biochemistry, vol. 38, 1999, pp. 12313-12319.
Lawyer et al., "Antimicrobial Activity of a 13 Amino acid Tryptophan-Rich Peptide Derived From a Putative Procine Precursor Protein of a Novel Family of Antibacterial Peptides," FEBS Letters, vol. 390, 1996, pp. 95-98.
Maki, D. G., "Pathogenesis, Prevention, and Management of Infections Due to Intravasoular Devices Used for Infusion Therapy: Pathogenesis, Prevention and Management," In Infection Associated with Indwelling Medical Devices, 2nd Ed., A.L. Bisno et al., (eds.), ASM Press, Washington D.C., 1994, pp. 167-177.
Mermel, L. A., "Preventative Strategies for intravascular Catheter-Related Infections," in Infections Associated with Indwelling Medical Devices, 3rd ed., F. A. Waldvogel et al., (eds.), ASM Press, Washington, D.C., 2000, pp. 407-425.
Piers et al., "Improvement of Outer Membrane-Permeabilizing and Lipopolysaccharide-Binding Activities of an Antimicrobial Cationic Peptide by C-Terminal Modification," Antimicrobial Agents & Chemotherapy, vol. 38, No. 10, Oct. 1994, pp. 2311-2316.
Robinson, Jr. et al., "Anti-HIV-1 Activity of Indolicidin, an Antimicrobial Peptide from Neutrophils," Journal of Leukocyte Biology, vol. 63, Jan. 1998, pp. 94-100.
Selsted et al., "Indolicidin, a Novel Bactericidal Tridecapeptide Amide from Neutrophils," The Journal of Biological Chemistry, vol. 267, No. 7, Mar. 1992, pp. 4292-4295.

Selsted et al., "Purification, Characterization, Synthesis and cDNA Cloning of Indolicidin: A Tryptophan-Rich Microbicidal Tridecapeptide from Neutrophils," Proceedings of the 12th American Peptide Symposium, Cambridge, MA, Jun. 16-21, 1991, pp. 905-907.

Subbalakshimi et al., "Mechanism of Antimicrobial Action of Indolicidin," FEMS Microbiology Letters, vol. 160, 1998, pp. 91-96.

Subbalakshmi et al., "Interaction of Indolicidin, a 13-Residue Peptide Rich in Tryptophan and Proline and its Analogues with Model Membranes," Journal of Biosciences, vol. 23, No. 1, Mar. 1998, pp. 9-13.

Subbalakshmi et al., "Requirements for Antibacterial and Hemolytic Activities in the Bovine Neutrophil Derived 13-Residue Peptide Indolicidin," FEBS Letters, vol. 395, 1996, pp. 48-52.

Tanchak et al., "Tryptophanins: Isolation and Molecular Characterization of Oat cDNA Clones Encoding Proteins Structurally Related to Puroindoline and Wheat Grain Softness Proteins," Plant Science, vol. 137, 1998, pp. 173-184.

Uchida et al., "Antibacterial Activity of the Mammalian Host Defense Peptide, Indolicidin and its Fragments," Peptide Chemistry, 1995, pp. 229-232.

Uchida et al., "Structure-Activity of Antibacterial Peptide Indolicidin and Analogs," Peptide Science, 1998, pp. 221-224.

Vaara et al., "Group of Peptides that Act Synergistically with Hydrophobic Antibiotics Against Gram-Negative Enteric Bacteria," Antimicrobial Agents & Chemotherapy, vol. 40, No. 8, Aug. 1996, pp. 1801-1805.

Vaara et al., "Ability of Cecropin B to Penetrate the Enterobacterial Outer Membrane," Antimicrobial Agents & Chemotherapy, vol. 38, No. 10, Oct. 1994, pp. 2498-2501.

Vaara et al., "Polycations Sensitize Enteric Bacteria to Antibiotics," Antimicrobial Agents & Chemotherapy, vol. 24, No. 1, Jul. 1983, pp. 107-113.

Vaara et al., "Sensitization of Gram-Negative Bacteria to Antibiotics and Complement by a Nontoxic Oligopeptide," Nature, vol. 303, Jun. 9, 1983, pp. 526-528.

Vaara, "Agents that Increase the Permeability of the Outer Membrane," Microbiological Reviews. vol. 56, No. 3, Sep. 1992, pp. 395-411.

Vaara, "The Outer Membrane as the Penetration Barrier Against Mupirocin in Gram-Negative Enteric Bacteria," Journal of Antimicrobial Chemotherapy, vol. 29, No. 2, Feb. 1992, pp. 221-222.

Van Abel et al., "Synthesis and Characterization of Indolicidin, a Tryptophan-Rich Antimicrobial Peptide from Bovine Neutrophils," International Journal of Peptide and Protein Research, vol. 45, 1995, pp. 401-409.

Wakabayashi et al., "N-Acylated and D Enantiomer Derivatives of a Nonamer Core Peptide of Lactoferricin B Showing Improved Antimicrobial Activity," Antimicrobial Agents & Chemotherapy, vol. 43, No. 5, May 1999, pp. 1267-1269.

Official Communication for U.S. Appl. No. 10/865,687 mailed Jan. 18, 2007.

Official Communication for U.S. Appl. No. 10/865,687 mailed Sep. 28, 2007.

Official Communication for U.S. Appl. No. 10/865,687 mailed May 14, 2008.

Official Communication for U.S. Appl. No. 10/865,687 mailed Nov. 24, 2008.

Official Communication for U.S. Appl. No. 10/865,687 mailed Sep. 28, 2009.

Official Communication for U.S. Appl. No. 10/865,687 mailed Feb. 15, 2011.

Official Communication for U.S. Appl. No. 10/865,687 mailed Nov. 10, 2011.

```
                        SEQUENCE LISTING

<160> NUMBER OF SEQ ID NOS: 121

<210> SEQ ID NO 1
<211> LENGTH: 18
<212> TYPE: PRT
<213> ORGANISM: Artificial Sequence
<220> FEATURE:
<223> OTHER INFORMATION: Indolicidin analog

<400> SEQUENCE: 1

Gly Asn Asn Arg Pro Val Tyr Ile Pro Gln Pro Arg Pro Pro His Pro
 1               5                  10                  15

Arg Ile

<210> SEQ ID NO 2
<211> LENGTH: 25
<212> TYPE: PRT
```

```
<213> ORGANISM: Artificial Sequence
<220> FEATURE:
<223> OTHER INFORMATION: Indolicidin analog

<400> SEQUENCE: 2

Lys Lys Ala Ala Ala Lys Ala Ala Ala Ala Lys Ala Ala Trp Ala
1               5                   10                  15

Ala Lys Ala Ala Ala Lys Lys Lys Lys
            20                  25

<210> SEQ ID NO 3
<211> LENGTH: 13
<212> TYPE: PRT
<213> ORGANISM: Artificial Sequence
<220> FEATURE:
<223> OTHER INFORMATION: Indolicidin analog

<400> SEQUENCE: 3

Ile Leu Pro Trp Lys Trp Pro Trp Trp Pro Trp Arg Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Indolicidin analog

<400> SEQUENCE: 4

Ile Leu Pro Trp Lys Trp Pro Trp Trp Pro Trp Arg Arg
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Indolicidin analog

<400> SEQUENCE: 5

Ile Leu Lys Lys Trp Pro Trp Trp Pro Trp Arg Arg Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Indolicidin analog

<400> SEQUENCE: 6

Ile Leu Lys Lys Trp Pro Trp Trp Pro Trp Arg Arg Lys
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Indolicidin analog

<400> SEQUENCE: 7

Lys Arg Arg Trp Pro Trp Trp Pro Trp Lys Lys Leu Ile
1               5                   10

<210> SEQ ID NO 8
<211> LENGTH: 13
```

```
<212> TYPE: PRT
<213> ORGANISM: Artificial Sequence
<220> FEATURE:
<223> OTHER INFORMATION: Indolicidin analog

<400> SEQUENCE: 8

Ile Leu Lys Lys Phe Pro Phe Phe Pro Phe Arg Arg Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Indolicidin analog

<400> SEQUENCE: 9

Ile Leu Lys Lys Ile Pro Ile Ile Pro Ile Arg Arg Lys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Indolicidin analog

<400> SEQUENCE: 10

Ile Leu Lys Lys Tyr Pro Tyr Tyr Pro Tyr Arg Arg Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Indolicidin analog

<400> SEQUENCE: 11

Ile Leu Lys Lys Trp Pro Trp Pro Trp Arg Arg Lys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Indolicidin analog

<400> SEQUENCE: 12

Ile Leu Lys Lys Tyr Pro Trp Tyr Pro Trp Arg Arg Lys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Indolicidin analog

<400> SEQUENCE: 13

Ile Leu Lys Lys Phe Pro Trp Phe Pro Trp Arg Arg Lys
1               5                   10

<210> SEQ ID NO 14
<211> LENGTH: 13
<212> TYPE: PRT
<213> ORGANISM: Artificial Sequence
```

<220> FEATURE:
<223> OTHER INFORMATION: Indolicidin analog

<400> SEQUENCE: 14

Ile Leu Lys Lys Phe Pro Phe Trp Pro Trp Arg Arg Lys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Indolicidin analog

<400> SEQUENCE: 15

Ile Leu Arg Tyr Val Tyr Tyr Val Tyr Arg Arg Lys
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Indolicidin analog

<400> SEQUENCE: 16

Ile Leu Arg Trp Pro Trp Trp Pro Trp Trp Pro Trp Arg Arg Lys
1               5                   10                  15

<210> SEQ ID NO 17
<211> LENGTH: 12
<212> TYPE: PRT
<213> ORGANISM: Artificial Sequence
<220> FEATURE:
<223> OTHER INFORMATION: Indolicidin analog

<400> SEQUENCE: 17

Trp Trp Arg Trp Pro Trp Trp Pro Trp Arg Arg Lys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Indolicidin analog

<400> SEQUENCE: 18

Ile Leu Arg Arg Trp Pro Trp Trp Pro Trp Arg Arg Lys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Indolicidin analog

<400> SEQUENCE: 19

Ile Leu Arg Arg Trp Pro Trp Trp Pro Trp Arg Lys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Indolicidin analog

<400> SEQUENCE: 20

Ile Leu Lys Trp Pro Trp Trp Pro Trp Arg Arg Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Indolicidin analog

<400> SEQUENCE: 21

Ile Leu Lys Lys Trp Pro Trp Trp Pro Trp Arg Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Indolicidin analog

<400> SEQUENCE: 22

Ile Leu Lys Trp Pro Trp Trp Pro Trp Arg Lys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Indolicidin analog

<400> SEQUENCE: 23

Ile Leu Arg Trp Pro Trp Trp Pro Trp Arg Arg Lys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Indolicidin analog

<400> SEQUENCE: 24

Lys Arg Arg Trp Pro Trp Trp Pro Trp Arg Leu Ile
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Indolicidin analog

<400> SEQUENCE: 25

Ile Leu Trp Pro Trp Trp Pro Trp Arg Arg Lys
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Indolicidin analog

<400> SEQUENCE: 26

```
Ile Leu Arg Arg Trp Pro Trp Trp Pro Trp Arg Arg Arg
1               5                   10
```

<210> SEQ ID NO 27
<211> LENGTH: 13
<212> TYPE: PRT
<213> ORGANISM: Artificial Sequence
<220> FEATURE:
<223> OTHER INFORMATION: Indolicidin analog

<400> SEQUENCE: 27

```
Ile Leu Lys Lys Trp Pro Trp Trp Pro Trp Lys Lys Lys
1               5                   10
```

<210> SEQ ID NO 28
<211> LENGTH: 21
<212> TYPE: PRT
<213> ORGANISM: Artificial Sequence
<220> FEATURE:
<223> OTHER INFORMATION: Indolicidin analog

<400> SEQUENCE: 28

```
Ile Leu Arg Trp Pro Trp Trp Pro Trp Arg Arg Lys Ile Met Ile Leu
1               5                   10                  15

Lys Lys Ala Gly Ser
            20
```

<210> SEQ ID NO 29
<211> LENGTH: 20
<212> TYPE: PRT
<213> ORGANISM: Artificial Sequence
<220> FEATURE:
<223> OTHER INFORMATION: Indolicidin analog

<400> SEQUENCE: 29

```
Ile Leu Arg Trp Pro Trp Trp Pro Trp Arg Arg Lys Met Ile Leu Lys
1               5                   10                  15

Lys Ala Gly Ser
            20
```

<210> SEQ ID NO 30
<211> LENGTH: 21
<212> TYPE: PRT
<213> ORGANISM: Artificial Sequence
<220> FEATURE:
<223> OTHER INFORMATION: Indolicidin analog

<400> SEQUENCE: 30

```
Ile Leu Arg Trp Pro Trp Trp Pro Trp Arg Arg Lys Asp Met Ile Leu
1               5                   10                  15

Lys Lys Ala Gly Ser
            20
```

<210> SEQ ID NO 31
<211> LENGTH: 14
<212> TYPE: PRT
<213> ORGANISM: Artificial Sequence
<220> FEATURE:
<223> OTHER INFORMATION: Indolicidin analog

<400> SEQUENCE: 31

```
Ile Leu Arg Trp Pro Trp Arg Arg Trp Pro Trp Arg Arg Lys
1               5                   10
```

<210> SEQ ID NO 32

```
<211> LENGTH: 28
<212> TYPE: PRT
<213> ORGANISM: Artificial Sequence
<220> FEATURE:
<223> OTHER INFORMATION: Indolicidin analog

<400> SEQUENCE: 32

Ile Leu Arg Trp Pro Trp Trp Pro Trp Arg Arg Lys Ile Leu Met Arg
1               5                   10                  15

Trp Pro Trp Trp Pro Trp Arg Arg Lys Met Ala Ala
            20                  25

<210> SEQ ID NO 33
<211> LENGTH: 12
<212> TYPE: PRT
<213> ORGANISM: Artificial Sequence
<220> FEATURE:
<223> OTHER INFORMATION: Indolicidin analog

<400> SEQUENCE: 33

Lys Arg Lys Trp Pro Trp Trp Pro Trp Arg Leu Ile
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Indolicidin analog

<400> SEQUENCE: 34

Ile Leu Lys Trp Val Trp Trp Val Trp Arg Arg Lys
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Indolicidin analog

<400> SEQUENCE: 35

Ile Leu Lys Lys Trp Ala Trp Trp Pro Trp Arg Arg Lys
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Indolicidin analog

<400> SEQUENCE: 36

Ile Leu Lys Lys Trp Pro Trp Trp Ala Trp Arg Arg Lys
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Indolicidin analog

<400> SEQUENCE: 37

Trp Trp Lys Lys Trp Pro Trp Trp Pro Trp Arg Arg Lys
1               5                   10
```

```
<210> SEQ ID NO 38
<211> LENGTH: 12
<212> TYPE: PRT
<213> ORGANISM: Artificial Sequence
<220> FEATURE:
<223> OTHER INFORMATION: Indolicidin analog

<400> SEQUENCE: 38

Leu Lys Lys Trp Pro Trp Trp Pro Trp Arg Arg Lys
 1               5                  10

<210> SEQ ID NO 39
<211> LENGTH: 8
<212> TYPE: PRT
<213> ORGANISM: Artificial Sequence
<220> FEATURE:
<223> OTHER INFORMATION: Indolicidin analog

<400> SEQUENCE: 39

Pro Trp Trp Pro Trp Arg Arg Lys
 1               5

<210> SEQ ID NO 40
<211> LENGTH: 21
<212> TYPE: PRT
<213> ORGANISM: Artificial Sequence
<220> FEATURE:
<223> OTHER INFORMATION: Indolicidin analog

<400> SEQUENCE: 40

Ile Leu Lys Lys Trp Pro Trp Trp Pro Trp Arg Arg Lys Met Ile Leu
 1               5                  10                  15

Lys Lys Ala Gly Ser
            20

<210> SEQ ID NO 41
<211> LENGTH: 20
<212> TYPE: PRT
<213> ORGANISM: Artificial Sequence
<220> FEATURE:
<223> OTHER INFORMATION: Indolicidin analog

<400> SEQUENCE: 41

Ile Leu Lys Lys Trp Pro Trp Trp Pro Trp Arg Arg Met Ile Leu Lys
 1               5                  10                  15

Lys Ala Gly Ser
            20

<210> SEQ ID NO 42
<211> LENGTH: 21
<212> TYPE: PRT
<213> ORGANISM: Artificial Sequence
<220> FEATURE:
<223> OTHER INFORMATION: Indolicidin analog

<400> SEQUENCE: 42

Ile Leu Lys Lys Trp Pro Trp Trp Pro Trp Arg Arg Ile Met Ile Leu
 1               5                  10                  15

Lys Lys Ala Gly Ser
            20

<210> SEQ ID NO 43
<211> LENGTH: 7
<212> TYPE: PRT
<213> ORGANISM: Artificial Sequence
<220> FEATURE:
<223> OTHER INFORMATION: Indolicidin analog
```

```
<400> SEQUENCE: 43

Trp Trp Pro Trp Arg Arg Lys
1               5

<210> SEQ ID NO 44
<211> LENGTH: 7
<212> TYPE: PRT
<213> ORGANISM: Artificial Sequence
<220> FEATURE:
<223> OTHER INFORMATION: Indolicidin analog

<400> SEQUENCE: 44

Ile Leu Lys Lys Trp Pro Trp
1               5

<210> SEQ ID NO 45
<211> LENGTH: 14
<212> TYPE: PRT
<213> ORGANISM: Artificial Sequence
<220> FEATURE:
<223> OTHER INFORMATION: Indolicidin analog

<400> SEQUENCE: 45

Ile Leu Lys Lys Trp Pro Trp Trp Pro Trp Arg Arg Lys Met
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Indolicidin analog

<400> SEQUENCE: 46

Ile Leu Lys Lys Trp Pro Trp Trp Pro Trp Arg Arg Met
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Indolicidin analog

<400> SEQUENCE: 47

Ile Leu Lys Lys Trp Pro Trp Trp Pro Trp Arg Arg Ile Met
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Indolicidin analog

<400> SEQUENCE: 48

Ile Leu Lys Lys Trp Trp Trp Pro Trp Arg Lys
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Indolicidin analog

<400> SEQUENCE: 49
```

```
Ile Leu Lys Lys Trp Pro Trp Trp Arg Lys
 1               5                   10

<210> SEQ ID NO 50
<211> LENGTH: 13
<212> TYPE: PRT
<213> ORGANISM: Artificial Sequence
<220> FEATURE:
<223> OTHER INFORMATION: Indolicidin analog

<400> SEQUENCE: 50

Trp Arg Ile Trp Lys Pro Lys Trp Arg Leu Pro Lys Trp
 1               5                   10

<210> SEQ ID NO 51
<211> LENGTH: 12
<212> TYPE: PRT
<213> ORGANISM: Artificial Sequence
<220> FEATURE:
<223> OTHER INFORMATION: Indolicidin analog

<400> SEQUENCE: 51

Cys Leu Arg Trp Pro Trp Trp Pro Trp Arg Arg Lys
 1               5                   10

<210> SEQ ID NO 52
<211> LENGTH: 13
<212> TYPE: PRT
<213> ORGANISM: Artificial Sequence
<220> FEATURE:
<223> OTHER INFORMATION: Indolicidin analog

<400> SEQUENCE: 52

Ile Leu Lys Lys Trp Pro Trp Trp Pro Trp Arg Arg Lys
 1               5                   10

<210> SEQ ID NO 53
<211> LENGTH: 13
<212> TYPE: PRT
<213> ORGANISM: Artificial Sequence
<220> FEATURE:
<223> OTHER INFORMATION: Indolicidin analog

<400> SEQUENCE: 53

Ile Leu Lys Lys Trp Pro Trp Trp Pro Trp Arg Arg Lys
 1               5                   10

<210> SEQ ID NO 54
<211> LENGTH: 13
<212> TYPE: PRT
<213> ORGANISM: Artificial Sequence
<220> FEATURE:
<223> OTHER INFORMATION: Indolicidin analog

<400> SEQUENCE: 54

Ile Leu Lys Lys Trp Pro Trp Trp Pro Trp Arg Arg Lys
 1               5                   10

<210> SEQ ID NO 55
<211> LENGTH: 13
<212> TYPE: PRT
<213> ORGANISM: Artificial Sequence
<220> FEATURE:
<223> OTHER INFORMATION: Indolicidin analog

<400> SEQUENCE: 55

Ile Leu Lys Lys Trp Val Trp Trp Val Trp Arg Arg Lys
```

<210> SEQ ID NO 56
<211> LENGTH: 13
<212> TYPE: PRT
<213> ORGANISM: Artificial Sequence
<220> FEATURE:
<223> OTHER INFORMATION: Indolicidin analog

<400> SEQUENCE: 56

Ile Leu Lys Lys Trp Pro Trp Trp Val Trp Arg Arg Lys
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Indolicidin analog

<400> SEQUENCE: 57

Ile Leu Lys Lys Trp Val Trp Trp Pro Trp Arg Arg Lys
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Indolicidin analog

<400> SEQUENCE: 58

Ile Leu Arg Trp Val Trp Trp Val Trp Arg Arg Lys
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Indolicidin analog

<400> SEQUENCE: 59

Lys Arg Arg Trp Val Trp Trp Val Trp Arg Leu Ile
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Indolicidin analog

<400> SEQUENCE: 60

Ile Leu Arg Arg Trp Val Trp Trp Val Trp Arg Arg Lys
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Indolicidin analog

<400> SEQUENCE: 61

Ile Leu Arg Trp Trp Val Trp Trp Val Trp Trp Arg Arg Lys
1               5                   10

```
<210> SEQ ID NO 62
<211> LENGTH: 11
<212> TYPE: PRT
<213> ORGANISM: Artificial Sequence
<220> FEATURE:
<223> OTHER INFORMATION: Indolicidin analog

<400> SEQUENCE: 62

Arg Leu Trp Val Trp Trp Val Trp Arg Arg Lys
 1               5                  10

<210> SEQ ID NO 63
<211> LENGTH: 10
<212> TYPE: PRT
<213> ORGANISM: Artificial Sequence
<220> FEATURE:
<223> OTHER INFORMATION: Indolicidin analog

<400> SEQUENCE: 63

Arg Leu Trp Val Trp Trp Val Trp Arg Arg
 1               5                  10

<210> SEQ ID NO 64
<211> LENGTH: 13
<212> TYPE: PRT
<213> ORGANISM: Artificial Sequence
<220> FEATURE:
<223> OTHER INFORMATION: Indolicidin analog

<400> SEQUENCE: 64

Arg Leu Gly Gly Gly Trp Val Trp Trp Val Trp Arg Arg
 1               5                  10

<210> SEQ ID NO 65
<211> LENGTH: 10
<212> TYPE: PRT
<213> ORGANISM: Artificial Sequence
<220> FEATURE:
<223> OTHER INFORMATION: Indolicidin analog

<400> SEQUENCE: 65

Arg Leu Trp Trp Val Val Trp Trp Arg Arg
 1               5                  10

<210> SEQ ID NO 66
<211> LENGTH: 10
<212> TYPE: PRT
<213> ORGANISM: Artificial Sequence
<220> FEATURE:
<223> OTHER INFORMATION: Indolicidin analog

<400> SEQUENCE: 66

Arg Leu Val Val Trp Trp Val Val Arg Arg
 1               5                  10

<210> SEQ ID NO 67
<211> LENGTH: 10
<212> TYPE: PRT
<213> ORGANISM: Artificial Sequence
<220> FEATURE:
<223> OTHER INFORMATION: Indolicidin analog

<400> SEQUENCE: 67

Arg Leu Phe Val Trp Trp Val Phe Arg Arg
 1               5                  10

<210> SEQ ID NO 68
```

```
<211> LENGTH: 10
<212> TYPE: PRT
<213> ORGANISM: Artificial Sequence
<220> FEATURE:
<223> OTHER INFORMATION: Indolicidin analog

<400> SEQUENCE: 68

Arg Leu Val Val Trp Val Val Trp Arg Arg
 1               5                  10

<210> SEQ ID NO 69
<211> LENGTH: 10
<212> TYPE: PRT
<213> ORGANISM: Artificial Sequence
<220> FEATURE:
<223> OTHER INFORMATION: Indolicidin analog

<400> SEQUENCE: 69

Arg Leu Trp Val Trp Trp Val Trp Arg Arg
 1               5                  10

<210> SEQ ID NO 70
<211> LENGTH: 10
<212> TYPE: PRT
<213> ORGANISM: Artificial Sequence
<220> FEATURE:
<223> OTHER INFORMATION: Indolicidin analog

<400> SEQUENCE: 70

Arg Leu Trp Val Trp Trp Val Trp Arg Arg
 1               5                  10

<210> SEQ ID NO 71
<211> LENGTH: 10
<212> TYPE: PRT
<213> ORGANISM: Artificial Sequence
<220> FEATURE:
<223> OTHER INFORMATION: Indolicidin analog

<400> SEQUENCE: 71

Trp Val Arg Leu Trp Trp Arg Arg Val Trp
 1               5                  10

<210> SEQ ID NO 72
<211> LENGTH: 12
<212> TYPE: PRT
<213> ORGANISM: Artificial Sequence
<220> FEATURE:
<223> OTHER INFORMATION: Indolicidin analog

<400> SEQUENCE: 72

Ile Lys Lys Trp Pro Trp Trp Pro Trp Arg Arg Lys
 1               5                  10

<210> SEQ ID NO 73
<211> LENGTH: 12
<212> TYPE: PRT
<213> ORGANISM: Artificial Sequence
<220> FEATURE:
<223> OTHER INFORMATION: Indolicidin analog

<400> SEQUENCE: 73

Ile Leu Lys Lys Pro Trp Trp Pro Trp Arg Arg Lys
 1               5                  10

<210> SEQ ID NO 74
<211> LENGTH: 12
<212> TYPE: PRT
```

<213> ORGANISM: Artificial Sequence
<220> FEATURE:
<223> OTHER INFORMATION: Indolicidin analog

<400> SEQUENCE: 74

Ile Leu Lys Lys Trp Trp Trp Pro Trp Arg Arg Lys
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Indolicidin analog

<400> SEQUENCE: 75

Ile Leu Lys Lys Trp Pro Trp Trp Trp Arg Arg Lys
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Indolicidin analog

<400> SEQUENCE: 76

Ile Leu Lys Lys Trp Pro Trp Trp Pro Arg Arg Lys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Indolicidin analog

<400> SEQUENCE: 77

Ile Leu Lys Lys Trp Pro Trp Trp Pro Trp Arg Arg
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Indolicidin analog

<400> SEQUENCE: 78

Ile Leu Lys Lys Trp Pro Trp Trp Pro Trp Lys
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Indolicidin analog

<400> SEQUENCE: 79

Ile Leu Lys Lys Trp Pro Trp Trp Pro Trp Arg
1               5                   10

<210> SEQ ID NO 80
<211> LENGTH: 10
<212> TYPE: PRT
<213> ORGANISM: Artificial Sequence
<220> FEATURE:

<223> OTHER INFORMATION: Indolicidin analog

<400> SEQUENCE: 80

Leu Trp Pro Trp Trp Pro Trp Arg Arg Lys
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Indolicidin analog

<400> SEQUENCE: 81

Leu Arg Trp Trp Trp Pro Trp Arg Arg Lys
1               5                   10

<210> SEQ ID NO 82
<211> LENGTH: 8
<212> TYPE: PRT
<213> ORGANISM: Artificial Sequence
<220> FEATURE:
<223> OTHER INFORMATION: Indolicidin analog

<400> SEQUENCE: 82

Leu Arg Trp Pro Trp Trp Pro Trp
1               5

<210> SEQ ID NO 83
<211> LENGTH: 9
<212> TYPE: PRT
<213> ORGANISM: Artificial Sequence
<220> FEATURE:
<223> OTHER INFORMATION: Indolicidin analog

<400> SEQUENCE: 83

Trp Pro Trp Trp Pro Trp Arg Arg Lys
1               5

<210> SEQ ID NO 84
<211> LENGTH: 9
<212> TYPE: PRT
<213> ORGANISM: Artificial Sequence
<220> FEATURE:
<223> OTHER INFORMATION: Indolicidin analog

<400> SEQUENCE: 84

Arg Trp Trp Trp Pro Trp Arg Arg Lys
1               5

<210> SEQ ID NO 85
<211> LENGTH: 12
<212> TYPE: PRT
<213> ORGANISM: Artificial Sequence
<220> FEATURE:
<223> OTHER INFORMATION: Indolicidin analog

<400> SEQUENCE: 85

Ala Leu Arg Trp Pro Trp Trp Pro Trp Arg Arg Lys
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Indolicidin analog

```
<400> SEQUENCE: 86

Ile Ala Arg Trp Pro Trp Trp Pro Trp Arg Arg Lys
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Indolicidin analog

<400> SEQUENCE: 87

Ile Leu Ala Trp Pro Trp Trp Pro Trp Arg Arg Lys
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Indolicidin analog

<400> SEQUENCE: 88

Ile Leu Arg Ala Pro Trp Trp Pro Trp Arg Arg Lys
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Indolicidin analog

<400> SEQUENCE: 89

Ile Leu Arg Trp Ala Trp Trp Pro Trp Arg Arg Lys
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Indolicidin analog

<400> SEQUENCE: 90

Ile Leu Arg Trp Pro Ala Trp Pro Trp Arg Arg Lys
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Indolicidin analog

<400> SEQUENCE: 91

Ile Leu Arg Trp Pro Trp Ala Pro Trp Arg Arg Lys
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Indolicidin analog

<400> SEQUENCE: 92
```

```
Ile Leu Arg Trp Pro Trp Trp Ala Trp Arg Arg Lys
1               5                   10
```

<210> SEQ ID NO 93
<211> LENGTH: 12
<212> TYPE: PRT
<213> ORGANISM: Artificial Sequence
<220> FEATURE:
<223> OTHER INFORMATION: Indolicidin analog

<400> SEQUENCE: 93

```
Ile Leu Arg Trp Pro Trp Trp Pro Ala Arg Arg Lys
1               5                   10
```

<210> SEQ ID NO 94
<211> LENGTH: 12
<212> TYPE: PRT
<213> ORGANISM: Artificial Sequence
<220> FEATURE:
<223> OTHER INFORMATION: Indolicidin analog

<400> SEQUENCE: 94

```
Ile Leu Arg Trp Pro Trp Trp Pro Trp Ala Arg Lys
1               5                   10
```

<210> SEQ ID NO 95
<211> LENGTH: 12
<212> TYPE: PRT
<213> ORGANISM: Artificial Sequence
<220> FEATURE:
<223> OTHER INFORMATION: Indolicidin analog

<400> SEQUENCE: 95

```
Ile Leu Arg Trp Pro Trp Trp Pro Trp Arg Ala Lys
1               5                   10
```

<210> SEQ ID NO 96
<211> LENGTH: 12
<212> TYPE: PRT
<213> ORGANISM: Artificial Sequence
<220> FEATURE:
<223> OTHER INFORMATION: Indolicidin analog

<400> SEQUENCE: 96

```
Ile Leu Arg Trp Pro Trp Trp Pro Trp Arg Arg Ala
1               5                   10
```

<210> SEQ ID NO 97
<211> LENGTH: 13
<212> TYPE: PRT
<213> ORGANISM: Artificial Sequence
<220> FEATURE:
<223> OTHER INFORMATION: Indolicidin analog

<400> SEQUENCE: 97

```
Arg Arg Ile Trp Lys Pro Lys Trp Arg Leu Pro Lys Arg
1               5                   10
```

<210> SEQ ID NO 98
<211> LENGTH: 13
<212> TYPE: PRT
<213> ORGANISM: Artificial Sequence
<220> FEATURE:
<223> OTHER INFORMATION: Indolicidin analog

<400> SEQUENCE: 98

```
Trp Arg Trp Trp Lys Pro Lys Trp Arg Trp Pro Lys Trp
1               5                   10
```

```
<210> SEQ ID NO 99
<211> LENGTH: 13
<212> TYPE: PRT
<213> ORGANISM: Artificial Sequence
<220> FEATURE:
<223> OTHER INFORMATION: Indolicidin analog

<400> SEQUENCE: 99

Trp Arg Trp Trp Lys Pro Lys Trp Arg Trp Pro Lys Trp
 1               5                  10

<210> SEQ ID NO 100
<211> LENGTH: 13
<212> TYPE: PRT
<213> ORGANISM: Artificial Sequence
<220> FEATURE:
<223> OTHER INFORMATION: Indolicidin analog

<400> SEQUENCE: 100

Trp Arg Trp Trp Lys Val Ala Trp Arg Trp Val Lys Trp
 1               5                  10

<210> SEQ ID NO 101
<211> LENGTH: 12
<212> TYPE: PRT
<213> ORGANISM: Artificial Sequence
<220> FEATURE:
<223> OTHER INFORMATION: Indolicidin analog

<400> SEQUENCE: 101

Trp Arg Trp Trp Lys Val Trp Arg Trp Val Lys Trp
 1               5                  10

<210> SEQ ID NO 102
<211> LENGTH: 13
<212> TYPE: PRT
<213> ORGANISM: Artificial Sequence
<220> FEATURE:
<223> OTHER INFORMATION: Indolicidin analog

<400> SEQUENCE: 102

Trp Arg Trp Trp Lys Val Val Trp Arg Trp Val Lys Trp
 1               5                  10

<210> SEQ ID NO 103
<211> LENGTH: 13
<212> TYPE: PRT
<213> ORGANISM: Artificial Sequence
<220> FEATURE:
<223> OTHER INFORMATION: Indolicidin analog
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Orn
<220> FEATURE:
<221> NAME/KEY: MOD_RES
<222> LOCATION: (9)...(9)
<223> OTHER INFORMATION: Orn
<220> FEATURE:
<221> NAME/KEY: MOD_RES
<222> LOCATION: (12)...(12)
<223> OTHER INFORMATION: Orn

<400> SEQUENCE: 103

Trp Xaa Trp Trp Xaa Val Ala Trp Xaa Trp Val Xaa Trp
```

```
<210> SEQ ID NO 104
<211> LENGTH: 13
<212> TYPE: PRT
<213> ORGANISM: Artificial Sequence
<220> FEATURE:
<223> OTHER INFORMATION: Indolicidin analog
<220> FEATURE:
<221> NAME/KEY: MOD_RES
<222> LOCATION: (2)...(2)
<223> OTHER INFORMATION: Orn
<220> FEATURE:
<221> NAME/KEY: MOD_RES
<222> LOCATION: (5)...(5)
<223> OTHER INFORMATION: Orn
<220> FEATURE:
<221> NAME/KEY: MOD_RES
<222> LOCATION: (7)...(7)
<223> OTHER INFORMATION: Orn
<220> FEATURE:
<221> NAME/KEY: MOD_RES
<222> LOCATION: (9)...(9)
<223> OTHER INFORMATION: Orn
<220> FEATURE:
<221> NAME/KEY: MOD_RES
<222> LOCATION: (12)...(12)
<223> OTHER INFORMATION: Orn

<400> SEQUENCE: 104

Trp Xaa Trp Trp Xaa Pro Xaa Trp Xaa Trp Pro Xaa Trp
 1               5                  10

<210> SEQ ID NO 105
<211> LENGTH: 13
<212> TYPE: PRT
<213> ORGANISM: Artificial Sequence
<220> FEATURE:
<223> OTHER INFORMATION: Indolicidin analog
<220> FEATURE:
<221> NAME/KEY: MOD_RES
<222> LOCATION: (2)...(2)
<223> OTHER INFORMATION: Dbu
<220> FEATURE:
<221> NAME/KEY: MOD_RES
<222> LOCATION: (5)...(5)
<223> OTHER INFORMATION: Dbu
<220> FEATURE:
<221> NAME/KEY: MOD_RES
<222> LOCATION: (7)...(7)
<223> OTHER INFORMATION: Dbu
<220> FEATURE:
<221> NAME/KEY: MOD_RES
<222> LOCATION: (9)...(9)
<223> OTHER INFORMATION: Dbu
<220> FEATURE:
<221> NAME/KEY: MOD_RES
<222> LOCATION: (12)...(12)
<223> OTHER INFORMATION: Dbu

<400> SEQUENCE: 105

Trp Xaa Trp Trp Xaa Pro Xaa Trp Xaa Trp Pro Xaa Trp
 1               5                  10

<210> SEQ ID NO 106
<211> LENGTH: 24
<212> TYPE: PRT
<213> ORGANISM: Artificial Sequence
<220> FEATURE:
<223> OTHER INFORMATION: Indolicidin analog

<400> SEQUENCE: 106

Lys Lys Trp Trp Arg Arg Val Leu Ser Gly Leu Lys Thr Ala Gly Pro
 1               5                  10                  15
```

```
Ala Ile Gln Ser Val Leu Asn Lys
            20

<210> SEQ ID NO 107
<211> LENGTH: 24
<212> TYPE: PRT
<213> ORGANISM: Artificial Sequence
<220> FEATURE:
<223> OTHER INFORMATION: Indolicidin analog

<400> SEQUENCE: 107

Lys Lys Trp Trp Arg Arg Ala Leu Gln Gly Leu Lys Thr Ala Gly Pro
1               5                   10                  15

Ala Ile Gln Ser Val Leu Asn Lys
            20

<210> SEQ ID NO 108
<211> LENGTH: 20
<212> TYPE: PRT
<213> ORGANISM: Artificial Sequence
<220> FEATURE:
<223> OTHER INFORMATION: Indolicidin analog

<400> SEQUENCE: 108

Lys Lys Trp Trp Arg Arg Val Leu Lys Gly Leu Ser Ser Gly Pro Ala
1               5                   10                  15

Leu Ser Asn Val
            20

<210> SEQ ID NO 109
<211> LENGTH: 20
<212> TYPE: PRT
<213> ORGANISM: Artificial Sequence
<220> FEATURE:
<223> OTHER INFORMATION: Indolicidin analog

<400> SEQUENCE: 109

Lys Lys Trp Trp Arg Arg Ala Leu Gln Ala Leu Lys Asn Gly Leu Pro
1               5                   10                  15

Ala Leu Ile Ser
            20

<210> SEQ ID NO 110
<211> LENGTH: 26
<212> TYPE: PRT
<213> ORGANISM: Artificial Sequence
<220> FEATURE:
<223> OTHER INFORMATION: Indolicidin analog

<400> SEQUENCE: 110

Lys Trp Lys Ser Phe Ile Lys Lys Leu Thr Ser Ala Ala Lys Lys Val
1               5                   10                  15

Val Thr Thr Ala Lys Pro Leu Ile Ser Ser
            20                  25

<210> SEQ ID NO 111
<211> LENGTH: 26
<212> TYPE: PRT
<213> ORGANISM: Artificial Sequence
<220> FEATURE:
<223> OTHER INFORMATION: Indolicidin analog

<400> SEQUENCE: 111

Lys Trp Lys Leu Phe Lys Lys Ile Gly Ile Gly Ala Val Leu Lys Val
1               5                   10                  15
```

Leu Thr Thr Gly Leu Pro Ala Leu Ile Ser
            20                  25

<210> SEQ ID NO 112
<211> LENGTH: 28
<212> TYPE: PRT
<213> ORGANISM: Artificial Sequence
<220> FEATURE:
<223> OTHER INFORMATION: Indolicidin analog

<400> SEQUENCE: 112

Lys Trp Lys Leu Phe Lys Lys Ile Gly Ile Gly Ala Val Leu Lys Val
1               5                   10                  15

Leu Thr Thr Gly Leu Pro Ala Leu Lys Leu Thr Lys
            20                  25

<210> SEQ ID NO 113
<211> LENGTH: 26
<212> TYPE: PRT
<213> ORGANISM: Artificial Sequence
<220> FEATURE:
<223> OTHER INFORMATION: Indolicidin analog

<400> SEQUENCE: 113

Lys Trp Lys Ser Phe Ile Lys Lys Leu Thr Thr Ala Val Lys Lys Val
1               5                   10                  15

Leu Thr Thr Gly Leu Pro Ala Leu Ile Ser
            20                  25

<210> SEQ ID NO 114
<211> LENGTH: 26
<212> TYPE: PRT
<213> ORGANISM: Artificial Sequence
<220> FEATURE:
<223> OTHER INFORMATION: Indolicidin analog

<400> SEQUENCE: 114

Lys Trp Lys Ser Phe Ile Lys Asn Leu Thr Lys Val Leu Lys Lys Val
1               5                   10                  15

Val Thr Thr Ala Leu Pro Ala Leu Ile Ser
            20                  25

<210> SEQ ID NO 115
<211> LENGTH: 26
<212> TYPE: PRT
<213> ORGANISM: Artificial Sequence
<220> FEATURE:
<223> OTHER INFORMATION: Indolicidin analog

<400> SEQUENCE: 115

Lys Trp Lys Ser Phe Ile Lys Lys Leu Thr Ser Ala Ala Lys Lys Val
1               5                   10                  15

Leu Thr Thr Gly Leu Pro Ala Leu Ile Ser
            20                  25

<210> SEQ ID NO 116
<211> LENGTH: 26
<212> TYPE: PRT
<213> ORGANISM: Artificial Sequence
<220> FEATURE:
<223> OTHER INFORMATION: Indolicidin analog

<400> SEQUENCE: 116

Lys Trp Lys Leu Phe Ile Lys Lys Leu Thr Pro Ala Val Lys Lys Val
1               5                   10                  15

```
Leu Leu Thr Gly Leu Pro Ala Leu Ile Ser
            20                  25

<210> SEQ ID NO 117
<211> LENGTH: 18
<212> TYPE: PRT
<213> ORGANISM: Artificial Sequence
<220> FEATURE:
<223> OTHER INFORMATION: Indolicidin analog

<400> SEQUENCE: 117

Gly Lys Pro Arg Pro Tyr Ser Pro Ile Pro Thr Ser Pro Arg Pro Ile
1               5                   10                  15

Arg Tyr

<210> SEQ ID NO 118
<211> LENGTH: 12
<212> TYPE: PRT
<213> ORGANISM: Artificial Sequence
<220> FEATURE:
<223> OTHER INFORMATION: Indolicidin analog

<400> SEQUENCE: 118

Arg Leu Ala Arg Ile Val Val Ile Arg Val Ala Arg
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Indolicidin analog
<220> FEATURE:
<221> NAME/KEY: MOD_RES
<222> LOCATION: (1)...(1)
<223> OTHER INFORMATION: N - terminal modification (Acryloyl)

<400> SEQUENCE: 119

Ile Leu Arg Trp Pro Trp Trp Pro Trp Arg Arg Lys
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Indolicidin analog
<220> FEATURE:
<221> NAME/KEY: MOD_RES
<222> LOCATION: (1)...(1)
<223> OTHER INFORMATION: N-terminal modification (glucosyl)

<400> SEQUENCE: 120

Trp Arg Trp Trp Lys Val Trp Arg Trp Val Lys Trp
1               5                   10

<210> SEQ ID NO 121
<211> LENGTH: 13
<212> TYPE: PRT
<213> ORGANISM: Artificial Sequence
<220> FEATURE:
<223> OTHER INFORMATION: Indolicidin analog
<220> FEATURE:
<221> NAME/KEY: MOD_RES
<222> LOCATION: (1)...(1)
<223> OTHER INFORMATION: N-terminal modification (glucosyl)
```

-continued

```
<400> SEQUENCE: 121

Trp Arg Trp Trp Lys Val Val Trp Arg Trp Val Lys Trp
1               5                   10
```

ANTIMICROBIAL CATIONIC PEPTIDES AND FORMULATIONS THEREOF

CROSS-REFERENCE TO RELATED APPLICATION

This patent application is a Continuation of U.S. patent application Ser. No. 10/865,687, filed Jun. 10, 2004, which is a Continuation of U.S. Patent Application Ser. No. 10/225,087, now U.S. Pat. No. 6,835,536, filed Aug. 20, 2002, which claims the benefit of U.S. Provisional Patent Application No. 60/314,232 filed Aug. 21, 2001, all of which are incorporated herein by reference in their entireties.

TECHNICAL FIELD

The present invention relates generally to the treatment of infectious disease, and more specifically, to compositions comprising antimicrobial cationic peptides formulated for therapeutic use.

BACKGROUND OF THE INVENTION

During this century, modern society has been successful in controlling infectious disease by, for example, using vaccines, using drugs (such as antibiotics), and using strict public health measures. These advances have been paralleled by successfully identifying the causative agents of infectious disease, which agents include bacteria, fungi, protozoa, and viruses. Thus, aside from a healthy host immune response, antibiotic therapeutic regimens now represent the primary course of treatment for most infectious diseases in developed countries. In contrast, infectious diseases remain a serious concern for developing countries, due to the lack of adequate sanitation and consequent poor hygiene, and for immunocompromised individuals. However, due to the widespread use of antibiotics, drug-resistance to one or more antibiotics is becoming an increasingly common problem all over the world for controlling a number of previously treatable infectious diseases (e.g., Staphylococcal infections). Accordingly, treatment of nosocomial infections (i.e., those arising in hospitals) and infections related to indwelling medical devices is becoming more difficult because of the intractable nature of infections due to drug-resistant microorganisms, which is a serious and world-wide clinical concern.

A variety of artificial devices to assist in the performance of various physiological functions have been developed to be inserted into the human body for short periods, such as catheters, or to be inserted permanently, such as artificial heart valves; however, the interface between the device and body creates new biological conditions that increase the propensity of infection. For example, catheter-associated infections may have multiple potential sources of contaminants, including contaminants in the infusate that is directly injected, contaminants of the catheter hub where the administration set attaches to the catheter, contaminants carried hematogenously from remote sources of local infection to colonize the catheter, or contaminants of cutaneous origin that invade the percutaneous tract extraluminally at the time the catheter is inserted or in the days following insertion. Available evidence indicates that the majority of catheter-related bacteremias originate from the cutaneous microflora of the insertion site. Given the evidence for the importance of cutaneous microorganisms in the pathogenesis of intravascular device-related infections, measures to reduce colonization of the insertion site are of great importance in the health care industry.

Another clinical indication of importance is nosocomial infections and, in particular, nosocomial pneumonia and nosocomial sinusitis. Contaminated secretions may be aspirated daily in the tracheobronchial tree, which may lead to pneumonia. Additionally, the risk of nosocomial pneumonia is increased after a tracheostomy is performed and during prolonged endotracheal intubation. Sinusitis has been found to be associated with an increased risk of nosocomial pneumonia, presumably due aspiration of contaminated sinovial fluids into the distal airways. Sinusitis typically arises in the hospital setting among mechanically ventilated patients. Recommended treatments for sinusitis of intubated patients, include removal of the tubes or systemic antibiotics. However, once again, the increase in antibiotic-resistant organisms makes the latter treatment, whether preventative or curative, less efficacious.

Yet another clinical indication, although not life-threatening, is the most common skin disease of adolescence and early adulthood, acne vulgaris, or acne as it is generally called. In addition to psychological effects, such as anxiety, depression and withdrawal from society, studies have also shown that acne vulgaris can directly and significantly affects a patient's quality of life. Antibiotic agents have been extensively used for the treatment of acne for several decades; however, there is a growing concern that with the use of antibiotics to treat acne, drug-resistant microorganisms will inevitably emerge.

To address the issue of ever increasing drug-resistant microorganisms, investigations have turned to new classes of antibiotics, such as antimicrobial peptides. Antimicrobial peptides are found in evolutionarily diverse species including, for example, prokaryotes, plants, insects, and mammals. Antimicrobial peptides may be anionic, but most known antimicrobial peptides are cationic. Multiple families of antimicrobial cationic peptides are known and these peptides encompass a wide variety of structural motifs, yet all of these cationic peptides have similar physicochemical properties. For example, most known antimicrobial cationic peptides are cationic at neutral pH, are generally less than 10 kDa, and are amphipathically "sided" in solution such that hydrophobic side chains are regionalized. Many antimicrobial cationic peptides are known, including defensins, cecropins, melittins, magainins, indolicidins, and protegrins. The advantages of cationic peptides are their ability to kill target cells rapidly, their broad spectrum of activity, and their activity against some of the more serious antibiotic-resistant and clinically relevant pathogens. Most, importantly, antimicrobial peptide-resistant, microorganisms are relatively difficulty to select in vitro. However, some antimicrobial peptides have been found to be toxic (e.g., bee venom, wasp venom, and scorpion toxin), some have been found to have reduced activity in vivo (due to factors such as high mono- and divalent cation concentrations, polyanions, serum, apolipoprotein A-1, serpins, and proteases, although many peptides are not affected by these factors), and some have been found to be less potent than conventional antibiotics.

Hence, a need exists for identifying modified or derivative antimicrobial peptides with improved activity (and in some cases with reduced toxicity), for formulating such peptides and derivatives thereof for optimal therapeutic use, and for developing therapeutically effective clinical regimens for these cationic peptides. Furthermore, there is a need for formulations that are useful in a variety of clinical indications. The present invention meets such needs, and further provides other related advantages.

SUMMARY OF THE INVENTION

The present invention provides antimicrobial cationic peptides, in particular indolicidin peptides and analogs or derivatives thereof, and formulations of such peptides for use in a variety of therapeutic settings, such as in treating or preventing, for example, infectious disease associated with foreign bodies, primary infection sites, or secondary infections arising from a primary disease state.

In one aspect, the present invention provides a composition that comprises an antimicrobial cationic peptide, a viscosity-increasing agent, and a solvent. In certain embodiments the solvent is water, glycerin, propylene glycol, isopropanol, ethanol, or methanol. In certain other embodiments, the solvent is glycerin at a concentration ranging from about 0.1% to about 20% or from about 9% to about 11%. In still other embodiments, the solvent is propylene glycol at a concentration ranging from about 0.1% to about 20% or from about .9% to about 11%. In yet other embodiments, the solvent comprises at least one of water, glycerin, propylene glycol, isopropanol, ethanol, and methanol. In further embodiments, the solvent comprises at least one of water at a concentration up to 99%, glycerin at a concentration up to 20%, propylene glycol at a concentration up to 20%, ethanol at a concentration up to 99%, and methanol at a concentration up to 99%.

In certain embodiments, the viscosity-increasing agent is dextran, polyvinylpyrrolidone, hydroxyethyl cellulose, or hydroxypropyl methylcellulose. In another embodiment, the viscosity-increasing agent is hydroxyethyl cellulose at a concentration ranging from about 0.5% to about 5% or from about 1% to about 3%. In another embodiment, the viscosity-increasing agent is hydroxypropyl methylcellulose at a concentration ranging from about 1% to about 3%. In other embodiments, the viscosity-increasing agent is dextran at a concentration ranging from about 0.1% to about 5% or from about 0.5% to about 1%. In certain other embodiments, where the viscosity-increasing agent is hydroxyethyl cellulose, the composition further comprises a second viscosity-increasing agent of dextran, polyvinylpyrrolidone, or hydroxypropyl methylcellulose. In one embodiment, the second viscosity-increasing agent is polyvinylpyrrolidone. In related embodiments, the polyvinylpyrrolidone is at a concentration ranging from about 0.1% to about 5% or from about 0.5% to about 1%. In another embodiment, the second viscosity-increasing agent is hydroxypropyl methylcellulose. In related embodiments, the hydroxypropyl methylcellulose is at a concentration ranging from about 1% to about 3%. In certain other embodiments, where the viscosity-increasing agent is hydroxypropyl methylcellulose, the composition further comprises a second viscosity-increasing agent of dextran, or dextran at concentration ranging from about 0.1% to about 5% or from about 0.5% to about 1%. In still other embodiments, where the viscosity-increasing agent is hydroxypropyl methylcellulose, the composition further comprises a second viscosity-increasing, agent of polyvinylpyrrolidone, or polyvinylpyrrolidone at a concentration ranging from about 0.1% to about 5% or from about 0.5% to about 1%. In certain embodiments, the first viscosity-increasing agent comprises hydroxyethyl cellulose at a concentration up to about 3% and second viscosity-increasing agent comprises hydroxypropyl methylcellulose at a concentration up to about 3%.

In another embodiment, the present invention provides a composition comprising an antimicrobial cationic peptide, a viscosity-increasing agent, and a solvent, which further comprises a buffering agent. In certain embodiments, the buffering agent is at a concentration ranging from about 1 mM to about 200 mM. In other embodiments, the buffering agent may comprise a monocarboxylate or a dicarboxylate. In further embodiments, the buffering agent is acetate, fumarate, lactate, malonate, succinate, or tartrate. In yet another embodiment, the composition further comprising a buffering agent has a pH ranging from about 3 to about 8.

In still other embodiments, any of the aforementioned compositions further comprise a humectant. In one embodiment, the humectant is sorbitol or glycerol. In further embodiments, any of the aforementioned compositions further comprise a preservative. In one embodiment, the preservative comprises benzoic acid, benzyl alcohol, phenoxyethanol, methylparaben, propylparaben, or a combination thereof. As used herein, any, reference to an acid may include a free acid, a salt; and any ester thereof. In other embodiments, any of the aforementioned compositions further comprise a humectant and a preservative.

In certain embodiments, the antimicrobial cationic peptide is an indolicidin or an analog or derivative thereof in any one of the aforementioned compositions. In other embodiments, the cationic peptide is at a concentration ranging from about 0.01% to about 10% or from about 0.5% to about 1.5% in any one of the aforementioned compositions. In yet other embodiments, any one of the aforementioned compositions having a cationic peptide that is a peptide of up to 35 amino acids, comprising one of the following sequences: 11B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN.

In another aspect, there is provided a composition comprising an antimicrobial cationic peptide; a viscosity-increasing agent, a solvent, a humectant, and a buffering agent. In one embodiment, the humectant is sorbitol or glycerol. In certain embodiments, the buffering agent is at a concentration ranging from about 1 mM to about 200 mM. In other embodiments, the buffering agent comprises a monocarboxylate or a dicarboxylate. In further embodiments, the buffering agent is acetate, fumarate, lactate, malonate, succinate, or tartrate. In yet another embodiment, the composition has a pH ranging from about 3 to about 8. In another embodiment, the composition further comprises a preservative. In one embodiment, the preservative comprises benzoic acid, benzyl alcohol, phenoxyethanol, methylparaben, propylparaben, or a combination thereof. In certain embodiments, the solvent is water, glycerin, propylene glycol, isopropanol, ethanol, or methanol. In certain other embodiments, the solvent is glycerin at a concentration ranging from about 0.1% to about 20% or from about 9% to about 11%. In still other embodiments, the solvent is propylene glycol at a concentration ranging from about 0.1% to about 20% or from about 9% to about 11%. In yet other embodiments, the solvent comprises at least one of water, glycerin, propylene glycol, isopropanol, ethanol, and methanol. In further embodiments, the solvent comprises at least one of water at a concentration up to 99%, glycerin at a concentration up. to 20%, propylene glycol at a concentration up to 20%, ethanol at a concentration up to 99%, and methanol at a concentration up to 99%.

In certain embodiments, the viscosity-increasing agent is dextran, polyvinylpyrrolidone, hydroxyethyl cellulose, or hydroxypropyl methylcellulose. In another embodiment, the viscosity-increasing agent is hydroxyethyl cellulose at a concentration ranging from about 0.5% to about 5% or from about 1% to about 3%. In another embodiment, the viscosity-increasing agent is hydroxypropyl methylcellulose at a concentration ranging from about 1% to about 3%. In other embodiments, the viscosity-increasing agent is dextran at a concentration ranging from about 0.1% to about 5% or from about 0.5% to about 1%. In certain other embodiments, where the viscosity-increasing agent is hydroxyethyl cellulose, the composition further comprises a second viscosity-increasing agent of dextran, polyvinylpyrrolidone, or hydroxypropyl methylcellulose. In one embodiment, the second viscosity-increasing agent is polyvinylpyrrolidone. In related embodiments, the polyvinylpyrrolidone is at a concentration ranging from about 0.1% to about 5% or from about 0.5% to about 1%. In another embodiment, the second viscosity-increasing agent is hydroxypropyl methylcellulose. In related embodiments, the hydroxypropyl methylcellulose is at a concentration ranging from about 1% to about 3%. In certain other embodiments, where the viscosity-increasing agent is hydroxypropyl methylcellulose, the composition further comprises a second viscosity-increasing agent of dextran, or dextran at concentration ranging from about 0.1% to about 5% or from about 0.5% to about 1%. In still other embodiments, where the viscosity-increasing agent is hydroxypropyl methylcellulose, the composition further comprises a second viscosity-increasing agent of polyvinylpyrrolidone, or polyvinylpyrrolidone at a concentration ranging from about 0.1% to about 5% or from about 0.5% to about 1%.

In certain embodiments, the antimicrobial cationic peptide is an indolicidin or an analog or derivative thereof in any one of the aforementioned compositions. In other embodiments, the cationic peptide is at a concentration ranging from about 0.01% to about 10% or from about 0.5% to about 1.5% in any one of the aforementioned compositions. In yet other embodiments, the cationic peptide is a peptide of up to 35 amino acids, comprising one of the following sequences: 11B7CN, 11B32CN, 11B36CN, 11E3CN, 11F4CN, 11F5CN, 11F12CN, 11F17CN, 11F50CN, 11F56CN, 11F63CN, I 1F64CN, 11F66CN, 11F67CN, 11F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN in any one of the aforementioned compositions.

In still another aspect, the present invention provides a composition comprising an antimicrobial cationic peptide, a buffering agent, and a solvent. In other embodiments, the composition further comprises a humectant. In one embodiment, the humectant is sorbitol or glycerol. In another embodiment, the composition further comprises a preservative. In, one embodiment, the preservative comprises benzoic acid, benzyl alcohol, phenoxyethanol, methylparaben, propylparaben, or a combination thereof. In yet other embodiments, the composition further comprises a viscosity-increasing agent of dextran, polyvinylpyrrolidone, hydroxyethyl cellulose, or hydroxypropyl methylcellulose. In another embodiment, the viscosity-increasing agent is hydroxyethyl cellulose at a concentration ranging from about 1% to about 3%. In another embodiment, the viscosity-increasing agent is hydroxypropyl methylcellulose at a concentration ranging from about 1% to about 3%. In certain other embodiments, wherein the viscosity-increasing agent is hydroxyethyl cellulose, the composition further comprises a second viscosity-increasing agent of hydroxypropyl methylcellulose. In another embodiment, the viscosity-increasing agent is hydroxyethyl cellulose at a concentration up to about 3% and the second viscosity-increasing agent is hydroxypropyl methylcellulose at a concentration up to about 3%. In a further embodiment, the composition further comprises an acne medicament of retinoid, vitamin D3, or corticosteroid, and analogues or derivatives thereof.

In certain embodiments the solvent is water, glycerin, propylene glycol, isopropanol, ethanol, or methanol. In certain embodiments, the solvent is, glycerin at a concentration ranging from about 9% to about 11%. In another embodiment, the solvent is propylene glycol at a concentration ranging from about 9% to about 11%. In yet other embodiments, the solvent comprises at least one of water, glycerin, propylene glycol, isopropanol, ethanol, and methanol. In further embodiments, the solvent comprises at least one of water at a concentration up to 99%, glycerin at a concentration up to 20%, propylene glycol at a concentration up to 20%, ethanol at a concentration up to 99%, and methanol at a concentration up to 99%.

In certain embodiments, the buffering agent comprises a monocarboxylate or a dicarboxylate. In other embodiments, the buffering agent is acetate, fumarate, lactate, malonate, succinate, or tartrate. In yet another embodiment, the composition has a pH ranging from about 3 to about 8. In further embodiments, the buffering agent is at a concentration ranging from about 1 mM to about 200 mM or from about 4 mM to about 6 mM.

In certain embodiments, the antimicrobial, cationic peptide is an indolicidin or an analog or derivative thereof in any one of the aforementioned compositions. In other embodiments, the cationic peptide is at a concentration ranging from about 0.01% to about 10% or from. about 0.5% to about 1.5% in any one of the aforementioned compositions. In yet other embodiments, the cationic peptide is a peptide of up to 35 amino acids, comprising one of the following sequences: 11B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11 F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN in any one of the aforementioned compositions.

In yet another aspect, the present invention provides a composition comprising an antimicrobial cationic peptide at a concentration ranging from about 0.01% to about 10%; a viscosity-increasing agent of dextran, polyvinylpyrrolidone, hydroxyethyl cellulose, or hydroxypropyl methylcellulose; and a solvent of water, glycerin, propylene glycol, isopropanol, ethanol, or methanol; at a pH ranging from about 3 to about 8. In certain embodiments, the composition comprises hydroxyethyl cellulose at a concentration ranging from about 1% to about 2%. In other embodiments, the composition comprises glycerin at a concentration ranging from about 9% to about 11%. In another embodiment, the composition further comprises a buffering agent. In one embodiment, the composition further comprising the buffering agent has a pH ranging from about 3.5 to about 7. In other embodiments, the buffering agent comprises a monocarboxylate or a dicarboxylate. In yet other embodiments, the buffering agent is acetate, fumarate, lactate, malonate, succinate, or tartrate. In certain other embodiments, the buffering agent is at a concentration ranging from about 1 mM to about 200 mM or from about 4 mM to about 6 mM. In another embodiment, the composition further comprises a preservative. In one embodiment, the preservative comprises benzoic acid, benzyl alcohol, phenoxyethanol, methylparaben, propylparaben, or a combination thereof.

In certain embodiments, the antimicrobial cationic peptide is an indolicidin or an analog or derivative thereof in any one of the aforementioned compositions. In other embodiments, the cationic peptide is a peptide of up to 35 amino acids, comprising one of the following sequences: 11B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN in any one of the aforementioned compositions.

In a further aspect, the present invention provides a composition comprising (a) an antimicrobial cationic peptide wherein the cationic peptide is a peptide of up to 35 amino acids comprising one of the following: 11B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN; (b) a viscosity-increasing agent wherein the viscosity-increasing agent is hydroxyethyl cellulose at a concentration of about 1.2% to about 1.8%; (c) a buffer wherein the buffer is lactate at a concentration ranging from about 4 mM to about 6 mM; (d) a solvent wherein the solvent comprises glycerin at a concentration ranging from about 9% to about 11% and water at a concentration ranging from about 85% to about 90%; and (e) a pH ranging from about 3.5 to about 7. In certain embodiments, the cationic peptide is at a concentration ranging from about 0.8% to about 1.2%. In yet another embodiment, provided are methods to reduce microflora, or to treat or prevent an infection, at a target site, the target site may be skin, and, the skin may further comprise acne. In another embodiment, the composition may be applied to a target site to treat or prevent or ameliorate inflammation, such as inflammation associated with acne (or with an implanted or indwelling medical device).

Another aspect of the present invention is a composition, comprising (a) an antimicrobial cationic peptide wherein the cationic peptide is a peptide of up to 35 amino acids comprising one of the following: 11B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN; (b) a buffer wherein the buffer is lactate at a concentration ranging from about 4 mM to about 6 mM; (c) a solvent wherein the solvent comprises ethanol at a concentration ranging from about 45% to about 55% and water at a concentration ranging from about 44% to about 54%; and (d) a pH ranging from about 3.5 to about 7. In certain embodiments, the cationic peptide is at a concentration ranging from about 0.8% to about 1.2%. In other embodiments, the composition may further comprise an acne medicament such as retinoid, vitamin D3, or corticosteroid, and analogs or derivatives thereof. In yet another embodiment, provided are methods to reduce microflora, or to treat or prevent an infection, at a target site, the target site may be skin, and the skin may further comprise acne. In another embodiment, the composition may be applied to a target site to treat or prevent or ameliorate inflammation, such as inflammation associated with acne (or with an implanted or indwelling medical device).

In still another aspect, the present invention provides a composition comprising (a) an antimicrobial cationic peptide wherein the cationic peptide is a peptide of up to 35 amino acids comprising one of the following: 11B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN; (b) a viscosity-increasing agent wherein the viscosity-increasing agent is hydroxyethyl cellulose at a concentration of about 1.2% to about 1.8%; (c) a solvent wherein the solvent comprises glycerin at a concentration ranging from about 9% to about 11% and water at a concentration ranging from about 85% to about 90%; (d) a preservative wherein the preservative is benzoic acid at a concentration ranging from about 20 mM to about 30 mM; and (e) a pH ranging from about 3.5 to about 4.7. In certain embodiments, the cationic peptide is at a concentration ranging from about 0.8% to about 1.2%, or ranging from about 2.5% to about 3.5%. In yet another embodiment, provided are methods to reduce microflora, or to treat or prevent an infection, at a target site, the target site may be skin, and the skin may further comprise acne. In another embodiment, the composition may be applied to a target site to treat or prevent or ameliorate inflammation, such as inflammation associated with acne (or with an implanted or indwelling medical device).

In another aspect there is provided a method for reducing microflora at a target site, comprising applying to the target site a composition comprising an antimicrobial cationic peptide, a viscosity-increasing agent, and a solvent. In certain embodiments, the microflora is a prokaryotic organism, a eukaryotic organism, or a virus. In some embodiments the target site is skin and in others the skin further comprises acne. In other embodiments, the target site is a mucosa, and in still other embodiments the mucosa further comprises a nasal passage. In one embodiment the nasal passage is an anterior naris. In certain other embodiments, the method further comprises inserting a medical device at the target site before or after applying the composition. In yet another embodiment, the method further comprises applying the composition to the device prior to inserting the device at the target site. In one embodiment, the device comprises a catheter and another embodiment is a central venous catheter. In certain other embodiments, the catheter is a vascular dialysis catheter, a pulmonary artery catheter, a peritoneal dialysis catheter, or an umbilical catheter.

In a further aspect, the present invention provides a method for treating or preventing infection at a target site, comprising applying to the target site a composition comprising a cationic peptide, a viscosity-increasing agent, and a solvent. In certain embodiments, the infection is caused by a prokaryotic organism, a eukaryotic organism, or a virus. In other embodiments, the infection at a target site is associated with a medical device at the target site. In further embodiments, the method comprises applying the composition prior to or after inserting a medical device at the target. In one embodiment, the device comprises a catheter and another embodiment is a central venous catheter. In certain other embodiments, the catheter is a vascular dialysis catheter, a pulmonary artery catheter, a peritoneal dialysis catheter, or an umbilical catheter. In some embodiments the target site is skin and in others the skin further comprises acne. In other embodiments, the target site is a mucosa, and in still other embodiments the mucosa further comprises a nasal passage. In one embodiment the nasal passage is an anterior naris.

In yet another aspect there is provided a method treating or preventing inflammation at a target site, comprising applying to the target site a composition comprising a cationic peptide, a viscosity-increasing agent, and a solvent. In one embodiment, the target site further comprises an infection. In a further embodiment, the inflammation at the target site is associated with a medical device. In further embodiments, the method comprises applying the composition prior to or after inserting a medical device at the target. In one embodiment, the device comprises a catheter and another embodiment is a central venous catheter. In certain other embodiments, the catheter is a vascular dialysis catheter, a pulmonary artery catheter, a peritoneal dialysis catheter, or an umbilical catheter. In some embodiments the target site is skin and in others the skin further comprises acne. In other embodiments, the target site is a mucosa, and in still other embodiments the mucosa further comprises a nasal passage. In one embodiment the nasal passage is an anterior naris.

In yet another aspect, the invention provides a method for ameliorating inflammation at a target site, comprising applying to the target site a composition comprising a cationic peptide, a viscosity-increasing agent, and a solvent. In one embodiment, the target site further comprises an infection. In a further embodiment, the inflammation at the target site is associated with a medical device. In further embodiments, the method comprises applying the composition prior to or after inserting a medical device at the target. In one embodiment, the device comprises a catheter and another embodiment is a central venous catheter. In certain other embodiments, the catheter is a vascular dialysis catheter, a pulmonary artery catheter, a peritoneal dialysis catheter, or an umbilical catheter. In some embodiments the target site is skin and in others the skin further comprises acne. In other embodiments, the target site is a mucosa, and in still other embodiments the mucosa further comprises a nasal passage. In one embodiment the nasal passage is an anterior naris.

These and other aspects of the present invention will become evident upon reference to the following detailed description and attached drawings. In addition, various references are set forth herein which describe in more detail certain procedures or compositions, and are therefore incorporated by reference in their entirety.

DETAILED DESCRIPTION OF THE INVENTION

Figure 1:
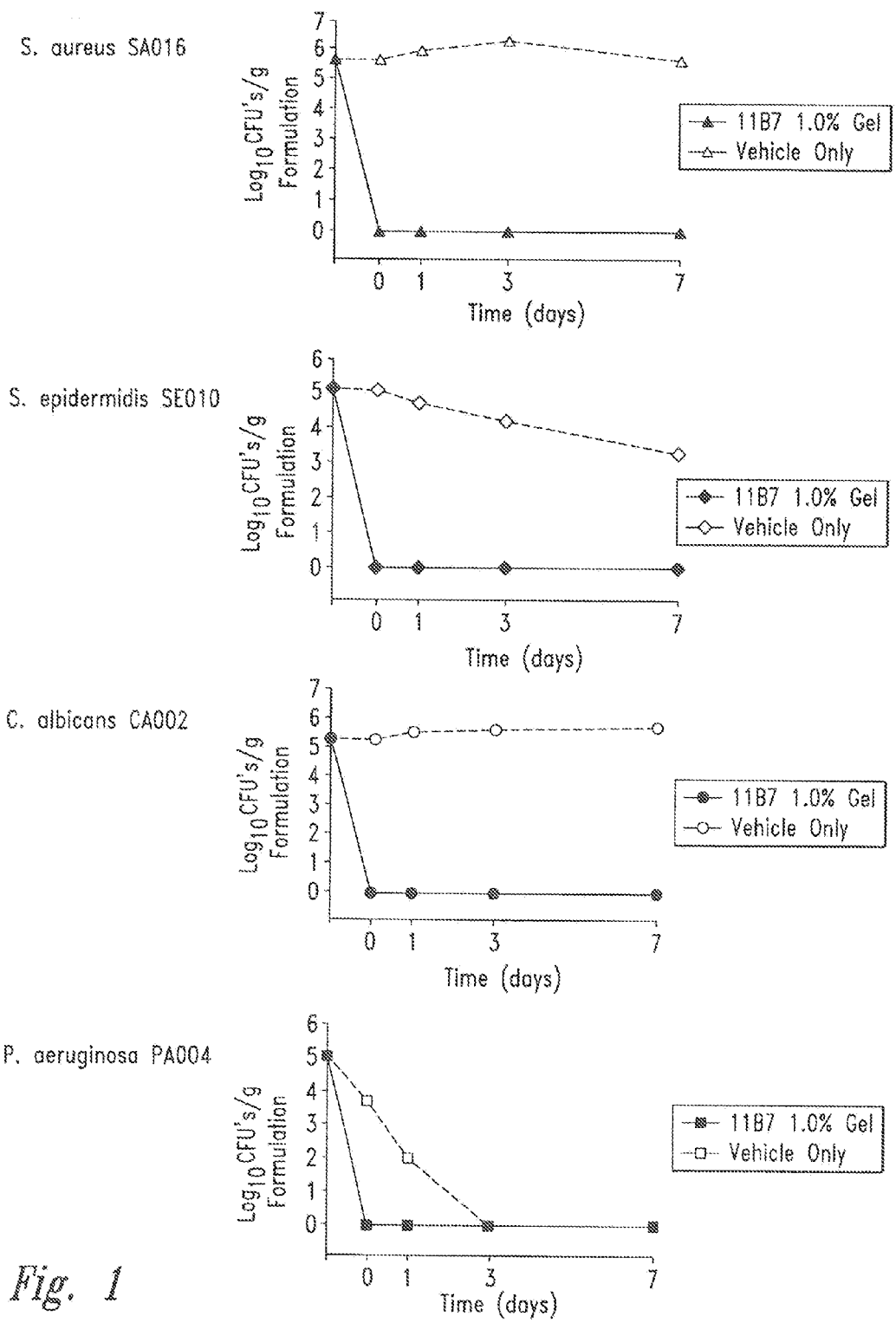
FIG. 1 shows the results of a bacterial challenge test of an antimicrobial cationic peptide (1%, gel) formulation, illustrating the antimicrobial effectiveness of the formulation when seeded with a large inoculum of various bacteria and fungi.
Figure 2:
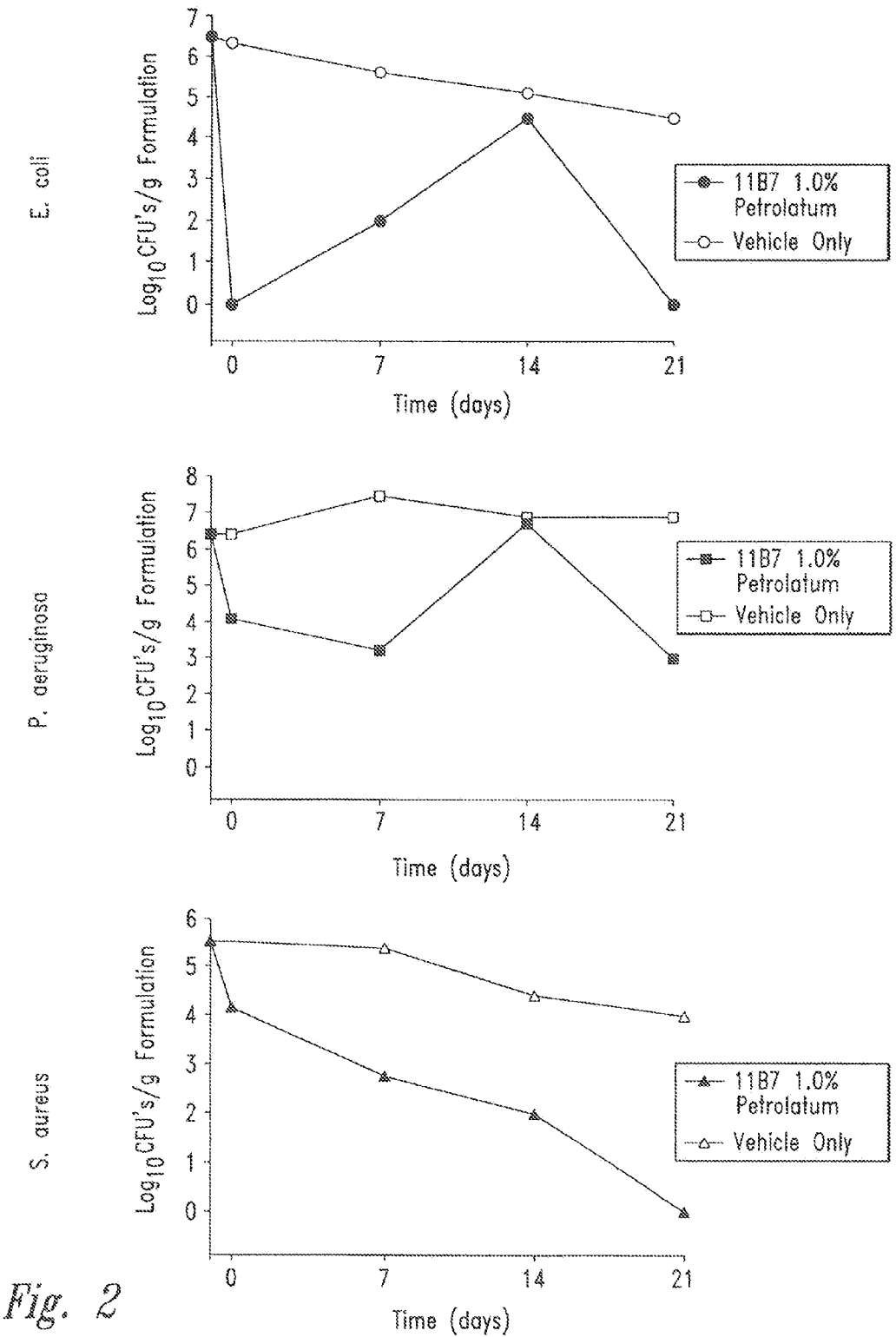
FIG. 2 shows the results of a bacterial challenge test of an antimicrobial cationic peptide (1%, petrolatum) formulation illustrating the antimicrobial effectiveness of the formulation.

As noted above, the present invention provides compositions and methods for using antimicrobial cationic peptides to treat and/or prevent infectious diseases. The invention, therefore, relates generally to the surprising discovery that antimicrobial cationic peptides may be formulated at a clinically relevant concentration to maximize their in vivo and in vitro stability, release half-life, and antimicrobial activity. According to the present invention, formulations of antimicrobial cationic peptides (e.g., indolicidins and derivatives or analogs thereof), as described herein, provide novel and useful compositions for use in a variety of therapeutic settings (e.g., in the treatment and prevention of nosocomial infections, acne, and infections associated with intravascular penetration, such as in the use of hypodermic needles and catheters). Discussed in more detail below are cationic peptides suitable for use within the present invention, as well as representative formulations and therapeutic uses. Any concentration ranges recited herein are to be understood to include concentrations of any integer within the range and fractions thereof, such as one tenth and one hundredth of an integer, unless otherwise indicated.

A. Antimicrobial Cationic Peptides

The present invention is directed generally to antimicrobial cationic peptides, which may be produced by a variety of methods (e.g., chemical or recombinant) for use in the formulations as described herein. Suitable antimicrobial cationic peptides include, but are not limited to, naturally occurring cationic peptides, which have been isolated, and derivatives or analogs thereof. An "isolated peptide, polypeptide, or protein" is an amino acid sequence that is essentially free from contaminating cellular components, such as carbohydrate, lipid, nucleic acid (DNA or RNA), or other proteinaceous impurities associated with the polypeptide in nature. Preferably, the isolated polypeptide is sufficiently pure for therapeutic use at the desired dose.

An antimicrobial cationic peptide of the present, invention may be a recombinant peptide or a synthetic peptide, and is preferably a recombinant peptide. Peptides may be synthesized by standard chemical methods, including synthesis by automated procedure. In general, peptide analogues are synthesized based on the standard solid-phase Fmoc protection strategy with HATU as the coupling agent. The peptide is cleaved from the solid-phase resin with trifluoroacetic acid containing appropriate scavengers, which also deprotects side chain functional groups. Crude peptide is further purified using preparative reversed-phase chromatography. Other purification methods, such as partition chromatography, gel filtration, gel electrophoresis, or ion-exchange chromatography may be used. Other synthesis techniques, known in the art, such as the tBoc protection strategy, or use of different coupling reagents or the like can be employed to produce equivalent peptides. Peptides may be synthesized as a linear molecule or as branched molecules. Branched peptides typically contain a core peptide that provides a number of attachment points for additional peptides. Lysine is most commonly used for the core peptide because it has one carboxyl functional group and two (alpha and epsilon) amine functional groups. Other diamino acids can also be used. Preferably, either two or three levels of geometrically branched lysines are used; these cores form a tetrameric and octameric core structure, respectively (Tam, *Proc. Natl. Acad. Sci. USA* 85:5409, 1988).

An antimicrobial cationic peptide is a peptide that typically exhibits a positive charge at a pH ranging from about 3 to about 10 (i.e., has an isoelectric point of at least about 9), and contains at least one basic amino acid (e.g., arginine, lysine, histidine). In, addition, an antimicrobial cationic peptide generally comprises an amino acid sequence having a molecular mass of about 0.5 kDa (i.e., approximately five amino acids in length) to about 10 kDa (i.e., approximately 100 amino acids in length), or a molecular mass of any integer, or fraction thereof (including a tenth and one hundredth of an integer), ranging from about 0.5 kDa to about 10 kDa. Preferably, an antimicrobial cationic peptide has a molecular mass ranging from about 0.5 kDa to about 5 kDa (i.e., approximately from about 5 amino acids to about 45 amino acids in length), more preferably from about 1 kDa to about 4 kDa (i.e., approximately from about 10 amino acids to about 35 amino acids in length), and most preferably from about 1 kDa to about 2 kDa (i.e., approximately from about 10 amino acids to about 18 amino acids in length). In another preferred embodiment, the antimicrobial cationic peptide is part of a larger peptide or polypeptide sequence having, for example, a total of up to 100 amino acids, more preferably up to 50 amino acids, even more preferably up to 35 amino acids, and most preferably up to 15 amino acids. The present invention contemplates an antimicrobial cationic peptide having an amino acid sequence of 5 to 100 amino acids, with the number of amino acids making up the peptide sequence comprising any integer in that range. An antimicrobial cationic peptide may exhibit antibacterial activity, anti-endotoxin activity, antifungal activity, antiparasite activity, antiviral activity, anticancer activity, anti-inflammatory activity, wound healing activity, and synergistic activity with other peptides or antimicrobial compounds, or a combination thereof.

Exemplary antimicrobial peptides include, but are not limited to, cecropins, normally made by lepidoptera (Steiner et al., Nature 292:246, 1981) and diptera (Merrifield et at, Ciba Found. Symp. 186:5, 1994), by porcine intestine (Lee et al., Proc. Nat'l Acad. Sci. USA 86:9159, 1989), by blood cells of a marine protochordate (Zhao et al., FEBS Lett. 412:144, 1997); synthetic analogs of cecropin A, melittin, and cecropin-melittin chimeric peptides (Wade et al., Int. J. Pept. Protein Res. 40:429, 1992); cecropin B analogs (Jaynes et al., Plant Sci. 89:43, 1993); chimeric cecropin A/B hybrids (Düring, Mol. Breed. 2:297, 1996); magainins (Zasloff, Proc. Nat'l Acad. Sci USA 84:5449, 1987); cathelin-associated antimicrobial peptides from leukocytes of humans, cattle, pigs, mice, rabbits, and sheep (Zanetti et al., FEBS Lett. 374:1, 1995); vertebrate defensins, such as human neutrophil defensins [HNP 1-4]; paneth cell defensins of mouse and human small intestine (Oulette and Selsted, FASEB J. 10:1280, 1996; Porter et al., Infect. Immun. 65:2396, 1997); vertebrate β-defensins, such as HBD-1 of human epithelial cells (Zhao et at, FEBS Lett. 368:331, 1995); HBD-2 of inflamed human skin (Harder et al., Nature 387:861, 1997); bovine β-defensins (Russell et al., Infect. Immun. 64:1565, 1996); plant defensins, such as Rs-AFP1 of radish seeds (Fehlbaum et al., J. Biol. Chem. 269:33159, 1994); α- and β-thionins (Stuart et al., Cereal Chem. 19:288, 1942; Bohlmann and Apel, Annu. Rev. Physiol. Plant Mol. Biol. 42:227, 1991); γ-thionins (Broekaert et al., Plant Physiol. 108:1353, 1995); the anti-fungal drosomycin (Fehlbaum et al., J. Biol. Chem. 269:33159, 1994); apidaecins, produced by honey bee, bumble bee, cicada killer, hornet, yellow jacket, and wasp (Casteels et al., J. Biol. Chem. 269:26107, 1994; Levashina et al., Eur. J. Biochem. 233:694, 1995); cathelicidins, such as indolicidin and derivatives or analogues thereof from bovine neutrophils (Falla et al., J. Biol. Chem. 277: 19298, 1996); bacteriocins, such as nisin (Delves-Broughton et al., Antonie van Leeuwenhoek J. Microbiol. 69:193, 1996); and the protegrins and tachyplesins, which have antifungal, antibacterial, and antiviral activities (Tamamura et al., Biochim. Biophys. Acta 1163:209, 1993; Aumelas et al., Eur. J. Biochem. 237:575, 1996; Iwanga et al., Ciba Found. Symp. 186:160, 1994).

In certain embodiments, preferred antimicrobial cationic peptides of the present invention are indolicidins or analogs or derivatives thereof (see Table 2 of Example 1). Natural indolicidins may be isolated from a variety of organisms, and, for example, the indolicidin isolated from bovine neutrophils is a 13 amino acid peptide, which is tryptophan-rich and amidated at the C-terminus (see Selsted et al., J. Biol. Chem. 267:4292, 1992). As noted above, a preferred indolicidin or analog or derivative thereof comprises 5 to 45 amino acids, more preferably 7 to 35 amino acids, even more preferably 8 to 25 amino acids, and most preferably 10 to 14 amino acids (see, e.g., Table 2). The indolicidins or analogs or derivatives thereof of the present invention may be used at a concentration ranging from about 0.01% to about 10%, preferably from about 0.5% to about 5%, and more preferably from either about 1% to about 3% or about 4% to about 6%, depending on the intended use and formulation ingredients (where "about" is ±10% of the indicated value). In certain embodiments, the antimicrobial cationic peptide is an indolicidin or an analog or derivative thereof in any one of the aforementioned compositions. In preferred embodiments, the antimicrobial cationic peptide is a peptide of up to 35 amino acids, comprising one of the following sequences: 11 B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11 F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN, which may be used in any one of the compositions described herein.

An antimicrobial cationic peptide of the present invention may be an analog or derivative thereof. As used herein, the terms "derivative" and "analog" when referring to an antimicrobial cationic peptide, polypeptide, or fusion protein, refer to any antimicrobial cationic peptide, polypeptide, or fusion protein that retain essentially the same (at least 50%, and preferably greater than 70, 80, or 90%) or enhanced biological function or activity as such natural peptide, as noted above. The biological function or activity of such analogs and derivatives can be determined using standard methods (e.g., antimicrobial, anti-inflammatory, DNA and/or protein synthesis inhibitor), such as with the assays described herein. For example, an analog or derivative may be a proprotein that can be activated by cleavage to produce an active antimicrobial cationic peptide. Alternatively, a cationic peptide analog or derivative thereof can be identified by the ability to specifically bind anti-cationic peptide antibodies.

A cationic peptide analog or derivative may have, for example, one or more deletion, insertion, or modification of any amino acid residue, including the N- or C-terminal amino acids. Within the scope of this invention are modified antimicrobial cationic peptides, such as, for example, peptides having an acetylated, acylated, acryloylated, alkylated, glycosylated (e.g., glucosylated), PEGylated, myristylated, and the like N-terminal amino acid modification; having an esterified, amidated, homoserine/homoserine lactone, or caprolactam C-terminal amino acid modification; or having a polyalkylene glycol (e.g., polyethylene glycol) conjugated to any free amino group. A preferred modification of the C-terminal amino acid is amidation.

An analog or derivative may also be an antimicrobial cationic peptide fusion protein. Fusion proteins, or chimeras, include fusions of one or more antimicrobial cationic peptides, and fusions of cationic peptides with non-cationic peptides. Additionally, the peptide may be modified to form a polymer-modified peptide. The peptides may also be labeled, such as with a radioactive label, a fluorescent label, a mass spectrometry tag, biotin, and the like.

Another example of an analog or derivative includes an antimicrobial cationic peptide that has one or more conservative amino acid substitutions, as compared with the amino acid sequence of a naturally occurring cationic peptide. Among the common amino acids, a "conservative amino acid substitution" is illustrated, for example, by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine, or a combination thereof. Furthermore, an analog or derivative of a cationic peptide may include, for example, non-protein amino acids, such as precursors of normal amino acids (e.g., homoserine and diaminopimelate), intermediates in catabolic pathways (e.g., pipecolic acid and D-enantiomers of normal amino acids), and amino acid analogs (e.g., azetidine-2-carboxylic acid and canavanine).

The amino acid designations are herein set forth as either the standard one- or three-letter code. Unless otherwise indicated, a named amino acid refers to the L-enantiomer. Polar amino acids include asparagine (Asp or N) and glutamine. (Gln or Q); as well as basic amino acids such as arginine (Arg or R), lysine (Lys or K), histidine (His or H), and derivatives thereof; and acidic amino acids such as aspartic acid (Asp or D) and glutamic acid (Glu or E), and derivatives thereof. Hydrophobic amino acids include tryptophan (Trp or W), phenylalanine (Phe or F), isoleucine (Ile or I), leucine (Leu or L), methionine (Met or M), valine (Val or V), and derivatives thereof; as well as other non-polar amino acids such as glycine (Gly or G), alanine (Ala or A), proline (Pro or P), and derivatives thereof. Amino acids of intermediate polarity include serine (Ser or S), threonine (Thr or T), tyrosine (Tyr or Y), cysteine (Cys or C), and derivatives thereof. A capital letter indicates an L-enantiomer amino acid; a small letter indicates a D-enantiomer amino acid. For example, some modified amino acids may include 2,3-diamino butyric acid, 3- or 4-mercaptoproline derivatives, $N^5$-acetyl-$N^5$-hydroxy-L-ornitine, and $\alpha$-N-hydroxyamino acids. An antimicrobial cationic peptide analog or derivative thereof may include any one or combination of the above-noted alterations to the natural peptide, or any other modification known in the art.

The indolicidins or analogs or derivatives thereof of the present invention may be used individually, or may be used in combination with one or more different indolicidins or analogs or derivatives thereof, with one or more antimicrobial cationic peptides, and one or more conventional antimicrobial agents, as described herein. Thus, synergistic combinations of an antimicrobial cationic peptide and an antimicrobial agent may permit a reduction in the dosage of one or both agents in order to achieve a similar or improved therapeutic effect. This would allow the use of smaller doses and, therefore, would decrease the potential incidence of toxicity (e.g., from aminoglycosides) and lowering costs of expensive antimicrobials (e.g., vancomycin). Concurrent or sequential administration of an antimicrobial cationic peptide formulation and an antimicrobial agent composition is expected to provide more effective treatment of infections caused by a variety of microorganisms (e.g., bacteria, viruses, fungi, and parasites). In particular, successful treatment or prevention of infectious disease can be achieved by using the antimicrobial cationic peptides and antimicrobial agents at doses below what is normally a therapeutically effective dose when these antimicrobials are used individually. Alternatively, the antibiotic agent and antimicrobial cationic peptide formulation can be administered using a normally effective therapeutic dose for each antimicrobial, but wherein the combination of the two agents provides even more potent effects.

As noted above, the preferred antimicrobial cationic peptides may be used in a synergistic combination with other known antimicrobial agents. Antibacterial agents include, but are not limited to, penicillins, cephalosporins, carbacephems, cephamycins, carbapenems, monobactams, aminoglycosides, glycopeptides, quinolones, tetracyclines, macrolides, and fluoroquinolones. Examples of antibiotic agents include, but are not limited to, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefinetazole (CAS Registry No.: 56796-20-4); Cefotetan (CAS Registry No.: 69712-56-7); Cefprozil (CAS Registry. No.: 92665-29-7); Lincomycin (CAS Registry No.: 154-21-2); Linezolid (CAS Registry No.: 165800-03-3); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry. No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

The antimicrobial cationic peptide may also be used in combination with anti-fungal agents. Exemplary anti-fungal agents include, but are not limited to, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

The antimicrobial cationic peptide may also be used in combination with anti-viral agents. Exemplary anti-viral agents include, but are not limited to, amantadine hydrochloride, rimantadin, acyclovir, famciclovir, foscarnet, ganciclovir sodium, idoxuridine, ribavirin, sorivudine, trifluridine, valacyclovir, vidarabin, didanosine, stavudine, zalcitabine, zidovudine, interferon alpha, and edoxudine.

The antimicrobial cationic peptide may also be used in combination with anti-parasitic agents. Exemplary anti-parasitic agents include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

In another aspect, antibodies may be generated to a specific antimicrobial cationic peptide and analogue or derivative thereof using multiple antigenic peptides (MAPs) that contain approximately eight copies of the peptide linked to a small non-immunogenic peptidyl core to form an immunogen (see, in general, *Antibodies: A Laboratory Manual*, Harlow and Lane (eds.), Cold Spring Harbor Laboratory Press, 1988). Alternatively, the target peptide may be conjugated to bovine serum albumin (BSA), ovalbumin, or another suitable conjugate. The MAP or peptide conjugate is injected subcutaneously into rabbits or into mice or other rodents, where they may have sufficiently long half-lives to facilitate antibody production. After twelve weeks, blood samples are taken and serum is separated for testing in an ELISA assay against the original peptide, with a positive result indicating the presence of antibodies specific to the target peptide. This serum can then be stored and used in ELISA assays to specifically measure the amount of the specific antimicrobial cationic peptide and/or analog or derivative thereof. Alternatively, other standard methods of antibody production may be employed, for example generation of monoclonal antibodies.

Within the context of the present invention, antibodies are understood to include, inter alia, monoclonal antibodies, polyclonal antibodies, anti-idiotypic antibodies, and antibody fragments (e.g., Fab, and $F(ab')_2$, $F_v$ variable regions, or complementarity determining regions). Antibodies are generally accepted as specific against cationic peptides, such as indolicidin and analogs or derivatives thereof, if they bind with a $K_d$ of greater than or equal to $10^{-7}$ M, preferably greater than of equal to $10^{-8}$ M, and more preferably greater than of equal to $10^{-9}$ M. The affinity of a monoclonal antibody or binding partner may be readily determined by one of ordinary skill in the art (see, e.g., Scatchard, *Ann. N.Y. Acad. Sci.* 51:660-672, 1949). Once suitable antibodies have been identified, they may be isolated or purified by many techniques well known to those of ordinary skill in the art.

Monoclonal antibodies may also be readily generated from hybridoma cell lines using conventional techniques (see U.S. Pat. Nos. RE 32,011, 4,902,614, 4,543,439, and 4,411,993; see also *Antibodies: A Laboratory Manual*, 1988). Briefly, within one embodiment, a subject animal, such as a rat or mouse, is injected with a peptide of choice. The peptide is generally administered in an emulsion with an adjuvant, such as Freund's complete or incomplete adjuvant, which is intended to increase the immune response. The animal is generally boosted at least once prior to harvest of the spleen and/or lymph nodes and immortalization of those cells. Various immortalization techniques, such as mediated by Epstein-Barr virus or fusion to produce a hybridoma, may be used. In a preferred embodiment, immortalization occurs by fusion with a suitable myeloma cell line to create a hybridoma that secretes monoclonal antibody. Suitable myeloma lines include, for example, NS-1 (ATCC No. TIB 18), and P3X63-Ag 8.653 (ATCC No. CRL 1580). The preferred fusion partners do not express endogenous antibody genes. After about seven days, the hybridomas may be screened for the presence of antibodies that are reactive against an antimicrobial cationic peptide and analog or derivative thereof. A wide variety of assays may be utilized (see *Antibodies: A Laboratory Manual*, 1988).

Other techniques known in the art may be utilized to construct monoclonal antibodies (see Huse et al., *Science* 246: 1275-1281, 1989; Sastry et al., *Proc. Natl. Acad. Sci. USA* 86:5728-5732, 1989; Alting-Mees et al., *Strategies in Molecular Biology* 3:1-9, 1990; describing recombinant techniques). These techniques include cloning heavy and light chain immunoglobulin cDNA in suitable vectors, such as λImmunoZap(H) and λImmunoZap(L). These recombinants may be screened individually or co-expressed to form Fab fragments or antibodies (see Huse et al., supra; Sastry et al., supra). Positive plaques may subsequently be converted into non-lytic plasmids to allow high-level expression of monoclonal antibody fragments in a host, such as *E. coli*.

Similarly, portions or fragments of antibodies, such as Fab and Fv fragments, may also be constructed utilizing conventional enzymatic digestion or recombinant DNA techniques to yield isolated variable regions of an antibody. Within one embodiment, the genes that encode the variable region from a hybridoma producing a monoclonal antibody of interest are amplified using nucleotide primers for the variable region. In addition, techniques may be utilized to change a "murine" antibody to a "human" antibody, without altering the binding specificity of the antibody to the antimicrobial cationic peptide and analog or derivative thereof.

B. Nucleic Acids Encoding Antimicrobial Cationic Peptides

Nucleic acid molecules encoding cationic peptides may be isolated from natural sources, may be obtained by automated synthesis of nucleic acid molecules, or may be obtained by using the polymerase chain reaction (PCR) with oligonucleotide primers having nucleotide sequences that are based upon known nucleotide sequences of antimicrobial cationic peptide genes. In the latter approach, a cationic peptide gene is synthesized using mutually priming oligonucleotides (see, for example, Ausubel et al. (eds.), *Short Protocols in Molecular Biology*, $3^{rd}$ *Edition*, pages 8-8 to 8-9, John Wiley & Sons, 1995, herein after referred to as "Ausubel (1995)"). Established techniques using the polymerase chain reaction provide the ability to synthesize DNA molecules of at least two kilobases in length (Adang et al., *Plant Molec. Biol.* 21:1131, 1993; Bambot et al., *PCR Methods and Applications* 2:266, 1993; Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263-268, Humana Press, Inc., 1993; Holowachuk et al., *PCR Methods Appl.* 4:299, 1995).

As noted above, the present invention contemplates analogs or derivatives of natural cationic peptides, which analogs or derivatives may be recombinantly produced by the presently described methods. Nucleotide sequences encoding conservative amino acid analogs or derivatives can be obtained, for example, by oligonucleotide-directed mutagenesis, linker-scanning mutagenesis, mutagenesis using the polymerase chain reaction, and the like (see Ausubel, 1995, at page 8-10 through page 8-22; and McPherson (ed.), *Directed Mutagenesis: A Practical Approach*, IRL Press, 1991).

Although one objective in constructing a cationic peptide variant may be to improve its activity, it may also be desirable to alter the amino acid sequence of a naturally occurring cationic peptide to enhance its production in a recombinant host cell. The presence of a particular codon may have an adverse effect on expression in a particular host; therefore, a DNA sequence encoding the desired cationic peptide is optimized for a particular host system, such as prokaryotic or eukaryotic cells. For example, a nucleotide sequence encoding a radish cationic peptide may include, a codon that is commonly found in radish, but is rare for *E. coli*. The presence of a rare codon may have an adverse effect on protein levels when the radish cationic peptide is expressed in recombinant *E. coli*. Methods for altering nucleotide sequences to alleviate the codon usage problem are well known to those of skill in, the art (see, e.g., Kane, *Curr. Opin. Biotechnol.* 6:494, 1995; Makrides, *Microbiol. Rev.* 60:512, 1996; and Brown (Ed.), *Molecular Biology LabFax*, BIOS Scientific Publishers, Ltd., 1991, which provides a Codon Usage Table at page 245 through page 253).

Peptides may be synthesized by recombinant techniques (see e.g., U.S. Pat. No. 5,593,866) and a variety of host systems are suitable for production of the cationic peptides and analogues or derivatives thereof, including bacteria (e.g., *E. coli*), yeast (e.g., *Saccharomyces cerevisiae*), insect (e.g., Sf9), and mammalian cells (e.g., CHO, COS-7). Many expression vectors have been developed and are available for each of these hosts. Generally, vectors that are functional in bacteria are used in this invention. However, at times, it may be preferable to have vectors that are functional in other hosts. Vectors and procedures for cloning and expression in *E. coli* are discussed herein and, for example, in Sambrook et al. (*Molecular Cloning: A Laboratory Manual*, Cold Spring Harbor Laboratory Press, Cold Spring Harbor, N.Y., 1987) and in Ausubel et al., 1995.

A DNA sequence encoding a cationic peptide is introduced into an expression vector appropriate for the host. In preferred embodiments, the gene is cloned into a vector to create a fusion protein. The fusion partner is chosen to contain an anionic region, such that a bacterial host is protected from the toxic effect of the peptide. This protective region effectively neutralizes the antimicrobial effects of the peptide and also may prevent peptide degradation by host proteases. The fusion partner (carrier protein) of the invention may further function to transport the fusion peptide to inclusion bodies, the periplasm, the outer membrane, or the extracellular environment. Carrier proteins suitable in the context of this invention specifically include, but are not limited to, glutathione-S-transferase (GST), protein A from *Staphylococcus aureus*, two synthetic IgG-binding domains (ZZ) of protein A, outer membrane protein F, β-galactosidase (lacZ), and various products of bacteriophage λ and bacteriophage T7. From the teachings provided herein, it is apparent that other proteins may be used as carriers. Furthermore, the entire carrier protein need not be used, as long as the protective anionic region is present. To facilitate isolation of the peptide sequence, amino acids susceptible to chemical cleavage (e.g., CNBr) or enzymatic cleavage (e.g., V8 protease, trypsin) are used to bridge the peptide and fusion partner. For expression in *E. coli*, the fusion partner is preferably a normal intracellular protein that directs expression toward inclusion body formation. In such a case, following cleavage to release the final product, there is no requirement for renaturation of the peptide. In the present invention, the DNA cassette, comprising, fusion partner and peptide gene, may be inserted into an expression vector, which can be a plasmid, virus or other vehicle known in the art. Preferably, the expression vector is a plasmid that contains an inducible or constitutive promoter to facilitate the efficient transcription of the inserted DNA sequence in the host. Transformation of the host cell with the recombinant DNA may be carried out by $Ca^{++}$-mediated techniques, by electroporation, or other methods well known to those skilled in the art.

Briefly, a DNA fragment encoding a peptide is derived from an existing cDNA or genomic clone or synthesized. A convenient method is amplification of the gene from a single-stranded template. The template is generally the product of an automated oligonucleotide synthesis. Amplification primers are derived from the 5' and 3' ends of the template and typically incorporate restriction sites chosen with regard to the cloning site of the vector. If necessary, translational initiation and termination codons can be engineered into the primer sequences. The sequence encoding the protein may be codon-optimized for expression in the particular host. Thus, for example, if the analogue fusion protein is expressed in bacteria, codons are optimized for bacterial usage. Codon optimization is accomplished by automated synthesis of the entire gene or gene region, ligation of multiple oligonucleotides, mutagenesis of the native sequence, or other techniques known to those in the art.

Within a preferred embodiment, the vector is capable of replication in bacterial cells. Thus, the vector may contain a bacterial origin of replication. Preferred bacterial origins of replication include f1-ori and col E1 ori, especially the ori derived from pUC plasmids. Low copy number vectors (e.g., pPD100) may also be used, especially when the product is deleterious to the host. The plasmids also preferably include at least one selectable marker that is functional in the host. A selectable marker gene confers a phenotype on the host that allows transformed cells to be identified and/or selectively grown. Suitable selectable marker genes for bacterial hosts include the chloroamphenicol resistance gene ($Cm^r$), ampicillin resistance gene ($Amp^r$), tetracycline resistance gene ($Tc^r$) kanamycin resistance gene ($Kan^r$), and others known in the art. To function in selection, some markers may require a complementary deficiency in the host. The vector may also contain a gene coding for a repressor protein, which is capable of repressing the transcription of a promoter that contains a repressor binding site. Altering the physiological conditions of the cell can depress the promoter. For example, a molecule may be added that competitively binds the repressor, or the temperature of the growth media may be altered. Repressor proteins include, but are not limited to the *E. coli* lacI repressor (responsive to induction by IPTG), the temperature sensitive $\lambda cI857$ repressor, and the like.

At minimum, the expression vector should contain a promoter sequence. However, other regulatory sequences may also be included. Such sequences include an enhancer, ribosome binding site, transcription termination signal sequence, secretion signal sequence, origin of replication, selectable marker, and the like. The regulatory sequences are operably linked with one another to allow transcription and subsequent translation. In preferred aspects, the plasmids used herein for expression include a promoter designed for expression of the proteins in bacteria. Suitable promoters, including both constitutive and inducible promoters, are widely available and are well known in the art. Commonly used promoters for expression in bacteria include promoters from T7, T3, T5, and SP6 phages, and the trp, lpp, and lac operons. Hybrid promoters (see, U.S. Pat. No. 4,551,433), such as tac and trc, may also be used. Examples of plasmids for expression in bacteria include the pET expression vectors pET3a, pET 11a, pET 12a-c, and pET 15b (see U.S. Pat. No. 4,952,496; available from Novagen, Madison, Wis.). Low copy number vectors (e.g., pPD100) can be used for efficient overproduction of peptides deleterious to the *E. coli* host (Dersch et al., *FEMS Microbiol. Lett.* 123: 19, 1994). Bacterial hosts for the T7 expression vectors may contain chromosomal copies of DNA encoding T7 RNA polymerase operably linked to an inducible promoter (e.g., lacUV promoter; see, U.S. Pat. No. 4,952, 496), such as found in the *E. coli* strains HMS174(DE3) pLysS, BL21(DE3)pLysS, HMS174(DE3) and BL21(DE3).

T7 RNA polymerase can also be present on plasmids compatible with the T7 expression vector. The polymerase may be under control of a lambda promoter and repressor (e.g., pGP1-2; Tabor and Richardson, *Proc. Natl. Acad. Sci. USA* 82: 1074, 1985).

In some aspects, the sequence of nucleotides encoding the peptide also encodes a secretion signal, such that the resulting peptide is synthesized as a precursor protein (i.e., proprotein), which is subsequently processed and secreted. The resulting secreted peptide or fusion protein may be recovered from the periplasmic space or the fermentation medium. Sequences of secretion signals suitable for use are widely available and are well known (von Heijne, *J. Mol. Biol.* 184:99-105, 1985).

The peptide product is isolated by standard techniques, such as affinity, size exclusion, or ionic exchange chromatography, HPLC and the like. An isolated peptide should preferably show a major band by Coomassie blue stain of SDS-PAGE, which is preferably at least 75%, 80%, 90%, or 95% of the purified peptide, polypeptide, or fusion protein.

C. Testing Antimicrobial Cationic Peptides Analogs and Derivatives

Antimicrobial cationic peptides, and analogs or derivatives thereof, of the present invention are assessed, either alone or in combination with, an antimicrobial agent or another analog, for their potential as antibiotic therapeutic agents using a series of assays. Preferably, all peptides are initially assessed in vitro, the most promising candidates are selected for further assessment in vivo, and then candidates are selected for pre-clinical studies. The in vitro assays include measurement of antibiotic activity, toxicity, solubility, pharmacology, secondary structure, liposome permeabilization and the like. In vivo assays include assessment of efficacy in animal models, antigenicity, toxicity, and the like. In general, in vitro assays are initially performed, followed by in vivo assays.

Generally, cationic peptides are initially tested for (1) antimicrobial activity in vitro; (2) in vitro toxicity to normal mammalian cells; and (3) in vivo toxicity in an animal model. Cationic peptides that have some antimicrobial activity are preferred, although such activity may not be necessary for enhancing the activity of an antibiotic agent. Also, for in vivo use, peptides should preferably demonstrate acceptable toxicity profiles, as, measured by standard procedures, where lower toxicity is preferred. Additional assays may be performed to demonstrate that the peptide is not immunogenic and to examine antimicrobial activity in vivo.

1. In vitro Assays

Cationic peptides, including indolicidin analogues, are assayed by, for example, an agarose dilution MIC assay, a broth dilution, time-kill assay, or equivalent methods. Antimicrobial activity is measured as inhibition of growth or killing of a microorganism (e.g., bacteria, fungi).

Briefly, a candidate antimicrobial cationic peptide in Mueller Hinton broth supplemented with calcium, and magnesium is mixed with molten agarose. Other broths and agars may be used as long as the peptide can freely diffuse through the medium. The agarose is poured into petri dishes or wells, allowed to solidify, and a test strain is applied to the agarose plate. The test strain is chosen, in part, on the intended application of the peptide. Thus, by way of example, if an indolicidin or analog or derivative thereof with activity against *S. aureus* is desired, a *S. aureus* strain is used. It may be desirable to assay the candidate antimicrobial cationic peptide on several strains and/or on clinical isolates of the test species. Plates are incubated overnight and inspected visually for bacterial growth. A minimum inhibitory concentration (MIC) of a cationic peptide is the lowest concentration of peptide that completely inhibits growth of the organism. Peptides that exhibit good activity against the test strain, or group of strains, typically having an MIC of less than or equal to 16 μg/ml are selected for further testing. Preferred antimicrobial cationic peptides or analogs or derivatives thereof may be microbicidal or microbistatic.

Alternatively, time kill curves can be used to determine the difference in growth (e.g., bacterial colony counts) over a set time period, typically 24 hours. Briefly, a suspension of organisms at a known concentration is prepared and a candidate peptide is added. Aliquots of the suspension are removed at set times, diluted, plated on medium, incubated, and counted. MIC is measured as the lowest concentration of peptide that completely inhibits growth of the organism and, in general, lower MIC values are preferred.

Solubility of the peptide in a solvent, broth, or co-solvent system as described herein is an additional parameter that may be examined. Several different assays may be used, such as appearance in buffer. Briefly, a candidate antimicrobial cationic peptide or analog or derivative thereof may be contacted with a solvent, broth, or co-solvent system, and the appearance evaluated according to a scale that ranges from (a) clear, no precipitate, (b) light, diffuse precipitate, to (c) cloudy, heavy precipitate. In general, less precipitate is more desirable, but some precipitate may be acceptable. To assess the level of solubility, for example, a person having ordinary skill in the art may inspect the combination visually, or a variety of spectrophotometric techniques may be used, such as by U.V. or visible light absorbance at the appropriate wavelength.

Additional in vitro assays may be carried out to assess the potential of a candidate peptide or analog or derivative thereof as a therapeutic agent. Such assays include peptide solubility in formulations, pharmacology and stability in blood or plasma, serum protein binding, analysis of secondary structure (e.g., by circular dichroism), liposome permeabilization, and bacterial membrane permeabilization. In general, a preferred embodiment includes a candidate peptide analog or derivative thereof that is soluble, is active in biological fluids, is stable, and has generally greater antimicrobial activity than the natural peptide (e.g., indolicidin).

2. In vivo Assays

Peptides and analogs or derivative thereof, selected on the basis of the results from the in vitro assays can be further tested in vivo for efficacy, stability, and the like. A variety of methods and animal models are available to assess the antimicrobial activity of selected candidate peptides and analogs or derivative thereof in vivo for their ability to ameliorate microbial infections. Within these assays, a peptide is useful as a therapeutic if inhibition of microbial growth compared to inhibition with the vehicle alone is statistically significant. This measurement: can be made directly from cultures isolated from body fluids or sites, or indirectly by assessing survival rates of infected animals.

For assessment of antibacterial activity of candidate peptide analogs and derivatives as compared to natural peptides, several animal models are available, such as acute infection models including those in which (a) normal mice receive a lethal dose of microorganisms, (b) neutropenic mice receive a lethal dose of microorganisms, or (c) rabbits receive an inoculum of microorganisms in the heart, and chronic infection models. The model selected will depend, in part, on the intended clinical indication of the peptide and/or analog or derivative thereof.

By way of example and not limitation, a normal mouse model is used to inoculate mice, intraperitoneally (i.p.) or intravenously (i.v.), with a lethal dose of bacteria. Typically, the dose is such that 90-100% of animals die within 2 days.

The choice of a microorganism strain for this assay depends, in part, upon the intended application of the antimicrobial cationic peptide or analog or derivative thereof, and in the accompanying examples, assays are carried out with three different *Staphylococcus* strains. Briefly, shortly before or after inoculation with the microorganism of choice (generally within 60 minutes), peptides or analogs or derivatives thereof in a suitable formulation buffer (as described herein) is injected. Multiple injections of peptides may be administered. Animals are observed for up to 8 days post-infection, and the survival of animals is recorded. Successful treatment either rescues animals from death or delays death to a statistically significant level, as compared with non-treatment, control animals. Antimicrobial cationic peptide analogs or derivatives thereof that show better efficacy than the natural peptides, such as indolicidins, are preferred.

Furthermore, for in vivo use, low immunogenicity is preferred. To measure immunogenicity, peptides are injected into normal animals, generally rabbits. At various times after single or multiple injections, serum is obtained and tested for antibody reactivity to the peptide or analog or derivative thereof. Antibodies to peptides or analogs or derivatives thereof may be identified by ELISA, immunoprecipitation assays, western blots, and other methods known in the art (see *Antibodies: A Laboratory Manual*, 1988). In a preferred embodiment the antibody of interest has undetectable, or minimally detectable, reactivity with the candidate peptides or analogs or derivative thereof. In addition, pharmacokinetics of the candidate peptides or analogs or derivatives in animals and histopathology of animals treated with the peptides may be determined.

Selection of antimicrobial cationic peptides and analogs or derivatives thereof as potential therapeutics is typically based on in vitro and in vivo assay results. In general, peptides that exhibit low immunogenicity, good, in vivo stability, and high efficacy at low dose levels are preferred candidate antimicrobial cationic peptides and analogs or derivatives thereof.

D. Cationic Peptide Formulations and Therapeutic Methods

As noted above, the present invention provides methods for treating and preventing infections by administering to a patient a therapeutically effective amount of an antimicrobial cationic peptide, preferably an indolicidin or analog or derivative thereof, as described herein. The antimicrobial cationic peptide is preferably part of a pharmaceutical composition when used in the methods of the present invention. The pharmaceutical composition will include at least one of a pharmaceutically acceptable vehicle, carrier, diluent, or excipient, in addition to one or more antimicrobial cationic peptide and, optionally, other components. Pharmaceutically acceptable excipients for therapeutic use are well known in the pharmaceutical art, and are described herein and, for example, in *Remington's Pharmaceutical Sciences*, Mack Publishing Co. (A. R. Gennaro, ed., 18$^{th}$ Edition, 1990) and in *CRC Handbook of Food, Drug, and Cosmetic Excipients*, CRC Press LLC (S. C. Smolinski, ed., 1992).

The therapeutic efficacy of an antimicrobial cationic peptide composition according to the present invention is based on a successful clinical outcome and does not require 100% elimination of the microorganisms involved in the infection. Achieving a level of antimicrobial activity at the site of infection that allows the host to survive, resolve the infection, or eradicate the causative agent is sufficient. When host defenses are maximally effective, such as in an otherwise healthy individual, only a minimal antimicrobial effect may suffice. Thus, reducing the organism load by even one log (a factor of 10) may permit the defenses of the host to control the infection. In addition, clinical therapeutic success may depend more on augmenting an early bactericidal effect rather than on a long-term effect because this allows time for activation of host defense mechanisms. This is especially true for life-threatening infections (e.g., meningitis) and other serious chronic infections (e.g., infective endocarditis).

The formulations of the present invention, having an amount of antimicrobial cationic peptide sufficient to treat or prevent an infection are, for example, particularly suitable for topical (e.g., creams, ointments, skin patches, eye drops, ear drops, shampoos) application or administration. Other typical routes of administration include, without limitation, oral, parenteral, sublingual, bladder wash-out, vaginal, rectal, enteric, suppository, nasal, and inhalation. The term parenteral, as used herein, includes subcutaneous, intravenous, intramuscular, intraarterial, intraabdominal, intraperitoneal, intraarticular, intraocular or retrobulbar, intraaural, intrathecal, intracavitary, intracelial, intraspinal, intrapulmonary or transpulmonary, intrasynovial, and intraurethral injection or infusion techniques. The pharmaceutical compositions of the present invention are formulated so as to allow the antimicrobial cationic peptide contained therein to be bioavailable upon administration of the composition to a subject. The level of peptide in serum and other tissues after administration can be monitored by various well-established techniques, such as bacterial, chromatographic or antibody based (e.g., ELISA) assays. Thus, in certain preferred embodiments, antimicrobial cationic peptides and analogs and derivatives thereof, as described herein, are formulated for topical application to a target site on a subject in need thereof, such as an animal or a human.

The compositions may be administered to a subject as a single dosage unit (e.g., a tablet, capsule, or gel), and the compositions may be administered as a plurality of dosage units (e.g., in aerosol form). For example, the antimicrobial cationic peptide formulations may be sterilized and packaged in single-use, plastic laminated pouches or plastic tubes of dimensions selected to provide for routine, measured dispensing. In one example, the container may have dimensions anticipated to dispense 0.5 ml of the antimicrobial cationic peptide composition (e.g., a gel form) to a limited area of the target surface on or in a subject to treat or prevent an infection. A typical target, for example, is in the immediate vicinity of the insertion site of an intravenous catheter, where the target surface usually has an area of about two square centimeters.

The antimicrobial cationic peptide composition may be provided in various forms, depending on the amount and number of different pharmaceutically acceptable excipients present. For example, the peptide composition may be in the form of a solid, a semi-solid, a liquid, a lotion, a cream, an ointment, a cement, a paste, a gel, or an aerosol. In a preferred embodiment, the peptide formulation is in the form of a gel. The pharmaceutically acceptable excipients suitable for use in the peptide formulation compositions as described herein may include, for example, a viscosity-increasing agent, a buffering agent, a solvent, a humectant, a preservative, a chelating agent, an oleaginous compound, an emollient, an antioxidant, an adjuvant, and the like. The function of each of these excipients is not mutually exclusive within the context of the present invention. For example, glycerin may be used as a solvent or as a humectant or as a viscosity-increasing agent. In one preferred embodiment, the formulation is a composition comprising an antimicrobial cationic peptide, a viscosity-increasing agent, and a solvent, which is useful, for example, at a target site for implanted or indwelling medical devices, as described herein.

The pharmaceutically acceptable excipients noted above are known in the art, yet the unexpected result of the present invention is that particular combinations of excipients afford the antimicrobial cationic peptides and analogs and derivatives thereof stability and prolonged, activity when stored at ambient temperature, even in the presence of an alcoholic solvent. Solvents useful in the present compositions are well known in the art and include without limitation water, glycerin, propylene glycol, isopropanol, ethanol, and methanol. In some embodiments, the solvent is glycerin or propylene glycol, preferably at a concentration ranging from about 0.1% to about 20%, more preferably about 5% to about 15%, and most preferably about 9% to 11%. In other embodiments, the solvent is water or ethanol, preferably at a concentration up to about 99%, more preferably up to about 90%, and most preferably up to about 85%. (Unless otherwise indicated, all percentages are on a w/w basis.) In yet other embodiments, the solvent is at least one of water, glycerin, propylene glycol, isopropanol, ethanol, and methanol, preferably is glycerin or propylene glycol and ethanol, more preferably is glycerin and ethanol, and most preferably is glycerin and water. One embodiment is a composition comprising an antimicrobial cationic peptide, a viscosity-increasing agent, a solvent, wherein the solvent comprises at least one of water at a concentration up to 99%, glycerin at a concentration up to 20%, propylene glycol at a concentration up to 20%, ethanol at a concentration up to 99%, and methanol at a concentration up to 99%.

Another useful pharmaceutical excipient of the present invention is a viscosity-increasing agent. In certain embodiments, the antimicrobial cationic peptide compositions of the present invention include a viscosity-increasing agent, including without limitation dextran, polyvinylpyrrolidone, methylcellulose, carboxymethyl cellulose, hydroxyethyl cellulose, hydroxypropyl methylcellulose, and hydroxypropyl cellulose, and combinations thereof. In preferred embodiments, the viscosity-increasing agent is hydroxyethyl cellulose or hydroxypropyl methylcellulose, preferably at a concentration ranging from about 0.5% to about 5%, more preferably from about 1% to about 3%, most preferably from about 1.3% to about 1.7%. In yet other preferred embodiments, the antimicrobial cationic peptide compositions have a first viscosity-increasing agent, such as hydroxyethyl cellulose, hydroxypropyl methylcellulose, dextran, or polyvinylpyrrolidone, and a second viscosity-increasing agent such as hydroxyethyl cellulose, hydroxypropyl methylcellulose, dextran, or polyvinylpyrrolidone. When used as either a first or second viscosity-increasing agent, dextran and polyvinylpyrrolidone are preferably used at a concentration ranging from about 0.1% to about 5% and more preferably from about 0.5% to about 1%. In one preferred embodiment, the first viscosity-increasing agent is hydroxyethyl cellulose at a concentration up to 3% and the second viscosity-increasing agent is hydroxypropyl methylcellulose at a concentration up to 3%. As is known in the art, the amount of viscosity-increasing agent may be increased to shift the form of the composition from a liquid to a gel to a semi-solid form. Thus, the amount of a viscosity-increasing agent used in a formulation may be varied depending on the intended use and location of administration of the peptide compositions provided herein.

In certain applications, it may be desirable to maintain the pH of the antimicrobial cationic peptide composition contemplated by the present invention within a physiologically acceptable range and within a range that optimizes the activity of the peptide or analog or derivative thereof. The antimicrobial cationic peptides of the present invention function best in a composition that is neutral or somewhat acidic, although the peptides will still have antimicrobial and anti-inflammatory activity in a composition that is slightly basic (i.e., pH 8). Accordingly, a composition comprising an antimicrobial cationic peptide, a viscosity-increasing agent, and a solvent, may further comprise a buffering agent. In certain embodiments, the buffering agent comprises a monocarboxylate or a dicarboxylate, and more specifically may be acetate, fumarate, lactate, malonate, succinate, or tartrate. Preferably, the antimicrobial, cationic peptide composition having the buffering agent has a pH ranging from, about 3 to about 8, and more preferably from about 3.5 to 7. In another preferred embodiment, the buffering agent is at a concentration ranging from about 1 mM to about, 200 mM, and more preferably from about 2 mM to about 20 mM, and most preferably about 4 mM to about 6 mM.

Other optional pharmaceutically acceptable excipients are those that may, for example, aid in the administration of the formulation (e.g., anti-irritant, polymer carrier, adjuvant) or aid in protecting the integrity of the components of the formulation (e.g., anti-oxidants and preservatives). Typically, a 1.0% antimicrobial cationic peptide composition may be stored at 2° C. to 8° C. In certain embodiments, the composition comprising an antimicrobial cationic peptide, a viscosity-increasing agent, and a solvent, may further comprise a humectant, preferably sorbitol and the like, or a preservative, preferably benzoic acid, benzyl alcohol, phenoxyethanol, methylparaben, propylparaben, and the like. In certain circumstances, the antimicrobial cationic peptide or analog or derivative thereof may itself function as a preservative of the final therapeutic composition. For example, a preservative is optional in the gel formulations described herein because the gels may be sterilized by autoclaving and, furthermore, show the surprising quality of releasing (i.e., making bioavailable) the antimicrobial cationic peptide at a more optimal rate than other formulations, such as a cream. In addition, particular embodiments may have in a single formulation a humectant, a preservative, and a buffering agent, or combinations thereof. Therefore, a preferred embodiment is a composition comprising an antimicrobial cationic peptide, a viscosity-increasing agent, a solvent, a humectant, and a buffering agent. Another preferred embodiment is a composition comprising an antimicrobial cationic peptide, a viscosity-increasing agent, a buffering agent; and a solvent. In yet another preferred embodiment, the composition comprises an antimicrobial cationic peptide, a buffering agent, and a solvent. Each of the above formulations may be used to treat or prevent infection or to reduce the microflora at a target site, such as a catheter insertion site on a subject (i.e., animal or human).

In yet other embodiments, the composition is in the form of an ointment comprising an antimicrobial cationic peptide (preferably in an amount sufficient to treat or prevent an infection) and an oleaginous compound. For example, oleaginous compound may be petrolatum. In one embodiment, the oleaginous compound is present at a concentration ranging from about 50% to about 100%, more preferably from about 70% to about 100%, even more preferably from about 80% to about 100%, and most preferably from about 95% to about 100%. In certain other embodiments, the ointment composition may further comprise at least one emollient. The emollients may be present at a concentration ranging from about 1% to about 40%, more preferably from about 5% to about 30%, and more preferably from about 5% to about 10%. In certain preferred embodiments, the emollient may be mineral oil, cetostearyl alcohol, glyceryl stearate, and a combination, thereof. In another aspect the, composition is in the form of a semi-solid emulsion (e.g., a cream) comprising an antimicrobial cationic peptide (preferably in an amount sufficient to treat or prevent an infection), a solvent, a buffering agent, at least one emollient, and at least one emulsifier. In a preferred embodiment, the semi-solid emulsion or cream further comprises at least one of a humectant (e.g., sorbitol and/or glycerin), an oleaginous compound (e.g., petrolatum), a viscosity increasing agent (e.g., dextran, polyvinylpyrrolidone, hydroxyethyl cellulose, and/or hydroxypropyl methylcellulose), an anti-oxidant (e.g., butylated hydroxytoluene and preferably at a concentration ranging from about 0.01% to about 0.1%), a preservative (e.g., benzoic acid, benzyl alcohol, phenoxyethanol, methylparaben, propylparaben, or a combination thereof), or a combination thereof. In certain preferred embodiments, the emollient may be one or more of stearyl alcohol, cetyl alcohol, and mineral oil. In certain other preferred embodiments, the emulsifiers may be one or more of stearyl alcohol, cetyl alcohol, polyoxyethylene 40 stearate, and glyceryl monostearate. In a preferred embodiment, the emulsifier is present at a concentration ranging, from about 1% to about 20%, more preferably from about 5% to about 10, and most preferably from about 1% to about 1.5%. As noted above, the function of each of these emulsifiers and emollients is not mutually exclusive in that an emollient may function as an emulsifier and the emulsifier may function as an emollient, depending on the particular formulation, as is known in the art and is described herein. In certain, preferred embodiments the solvent comprises water and the like, and the buffering agent comprises a monocarboxylate or dicarboxylate and the like, as described herein.

A subject suitable for treatment with an antimicrobial peptide formulation may be identified by well-established indicators of risk for developing a disease or well-established hallmarks of an existing disease. For example, indicators of an infection include fever, pus, microorganism positive cultures, inflammation, and the like. Infections that may be treated with antimicrobial cationic peptides provided by the present invention include without limitation those caused by or due to microorganisms, whether the infection is primary, secondary, opportunistic, or the like. Examples of microorganisms include bacteria (e.g., Gram-positive, Gram-negative), fungi, (e.g., yeast and molds), parasites (e.g., protozoans, nematodes, cestodes and trematodes), viruses (e.g., HIV, HSV, VSV), algae, and prions. Specific organisms in these classes are well known (see, for example, Davis et al., *Microbiology*, $3^{rd}$ edition, Harper & Row, 1980; and Stanier et al., *The Microbial World*, $5^{th}$ edition, Prentice Hall, 1986). Infections include, but are not limited to, toxic shock syndrome, diphtheria, cholera, typhus, meningitis, whooping cough, botulism, tetanus, pyogenic infections, sinusitis, pneumonia, gingivitis, mucitis, folliculitis, cellulitis, acne and acne vulgaris, impetigo, osteomyelitis, endocarditis, ulcers, burns, dysentery, urinary tract infections, gastroenteritis, anthrax, Lyme disease, syphilis, rubella, septicemia, and plague; as well as primary, secondary, and opportunistic infections associated with, for example, trauma, surgery, endotracheal intubation, tracheostomy, and cystic fibrosis.

A subject may have other clinical indications treatable or preventable with the compositions and methods of the present invention, which include without limitation those associated with implantable, indwelling, or similar medical devices, such as intravascular catheters (e.g., intravenous and intra-arterial), right heart flow-directed catheters, Hickman catheters, arteriovenous fistulae, catheters used in hemodialysis and peritoneal dialysis (e.g., silastic, central venous, Tenckhoff, and teflon catheters), vascular access ports, indwelling urinary catheters, urinary catheters, silicone catheters, ventricular catheters, synthetic vascular prostheses (e.g., aortofemoral and femoropopliteal), prosthetic heart valves, prosthetic joints, orthopedic implants, penile implants, shunts (e.g., Scribner, Torkildsen, central nervous system, portasystemic, ventricular, ventriculoperitoneal), intrauterine devices, tampons, contact lenses, dental implants, ureteral stents, pacemakers, implantable defibrillators, tubing, cannulas, probes, blood monitoring devices, needles, and the like. As used herein, "medical device" refers to any device for use in a subject, such as an animal or human.

By way of background, each year over 5 million central venous catheter (CVC) units are sold in the U.S., and it is estimated that 250,000 patients in the U.S. develop bloodstream infections related to CVCs each year. Infections associated with CVCs of various types account for 80-90% of all vascular catheter-related bloodstream infections (see Maki, D. G., *Infections Caused by Intravascular Devices Used for Infusion Therapy: Pathogenesis, Prevention, and Management*, In: Infections Associated with Indwelling Medical Devices, $2^{nd}$ ed., A. L. Bisno and F. A. Waldvogel (eds.), American Society for Microbiology, Washington, D.C., 1994). Prospective studies of short-term, non-cuffed, single or multilumen catheters inserted percutaneously into the subclavian or internal jugular vein have shown that rates of catheter-related septicemia range from 3-5%, with rates of 7-10% in some hospitals (Maki, 1994). Some of the organisms most commonly found to be causing these infections are *Staphylococcus aureus*, *Staphylococcus epidermidis*, *Enterococcus faecium*, *Escherichia coli*, *Enterobacter cloacae*, *Pseudomonas aeruginosa*, and *Candida albicans*, which account for 95% of reported infections. Therefore, a subject having a catheter or scheduled to have a catheter inserted would be particularly benefited by the antimicrobial cationic peptide compositions and methods of the present invention.

The primary strategies to prevent catheter-related infection are barrier precautions and the use of specialized i.v. teams. Vigorous hand washing and sterile gloves is highly recommended prior to catheter insertion. Other barrier precautions include, for example, a long-sleeved and sterile surgical gown, a mask, a cap, and a large sterile drape. This barrier methodology used in conjunction with specialized i.v. teams has been found to be effective at reducing rates of, for example, catheter-related infection. However, even when these precautions are taken, the longer any type of intravascular device remains in place, the higher the cumulative risk of device-related infection (particularly septicemia). For example, the length of time that non-cuffed CVCs are allowed to remain in place in Intensive Care Unit (ICU) patients is arbitrarily limited to 3 to 7 days in many medical centers. When the continued use of a short-term CVC for more than 4 days is considered essential in an ICU patient, the clinician has three options: (i) leave the catheter in place, accepting that the risk of infection will increase after 4 days; (ii) replace the old catheter over a guidewire at the original insertion site; or (iii) remove the catheter and place a new catheter at a new site, thereby gaining another 4 days of low risk. None of these options are optimal for the clinician or the patient.

An advantage of the present invention is that antisepsis of a target site for device insertion with an indolicidin or analog or derivative thereof, and formulated as described herein, may be achieved prior to device insertion and/or after device insertion and in combination with barrier precautions, which will reduce the risk of device-associated and other infections. Therefore, the compositions and methods of the present invention are specifically useful, for example, for cutaneous antisepsis to treat or prevent localized infection (e.g., after trauma, surgery, or other medical procedure), and to prevent medical device-related septicemia. Furthermore, as noted above, one benefit of using antimicrobial cationic peptides is the reduction of the risk for selecting antimicrobial-resistant microorganisms.

Uses of antimicrobial cationic peptide formulations of the present invention encompass numerous applications where a topical antimicrobial is useful in the treatment or prevention of infection. For example, burn wound infections remain the most common cause of morbidity and mortality in extensively burned patients. Moreover, infection is the predominant determinant of wound healing, incidence of complications, and outcome of burn patients. The main organisms responsible are *Pseudomonas aeruginosa, S. aureus, Streptococcus pyogenes*, and various gram-negative organisms. Frequent debridements and establishment of an epidermis or a surrogate, such as a graft, or a skin substitute, is essential for prevention of infection. Preferably, the antimicrobial peptide formulations, alone or in combination with antibiotics, is applied to burn wounds as a gel, ointment or cream, and/or administered systemically. Topical application may prevent systemic infection following superficial colonization or eradicate a superficial infection. The antimicrobial peptide composition is preferably administered as a 0.5 to 2% gel, cream, or ointment. Application to the skin could be done once a day or as often as dressings are changed. Systemic administration could be via intravenous, intramuscular or subcutaneous injections or infusions. Other routes of administration known in the art could also be used.

Another use for the present compositions and methods would be in the treatment of surgical wounds, especially those associated with foreign material (e.g., sutures). Nosocomial infections may occur in as many gas 71% of all surgical patients, and 40% of those are infections at the operative site. Despite efforts to prevent infection, it is estimated that between 500,000 and 920,000 surgical wound infections complicate the approximately 23 million surgical procedures performed annually in the United States. The infecting organisms are varied, but *Staphylococci* spp. are important organisms in these infections. Preferably, the antimicrobial peptide formulations, alone or in combination with antibiotics, is applied as an gel, ointment, cream or liquid to the wound site, or as a liquid in the wound prior to and during closure of the wound. Following closure, the antimicrobial peptide composition could also be applied at dressing changes. For surgical or trauma wounds that are infected, the antimicrobial peptide formulation described herein may be applied topically and/or systemically.

Yet another example, sterile gauze dressing has been the standard of care in catheterization for many years, but it has also been demonstrated that transparent polyurethane film dressings are superior because they permit continuous inspection of the catheterization site, they secure the device reliably, and they permit the patients to bathe and shower without saturating the dressing (Maki, 1994). Therefore, certain embodiments of this invention include antimicrobial cationic peptide compositions as described herein for use with sterile gauze or polyurethane film dressings.

Additionally, the compositions and methods of the present invention may be used to reduce the risk of device-related infections by directly coating a medical device prior to insertion at a target site or by impregnating the external surface of a medical device at the time of manufacture. In yet another aspect of this invention, the formulation includes an antimicrobial cationic peptide suitable for impregnating or coating a medical device. Thus, antimicrobial cationic peptides may be formulated as a coating or impregnation material suitable for treating the, surfaces of a medical device or its components. In certain embodiments, such coatings and impregnation materials may include covalent and/or non-covalent attachment of an antimicrobial cationic peptide and, analog or derivative thereof, to the interior and/or exterior surfaces of a medical device or its components. In other embodiments, such a coating and impregnation material may include the entrapment of an antimicrobial cationic peptide in a hydrogel layer or a bioerodable layer.

Other embodiments include use of antimicrobial cationic peptide coatings, gels, ointments, and impregnation compositions alone or in conjunction with filter units or catheter components used with, for example, a hemodialysis apparatus. In one embodiment, an arteriovenous shunt, such as a Scribner shunt, may be impregnated, coated, or adapted to a filter containing an antimicrobial cationic peptide. Other embodiments include the same coatings, gels, ointments, and impregnation compositions for use with an arteriovenous fistula. In still another embodiment, a coating may be suitable for use with a woven fiber vascular shunt.

Still other embodiments include use of antimicrobial cationic peptide formulations and methods with temporary access sites used to insert a medical device. In one preferred embodiment, antimicrobial cationic peptide formulations may be used during a femoral vein catheterization. Other preferred embodiments include use of the antimicrobial cationic peptide formulations with catheters, such as vascular dialysis catheters, pulmonary artery catheters, peritoneal dialysis catheters, umbilical catheters, and subclavian vein catheters.

By way of example and not limitation, both local and systemic infection may result from contaminated intravascular devices, such as a CVC, and the organisms typically responsible are coagulase-negative *Staphylococci* (CoNS), *Staphylococcus aureus, Enterococcus* spp, *E. coli* and *Candida* spp. Hence, the antimicrobial cationic peptide or analog or derivative thereof, preferably in the form of a gel or cream, may be applied to the catheter site prior to insertion of the catheter and then again at each dressing change. Preferably, the peptide is at a concentration ranging from about 0.85% to about 1.15%. Therefore, in a typical embodiment, a. composition contains an antimicrobial cationic peptide at a concentration ranging from about 0.01.% to about 10%; a viscosity-increasing agent selected of dextran, polyvinylpyrrolidone, hydroxyethyl cellulose, or hydroxypropyl methylcellulose; and a solvent of water, glycerin, propylene glycol, isopropanol, ethanol, or methanol; and at a pH ranging from about 3 to about 8.

In a preferred embodiment; the present invention is useful in a method for reducing microflora at a target site, comprising applying to the target site a composition comprising an antimicrobial cationic peptide, a viscosity-increasing agent, and a solvent. As used herein, a target site is any site on a subject where there is present, or there is a risk of, a primary or secondary or opportunistic infection (which infection is outside or inside the subject), and is any site where a formulation of the present invention may be administered or applied. In certain embodiments, the microflora being reduced at the target site may be prokaryotic, eukaryotic, or viral, and preferably is prokaryotic. In other embodiments, the method for reducing microflora at a target site, comprises applying to the target site a composition containing an antimicrobial cationic peptide, a viscosity-increasing agent, and a, solvent, and further comprises inserting a medical device at the target site before and/or after applying the composition. In another embodiment, the composition may further contain a buffering agent as described above and may have a pH ranging from about 3.5 to about 7. In addition, the composition may further contain a preservative, such as benzoic acid, benzyl alcohol, phenoxyethanol, methylparaben, propylparaben, and the like. Preferably, the peptide is an indolicidin or analog or derivative thereof, as described herein.

Another preferred embodiment is a composition comprising (a) an antimicrobial cationic peptide wherein the cationic peptide is a peptide of up to 35 amino acids comprising one of the following: 11B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN; (b) a viscosity-increasing agent wherein the viscosity-increasing agent is hydroxyethyl cellulose at a concentration of about 1.2% to about 1.8%; (c) a buffer wherein the buffer is lactate at a concentration ranging from about 4 mM to about 6 mM; (d) a solvent wherein the solvent comprises glycerin at a concentration ranging from about 9% to about 11% and water at a concentration ranging from about 85% to about 90%; and (e) a pH ranging from about 3.5 to about 7. In a more preferred embodiment, the cationic peptide is at a concentration ranging from about 0.8% to about 1.2%. Such compositions would be useful, for example, for topical antisepsis prior to insertion of a device (e.g., catheter) or prosthesis (e.g., synthetic arterial graft). In another embodiment, the composition may be applied to a target site to ameliorate inflammation, such as inflammation associated with an implanted or indwelling medical device.

The compositions and methods of the present invention would be therapeutically effective in treating or preventing acne, including severe acne vulgaris. Acne is due to colonization and infection of hair follicles and sebaceous cysts by *Propionibacterium acne*. Most cases remain mild and do not lead to scarring, although a subset of patients develop large inflammatory cysts and nodules, which may drain and result in significant scarring. The peptide formulations as described herein may be incorporated into soap, or applied topically as a cream, lotion, or gel to the affected areas. The peptide formulation may be applied either once a day or multiple times during the day, and the length of treatment may be for as long as the lesions are present or to prevent recurrent lesions. Alternatively, the peptide composition may be formulated to be administered orally or systemically to treat or prevent acne lesions. Preferably the peptide composition is formulated for topical administration or application. A preferred embodiment is a composition comprising an antimicrobial cationic peptide, a buffering agent, and a solvent; more preferably a composition, comprising (a) an antimicrobial cationic peptide wherein the cationic peptide is a peptide of up to 35 amino acids comprising one of the following: 11B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN; (b) a buffer wherein the buffer is lactate at a concentration ranging from about 4 mM to about 6 mM; (c) a solvent wherein the solvent comprises ethanol at a concentration ranging from about 45% to about 55% and water at a concentration ranging from about 44% to about 54%; and (d) a pH ranging from about 3.5 to about 7. In a more preferred embodiment, the cationic peptide is at a concentration ranging from about 0.8% to about 1.2%. In another preferred embodiment, the peptide composition may further comprise an acne medicament such as retinoid, vitamin D3, or corticosteroid, and analogs or derivatives thereof. Therefore, in certain preferred methods to reduce microflora, or to treat or prevent an infection, at a target site, the target site may be skin, and the skin may further comprise acne.

Another example of the therapeutic value of the compositions and methods of the present invention would be in the treatment of nosocomial infections. For example, infection by *S. aureus* may result in impetigenous lesions or infected wounds, and is associated with increased infection rates following cardiac surgery, hemodialysis, orthopedic surgery and neutropenia, both disease induced and iatrogenic. Nasal and extra-nasal carriage of *Staphylococci* spp. can result in hospital outbreaks of the same *Staphylococci* strain that is colonizing a patient's or a hospital worker's nasal passage or extra-nasal site. Much attention has been paid to the eradication of nasal colonization, but the results of treatment have been generally unsatisfactory. The use of topical antimicrobial substances, such as bacitracin, tetracycline, and chlorhexidine, results in the suppression of nasal colonization, as opposed to eradication.

Accordingly, a preferred embodiment is a composition comprising an antimicrobial cationic peptide, a viscosity-increasing agent, a solvent, and a preservative; more preferably a composition comprising (a) an antimicrobial cationic peptide wherein the cationic peptide is a peptide of up to 35 amino acids comprising one of the following: 11B7CN, 11B32CN, 11B36CN, 11E3CN, 11F4CN, 11F5CN, 11F12CN, 11F17CN, 11F50CN, 11F56CN, 11F63CN, 11F64CN, 11F66CN, 11F67CN, 11F68CN, 11F93CN, 11G27CN, 11J02CN, 11J02ACN, 11J30CN, 11J36CN, 11J58CN, 11J67CN, 11J68CN, Nt-acryloyl-11B7CN, Nt-glucosyl-11J36CN, or Nt-glucosyl-11J38CN; (b) a viscosity-increasing agent wherein the viscosity-increasing agent is hydroxyethyl cellulose at a concentration of about 1.2% to about 1.8%; (c) a solvent wherein the solvent comprises glycerin at a concentration ranging from about 9% to about 11% and water at a concentration ranging from about 85% to about 90%; (d) a preservative wherein the preservative is benzoic acid at a concentration ranging from about 20 mM to about 30 mM; and (e) a pH ranging from about 3.5 to about 4.7. In a more preferred embodiment, the cationic peptide is at a concentration ranging from about 0.8% to about 1.2%, or ranging from about 2.5% to about 3.5%.

These preferred compositions may be used in a method for reducing microflora, or for treating or preventing infection, at a target site by applying to the target site the antimicrobial cationic peptide formulations described herein. In another embodiment, the target site may be a mucosa, preferably the mucosa of the nasal passage or anterior naris.

Pharmaceutical compositions of the present invention are administered in a manner appropriate to the infection or disease to be treated. The amount and frequency of administration will be determined by factors such as the condition of the patient, the cause of the infection, and the severity of the infection. Appropriate dosages may be determined by clinical trials, but will generally range from about 0.1 to 50 mg/kg.

In addition, the compositions of the present invention may be used in the manner of common disinfectants or in any situation in which microorganisms are undesirable. For example, these peptides may be used as surface disinfectants, coatings, including covalent bonding, for medical devices, coatings for clothing, such as to inhibit growth of bacteria or repel mosquitoes, in filters for air purification, such as on an airplane, in water purification, constituents of shampoos and soaps, food preservatives, cosmetic preservatives, media preservatives, herbicide or insecticides, constituents of building materials, such as in silicone sealant, and in animal product processing, such as curing of animal hides.

The antimicrobial cationic peptides, particularly the labeled analogs and derivatives thereof, may be used in image analysis and diagnostic assays or for targeting sites in multicellular and single cellular organisms. As a targeting system, the analogues may be coupled with other peptides, proteins, nucleic acids, antibodies, chemical compounds. (e.g., fluorescent tags), and the like.

The following Examples are provided by way of illustration and not by way of limitation.

EXAMPLES

Example 1

Synthesis Purification and Characterization of Cationic Peptides and Analogues

Peptide synthesis is based on the standard solid-phase Fmoc protection strategy. The instrument employed is a 9050 Plus PepSynthesiser (PerSeptive BioSystems, Inc.). Polyethylene glycol polystyrene (PEG-PS) graft resins are employed as the solid phase derivatized with an Fmoc-protected amino acid linker for C-terminal amide synthesis. HATU (O-(7-azabenzotriazole-1-yl)-1,1,3,3-tetramethyluronium hexafluorophosphate) is used as the coupling reagent. During synthesis, coupling steps are continuously monitored to ensure that each amino acid is incorporated in high yield. The peptide is cleaved from the solid-phase resin using trifluoroacetic acid and appropriate scavengers and the crude peptide is purified using preparative reversed-phase chromatography. Typically the peptide is prepared as the trifluoroacetate salt, but other salts, such as acetate, chloride and sulfate, can also be prepared by salt exchange.

All peptides are analyzed by mass spectrometry to ensure that the product has the expected molecular mass. The product should have a single peak accounting for >95% of the total peak area when subjected to analytical reversed-phase high performance liquid chromatography (RP-HPLC), a separation method that depends on the hydrophobicity of the peptide. In addition, the peptide should show a single band accounting for >90% of the total band intensity when subjected to acid-urea gel electrophoresis, a separation method based on the charge to mass ration of the peptide.

Peptide content, the amount of the product that is peptide rather than retained water, salt or solvent, is measured by quantitative amino acid analysis, free amine derivatization or spectrophotometric quantitation. Amino acid analysis also provides information on the ratio of amino acids present in the peptide, which assists in confirming the authenticity of the peptide.

Peptide analogues and their names are listed below. In this list, and elsewhere, the amino acids are denoted by the one-letter amino acid code and lower case letters represent the D-form of the amino acid.

TABLE 1

Indolicidin analogs and derivatives thereof and Other Antimicrobial Cationic Peptides

| Apidaecin IA | (SEQ ID NO: 1) | G N N R P V Y I P Q P R P P H P R I |
|---|---|---|
| Deber A2KA2 | (SEQ ID NO: 2) | K K A A A K A A A A A K A A W A A K A A A K K K K |
| 10 | (SEQ ID NO: 3) | I L P W K W P W W P W R R |
| 10CN | (SEQ ID NO: 4) | I L P W K W P W W P W R R |
| 11 | (SEQ ID NO: 5) | I L K K W P W W P W R R K |
| 11CN | (SEQ ID NO: 6) | I L K K W P W W P W R R K |
| 11CNR | (SEQ ID NO: 7) | K R R W P W W P W K K L I |
| 11A1CN | (SEQ ID NO: 8) | I L K K F P F F P F R R K |
| 11A2CN | (SEQ ID NO: 9) | I L K K I P I I P I R R K |
| 11A3CN | (SEQ ID NO: 10) | I L K K Y P Y Y P Y R R K |
| 11A4CN | (SEQ ID NO: 11) | I L K K W P W P W R R K |
| 11A5CN | (SEQ ID NO: 12) | I L K K Y P W Y P W R R K |
| 11A6CN | (SEQ ID NO: 13) | I L K K F P W F P W R R K |
| 11A7CN | (SEQ ID NO: 14) | I L K K F P F W P W R R K |
| 11A8CN | (SEQ ID NO: 15) | I L R Y V Y Y V Y R R K |
| 11A9CN | (SEQ ID NO: 16) | I L R W P W W P W W P W R R K |
| 11A10CN | (SEQ ID NO: 17) | W W R W P W W P W R R K |
| 11B1CN | (SEQ ID NO: 18) | I L R R W P W W P W R R K |
| 11B2CN | (SEQ ID NO: 19) | I L R R W P W W P W R K |
| 11B3CN | (SEQ ID NO: 20) | I L K W P W W P W R R K |
| 11B4CN | (SEQ ID NO: 21) | I L K K W P W W P W R K |
| 11B5CN | (SEQ ID NO: 22) | I L K W P W W P W R K |

TABLE 1-continued

Indolicidin analogs and derivatives thereof and
Other Antimicrobial Cationic Peptides

| | | |
|---|---|---|
| 11B7CN | (SEQ ID NO: 23) | I L R W P W W P W R R K |
| 11B7CNR | (SEQ ID NO: 24) | K R R W P W W P W R L I |
| 11B8CN | (SEQ ID NO: 25) | I L W P W W P W R R K |
| 11B9CN | (SEQ ID NO: 26) | I L R R W P W W P W R R R |
| 11B10CN | (SEQ ID NO: 27) | I L K K W P W W P W K K K |
| 11B16CN | (SEQ ID NO: 28) | I L R W P W W P W R R K I M I L K K A G S |
| 11B17CN | (SEQ ID NO: 29) | I L R W P W W P W R R K M I L K K A G S |
| 11B18CN | (SEQ ID NO: 30) | I L R W P W W P W R R K D M I L K K A G S |
| 11B19CN | (SEQ ID NO: 31) | I L R W P W R R W P W R R K |
| 11B20CNAA | (SEQ ID NO: 32) | I L R W P W W P W R R K I L M R W P W W P W R R K M |
| 11B32CNR | (SEQ ID NO: 33) | K R K W P W W P W R L I |
| 11B36CN | (SEQ ID NO: 34) | I L K W V W W V W R R K |
| 11C3CN | (SEQ ID NO: 35) | I L K K W A W W P W R R K |
| 11C4CN | (SEQ ID NO: 36) | I L K K W P W W A W R R K |
| 11C5CN | (SEQ ID NO: 37) | W W K K W P W W P W R R K |
| 11D1CN | (SEQ ID NO: 38) | L K K W P W W P W R R K |
| 11D3CN | (SEQ ID NO: 39) | P W W P W R R K |
| 11D4CN | (SEQ ID NO: 40) | I L K K W P W W P W R R K M I L K K A G S |
| 11D5CN | (SEQ ID NO: 41) | I L K K W P W W P W R R M I L K K A G S |
| 11D6CN | (SEQ ID NO: 42) | I L K K W P W W P W R R I M I L K K A G S |
| 11D9M8 | (SEQ ID NO: 43) | W W P W R R K |
| 11D10M8 | (SEQ ID NO: 44) | I L K K W P W |
| 11D11H | (SEQ ID NO: 45) | I L K K W P W W P W R R K M |
| 11D12H | (SEQ ID NO: 46) | I L K K W P W W P W R R M |
| 11D13H | (SEQ ID NO: 47) | I L K K W P W W P W R R I M |
| 11D14CN | (SEQ ID NO: 48) | I L K K W W P W R K |
| 11D15CN | (SEQ ID NO: 49) | I L K K W P W W W R K |
| 11D18CN | (SEQ ID NO: 50) | W R I W K P K W R L P K W |
| 11D19CN | (SEQ ID NO: 51) | C L R W P W W P W R R K |
| 11E1CN | (SEQ ID NO: 52) | i L K K W P W W P W R R K |
| 11E2CN | (SEQ ID NO: 53) | I L K K W P W W P W R R k |
| 11E3CN | (SEQ ID NO: 54) | i L K K W P W W P W R R k |
| 11F1CN | (SEQ ID NO: 55) | I L K K V W W V W R R K |
| 11F2CN | (SEQ ID NO: 56) | I L K K W P W W V W R R K |
| 11F3CN | (SEQ ID NO: 57) | I L K K V W W P W R R K |
| 11F4CN | (SEQ ID NO: 58) | I L R W V W W V W R R K |
| 11F4CNR | (SEQ ID NO: 59) | K R R W V W W V W R L I |
| 11F5CN | (SEQ ID NO: 60) | I L R R W V W W V W R R K |

TABLE 1-continued

Indolicidin analogs and derivatives thereof and Other Antimicrobial Cationic Peptides

| | | |
|---|---|---|
| 11F6CN | (SEQ ID NO: 61) | I L R W W V W W V W R R K |
| 11F12CN | (SEQ ID NO: 62) | R L W V W W V W R R K |
| 11F17CN | (SEQ ID NO: 63) | R L W V W W V W R R |
| 11F50CN | (SEQ ID NO: 64) | R L G G G W V W W V W R R |
| 11F56CN | (SEQ ID NO: 65) | R L W W V V W W R R |
| 11F63CN | (SEQ ID NO: 66) | R L V V W W V V R R |
| 11F64CN | (SEQ ID NO: 67) | R L F V W W V F R R |
| 11F66CN | (SEQ ID NO: 68) | R L V V W V V W R R |
| 11F67CN | (SEQ ID NO: 69) | r L W V W W V W R R |
| 11F68CN | (SEQ ID NO: 70) | R L W V W W V W R r |
| 11F93CN | (SEQ ID NO: 71) | W V R L W W R R V W |
| 11G2CN | (SEQ ID NO: 72) | I K K W P W W P W R R K |
| 11G3CN | (SEQ ID NO: 73) | I L K K P W W P W R R K |
| 11G4CN | (SEQ ID NO: 74) | I L K K W W W P W R R K |
| 11G5CN | (SEQ ID NO: 75) | I L K K W P W W W R R K |
| 11G6CN | (SEQ ID NO: 76) | I L K K W P W W P R R K |
| 11G7CN | (SEQ ID NO: 77) | I L K K W P W W P W R R |
| 11G13CN | (SEQ ID NO: 78) | I L K K W P W W P W K |
| 11G14CN | (SEQ ID NO: 79) | I L K K W P W W P W R |
| 11G24CN | (SEQ ID NO: 80) | L W P W W P W R R K |
| 11G25CN | (SEQ ID NO: 81) | L R W W W P W R R K |
| 11G26CN | (SEQ ID NO: 82) | L R W P W W P W |
| 11G27CN | (SEQ ID NO: 83) | W P W W P W R R K |
| 11G28CN | (SEQ ID NO: 84) | R W W W P W R R K |
| 11H1CN | (SEQ ID NO: 85) | A L R W P W W P W R R K |
| 11H2CN | (SEQ ID NO: 86) | I A R W P W W P W R R K |
| 11H3CN | (SEQ ID NO: 87) | I L A W P W W P W R R K |
| 11H4CN | (SEQ ID NO: 88) | I L R A P W W P W R R K |
| 11H5CN | (SEQ ID NO: 89) | I L R W A W W P W R R K |
| 11H6CN | (SEQ ID NO: 90) | I L R W P A W P W R R K |
| 11H7CN | (SEQ ID NO: 91) | I L R W P W A P W R R K |
| 11H8CN | (SEQ ID NO: 92) | I L R W P W W A W R R K |
| 11H9CN | (SEQ ID NO: 93) | I L R W P W W P A R R K |
| 11H10CN | (SEQ ID NO: 94) | I L R W P W W P W A R K |
| 11H11CN | (SEQ ID NO: 95) | I L R W P W W P W R A K |
| 11H12CN | (SEQ ID NO: 96) | I L R W P W W P W R R A |
| 11J01CN | (SEQ ID NO: 97) | R R I W K P K W R L P K R |
| 11J02CN | (SEQ ID NO: 98) | W R W W K P K W R W P K W |
| 11J02ACN | (SEQ ID NO: 99) | W R W W K P K W R W P K W |

TABLE 1-continued

Indolicidin analogs and derivatives thereof and
Other Antimicrobial Cationic Peptides

| | | |
|---|---|---|
| 11J30CN | (SEQ ID NO: 100) | W R W W K V A W R W V K W |
| 11J36CN | (SEQ ID NO: 101) | W R W W K V W R W V K W |
| 11J38CN | (SEQ ID NO: 102) | W R W W K V V W R W V K W |
| 11J58CN | (SEQ ID NO: 103) | W (Orn) W W (Orn) V A W (Orn) W V (Orn) W |
| 11J67CN | (SEQ ID NO: 104) | W (Orn) W W (Orn) P (Orn) W (Orn) W P (Orn) W |
| 11J68CN | (SEQ ID NO: 105) | W (Dab) W W (Dab) P (Dab) W (Dab) W P (Dab) W |
| 21A1 | (SEQ ID NO: 106) | K K W W R R V L S G L K T A G P A I Q S V L N K |
| 21A2 | (SEQ ID NO: 107) | K K W W R R A L Q G L K T A G P A I Q S V L N K |
| 21A10 | (SEQ ID NO: 108) | K K W W R R V L K G L S S G P A L S N V |
| 22A1 | (SEQ ID NO: 109) | K K W W R R A L Q A L K N G L P A L I S |
| 26 | (SEQ ID NO: 110) | K W K S F I K K L T S A A K K V V T T A K P L I S S |
| 27 | (SEQ ID NO: 111) | K W K L F K K I G I G A V L K V L T T G L P A L I S |
| 28 | (SEQ ID NO: 112) | K W K L F K K I G I G A V L K V L T T G L P A L K L T K |
| 29 | (SEQ ID NO: 113) | K W K S F I K K L T T A V K K V L T T G L P A L I S |
| 29A2 | (SEQ ID NO: 114) | K W K S F I K N L T K V L K K V V T T A L P A L I S |
| 29A3 | (SEQ ID NO: 115) | K W K S F I K K L T S A A K K V L T T G L P A L I S |
| 29F1 | (SEQ ID NO: 116) | K W K L F I K K L T P A V K K V L L T G L P A L I S |
| 31 | (SEQ ID NO: 117) | G K P R P Y S P I P T S P R P I R Y |
| REWH53A5 | (SEQ ID NO: 118) | R L A R I V V I R V A R |
| Nt-Acryloyl-11B7CN | (SEQ ID NO: 119) | |
| Nt-glucosyl-11J36CN | (SEQ ID NO: 120) | |
| Nt-glucosyl-11J38CN | (SEQ ID NO: 121) | |

Nt prefix = N-terminal modification
CN suffix = amidated C-terminus
H suffix = homoserine at C-terminus
M suffix = M A P branched peptide
R suffix = retro-synthesized peptide
Orn = ornithine
Dab = diamino butyric acid
Upper case letter = L-enantiomer amino acid
Lower case letter = D-enantiomer amino acid

Example 2

Synthesis of Modified Peptides

Antimicrobial cationic peptides, such as indolicidin analogs or derivatives thereof, are modified to alter the physical properties of the original peptide, either by use of modified amino acids in synthesis or by post-synthetic modification. Such modifications include: acetylation at the N-terminus, Fmoc-derivatized N-terminus, polymethylation, peracetylation, and branched derivatives. Peptides modified using the procedures described herein are listed in Table 4.

α-N-terminal acetylation. Prior to cleaving the peptide from the resin and deprotecting it, the fully protected peptide is treated with N-acetylimidazole in DMF for 1 h at room temperature, which results in selective reaction at the α-N-terminus. The peptide is then deprotected/cleaved and purified as for an unmodified peptide.

Fmoc-derivatized α-N-terminus. If the final Fmoc deprotection step is not carried out, the α-N-terminus Fmoc group remains on the peptide. The peptide is then side-chain deprotected/cleaved and purified as for an unmodified peptide.

Polymethylation. The purified peptide in a methanol solution is treated with excess sodium bicarbonate, followed by excess methyl iodide. The reaction mixture is stirred overnight at room temperature, extracted with organic solvent, neutralized and purified as for an unmodified peptide. Using this procedure, a peptide is not fully methylated; methylation of 11CN yielded an average of 6 methyl groups. Thus, the modified peptide is a mixture of methylated products.

Caprolactam modification. A purified peptide in DMF solution is cooled to 0° C. on ice with stirring. Added to the peptide solution is 2-(1H-benzotriazole-1-yl)-1,1,3,3-teramethyluronium hexafluorophosphate and N-methylmorpholine; the reaction mixture is removed from the ice bath and stirred for 1 h, until the reaction mix rises to room temperature. Water is added and the resulting caprolactam peptide solution is purified by C8 RP-HPLC.

Peracetylation. A purified peptide in DMF solution is treated with N-acetylimidazole for 1 h at room temperature. The crude product is concentrated, dissolved in water, lyophilized, re-dissolved in water and purified as for an unmodified peptide. Complete acetylation of primary amine groups is observed.

Four/eight branch derivatives. The branched peptides are synthesized on a four- or eight-branched core bound to the resin. Synthesis and deprotection/cleavage proceed as for an unmodified peptide. These peptides are purified by dialysis against 4 M guanidine hydrochloride then water, and analyzed by mass spectrometry.

TABLE 2

Modified Indolicidin analogs and derivatives thereof

| Peptide modified | Peptide name | Modification |
|---|---|---|
| 10 | 10A | Acetylated α-N-terminus |
| 11 | 11A | Acetylated α-N-terminus |
| 11CN | 11ACN | Acetylated α-N-terminus |
| 11CN | 11CNW1 | Fmoc-derivatized N-terminus |
| 11CN | 11CNX1 | Polymethylated derivative |
| 11CN | 11CNY1 | Peracetylated derivative |
| 11 | 11M4 | Four branch derivative |
| 11 | 11M8 | Eight branch derivative |
| 11B1CN | 11B1CNW1 | Fmoc-derivatized N-terminus |
| 11B4CN | 11B4ACN | Acetylated N-terminus |
| 11B7CN | 11B7ACN | Acetylated N-terminus |
| 11B7CN | 11B7CNF12 | Formylated Lys[12] |
| 11B7 | 11B7Cap12 | Caprolactam Lys[12] |
| 11B9CN | 11B9ACN | Acetylated N-terminus |
| 11D9 | 11D9M8 | Eight branch derivative |
| 11D10 | 11D10M8 | Eight branch derivative |
| 11G6CN | 11G6ACN | Acetylated α-N-terminus |
| 11G7CN | 11G7ACN | Acetylated α-N-terminus |

Example 3

Antimicrobial Activity of Cationic Peptides

A cationic peptide may be tested for antimicrobial activity by using an in vitro assay as described below.

Agarose Dilution Assay

The agarose dilution assay measures antimicrobial activity of peptides and peptide analogues. The activity is expressed as the minimum inhibitory concentration (MIC) in μg/ml of the peptide.

In order to mimic in vivo conditions, calcium and magnesium supplemented Mueller Hinton broth is used in combination with a low EEO agarose as the bacterial growth medium. Agarose, rather than agar, is used as the charged groups in agar prevent peptide diffusion through the medium. The medium is autoclaved, then cooled to 50-55° C. in a water bath before aseptic addition of a peptide solution. The same volume of different concentrations of peptide solution is added to the cooled, molten agarose that is then poured into a petri plate to a depth of 3-4 mm and allowed to solidify.

The bacterial inoculum is adjusted to a 0.5 McFarland turbidity standard (PML Microbiological) and then diluted 1:10 before application on to, the agarose plate. The final inoculum applied to the agarose is approximately $10^4$ CFU in a 5-8 mm diameter spot. The agarose plates are incubated at 35-37° C. for 16 to 20 hours.

The MIC is recorded as the lowest concentration of peptide that completely inhibits growth of the organism as determined by visual inspection. Representative MIC values for various peptide analogues against bacteria and yeast are shown in Table 3.

TABLE 3

Activity of antimicrobial cationic peptides as determined by agarose dilution susceptibility testing

| | | Minimum Inhibitory Concentration (μg/ml) | | | | |
|---|---|---|---|---|---|---|
| Organism | Strain # | 11B7CN | 11B32CN | 11B36CN | 11E3CN | 11F4CN |
| A. calcoaceticus | ACA002 | 4 | 2 | 2 | 4 | 4 |
| E. cloacae | ECL007 | 128 | 128 | 64 | >128 | 64 |
| E. coli | ECO005 | 16 | 16 | 8 | 8 | 4 |
| K. pneumoniae | KPN001 | 128 | 32 | 8 | 32 | 4 |
| P. aeruginosa | PAE004 | 128 | 32 | 32 | 64 | 32 |
| S. maltophilia | SMA002 | 16 | 32 | 8 | 64 | 16 |
| S. marcescens | SMS003 | >128 | >128 | >128 | >128 | >128 |
| E. faecalis | EFS001 | 64 | 64 | 16 | 64 | 8 |
| S. aureus | SAU014 | 4 | 8 | 2 | 8 | 4 |
| S. epidermidis | SEP010 | 4 | 2 | 2 | 4 | 2 |
| S. mitis | SMT014 | 2 | 2 | 2 | 2 | 2 |
| S. pneumoniae | SPN002 | 4 | 8 | 4 | 4 | 8 |
| S. pyogenes | SPY001 | 1 | 2 | 2 | 1 | 2 |
| C. jeikeium | CJK005 | 0.5 | 0.5 | 1 | 0.5 | 2 |
| C. albicans | CAL002 | 16 | 16 | 8 | 32 | 32 |
| C. neoformans | CNE001 | 4 | 4 | 16 | 4 | 8 |

| | | Minimum Inhibitory Concentration (μg/ml) | | | | | |
|---|---|---|---|---|---|---|---|
| Organism | Strain # | 11F5CN | 11F12CN | 11F17CN | 11F50CN | 11F27CN | 11F56CN |
| A. calcoaceticus | ACA002 | 4 | 1 | 1 | 2 | 2 | 1 |
| E. cloacae | ECL007 | 128 | 32 | 16 | >128 | 128 | 32 |
| E. coli | ECO005 | 16 | 4 | 2 | 4 | 16 | 2 |
| K. pneumoniae | KPN001 | 64 | 8 | 2 | 16 | 32 | 2 |
| P. aeruginosa | PAE004 | 64 | 16 | 16 | >128 | 32 | 32 |
| S. maltophilia | SMA002 | 16 | 2 | 1 | 8 | 8 | 2 |
| S. marcescens | SMS003 | >128 | >128 | >128 | >128 | >128 | >128 |

TABLE 3-continued

Activity of antimicrobial cationic peptides as determined by agarose dilution susceptibility testing

| Organism | Strain # | | | | | | |
|---|---|---|---|---|---|---|---|
| E. faecalis | EFS001 | 16 | 2 | 2 | 16 | 16 | 2 |
| S. aureus | SAU014 | 8 | 2 | 1 | 2 | 8 | 1 |
| S. epidermidis | SEP010 | 2 | 1 | 1 | 1 | 2 | 1 |
| S. mitis | SMT014 | 2 | 1 | 1 | 1 | 4 | 1 |
| S. pneumoniae | SPN002 | 4 | 4 | 1 | 2 | 16 | 2 |
| S. pyogenes | SPY001 | 2 | 0.5 | 0.5 | 1 | 1 | 1 |
| C. jeikeium | CJK005 | 0.5 | 0.5 | 0.5 | 0.5 | 0.5 | 0.5 |
| C. albicans | CAL002 | 32 | 16 | 32 | 32 | 16 | 16 |
| C. neoformans | CNE001 | 8 | 4 | 4 | 16 | 4 | 8 |

| | | Minimum Inhibitory Concentration (μg/ml) | | | | |
|---|---|---|---|---|---|---|
| Organism | Strain # | 11F63CN | 11F64CN | 11F66CN | 11F67CN | 11F68CN |
| A. calcoaceticus | ACA002 | 2 | 2 | | 2 | 1 |
| E. cloacae | ECL007 | 16 | 16 | 8 | 32 | 32 |
| E. coli | ECO005 | 2 | 2 | 2 | 2 | 2 |
| K. pneumoniae | KPN001 | 4 | 2 | 2 | 2 | 2 |
| P. aeruginosa | PAE004 | 8 | 16 | 8 | 16 | 32 |
| S. maltophilia | SMA002 | 0.5 | 1 | 2 | 2 | 2 |
| S. marcescens | SMS003 | >128 | >128 | >128 | >128 | >128 |
| E. faecalis | EFS001 | 4 | 2 | 2 | 4 | 2 |
| S. aureus | SAU014 | 2 | 1 | 2 | 2 | 2 |
| S. epidermidis | SEP010 | 1 | 1 | 1 | 1 | 1 |
| S. mitis | SMT014 | 2 | 1 | 1 | 1 | 1 |
| S. pneumoniae | SPN002 | 4 | 2 | 2 | 2 | 2 |
| S. pyogenes | SPY001 | 1 | 1 | 1 | 1 | 1 |
| C. jeikeium | CJK005 | 1 | 0.5 | 1 | 0.5 | 0.5 |
| C. albicans | CAL002 | 16 | 16 | 16 | 32 | 32 |
| C. neoformans | CNE001 | 8 | 8 | 8 | 8 | 8 |

| | | Minimum Inhibitory Concentration (μg/ml) | | | | | |
|---|---|---|---|---|---|---|---|
| Organism | Strain # | 11F93CN | 11G27CN | 11J02CN | 11J02ACN | 11J30CN | 11J36CN |
| A. calcoaceticus | ACA002 | 4 | 16 | 2 | 2 | 2 | 2 |
| E. cloacae | ECL007 | 64 | >128 | 128 | >32 | 16 | 32 |
| E. coli | ECO005 | 4 | 64 | 16 | 16 | 8 | 8 |
| K. pneumoniae | KPN001 | 64 | >128 | 32 | 32 | 2 | 4 |
| P. aeruginosa | PAE004 | 64 | >128 | 32 | 64 | 32 | 64 |
| S. maltophilia | SMA002 | 8 | 64 | 4 | 8 | 4 | 2 |
| S. marcescens | SMS003 | >128 | >128 | >128 | >128 | >128 | >128 |
| E. faecalis | EFS001 | 16 | >128 | 64 | 64 | 32 | 16 |
| S. aureus | SAU014 | 2 | 16 | 2 | 8 | 2 | 1 |
| S. epidermidis | SEP010 | 2 | 8 | 2 | 2 | 2 | 1 |
| S. mitis | SMT014 | 2 | 8 | 2 | 2 | 1 | 1 |
| S. pneumoniae | SPN002 | 4 | 32 | 8 | 16 | 2 | 2 |
| S. pyogenes | SPY001 | 1 | 2 | 1 | 1 | 2 | 2 |
| C. jeikeium | CJK005 | 0.5 | 0.5 | 1 | 0.5 | 0.5 | 0.5 |
| C. albicans | CAL002 | 16 | 32 | 16 | 32 | 16 | 16 |
| C. neoformans | CNE001 | 8 | 16 | 4 | 16 | 4 | 4 |

| | | Minimum Inhibitory Concentration (μg/ml) | | | | |
|---|---|---|---|---|---|---|
| Organism | Strain # | 11J58CN | 11J67CN | 11J68CN | Nt-Glucosyl 11J36CN | Nt-Glucosyl 11J38CN |
| A. calcoaceticus | ACA002 | 1 | 1 | 0.5 | 1 | 2 |
| E. cloacae | ECL007 | 16 | 32 | 16 | 64 | 32 |
| E. coli | ECO005 | 2 | 8 | 8 | 4 | 16 |
| K. pneumoniae | KPN001 | 2 | 8 | 4 | 2 | 16 |
| P. aeruginosa | PAE004 | 16 | 8 | 4 | 16 | 128 |
| S. maltophilia | SMA002 | 2 | 1 | 4 | 4 | 16 |
| S. marcescens | SMS003 | >128 | >128 | 128 | >128 | >128 |
| E. faecalis | EFS001 | 32 | 64 | 16 | 16 | 16 |
| S. aureus | SAU014 | 1 | 2 | 1 | 2 | 2 |
| S. epidermidis | SEP010 | 1 | 1 | 1 | 2 | 2 |
| S. mitis | SMT014 | 1 | 0.5 | 0.5 | 1 | 2 |
| S. pneumoniae | SPN002 | 2 | 2 | 1 | 2 | 2 |
| S. pyogenes | SPY001 | 1 | <0.25 | 0.5 | 1 | 2 |
| C. jeikeium | CJK005 | 0.5 | <0.25 | <0.25 | 1 | 1 |
| C. albicans | CAL002 | 8 | 8 | 8 | 16 | 16 |
| C. neoformans | CNE001 | 2 | 2 | 1 | 4 | 4 |

Example 4

An In vitro Drug Release Method for Topical Formulations Using Low-Flow Cells An in vitro drug release method for topical formulations using a low-flow cells is used to examine the release of peptide from experimental formulations. The cell consists of an upper (donor) chamber physically separated from a lower (receptor) chamber by a permeable synthetic membrane (Tuffryn, Gelman). A total of 1 gram of a candidate formulation is placed in the donor chamber. The receptor fluid (distilled water, 37° C.) is pumped through the receptor chamber at 2 ml/h. Fractions were collected at various hourly intervals. Fractions were collected into vials, and the amount of receptor fluid collected in grams per fraction was recorded. The concentration of drug in the receptor fluid was determined by RP-HPLC on a Nova Pak C8 column. The column was eluted with a gradient from 20% to 40% acetonitrile over 10 min. using 0.1% aqueous trifluoroacetic acid, and 0.1% trifluoroacetic acid in acetonitrile, as solvents. The flow rate was 1 ml/min.

TABLE 4

Flow Cell Measurement of In Vitro Release

| Time Period (h) | Gel 73A | Gel 75A | Gel 76A |
|---|---|---|---|
| 0-1 | 974 | 789 | 992 |
| 2-3 | 760 | 707 | 777 |
| 4-6 | 722 | 503 | 671 |
| 7-9 | 590 | 414 | 435 |
| 10-12 | 541 | 499 | 455 |
| 13-15 | 396 | 400 | 376 |
| 16-18 | 303 | 300 | 249 |
| 19-21 | 312 | 204 | 220 |
| 22-24 | 309 | 276 | 372 |

The membrane is a 0.45 µm Tuffryn, (hydrophilic polysulfone) membrane, the data represents µg of antimicrobial cationic peptide released during the time interval. The detection limit is 1 µg released per hour. The data in Table 4 shows that gel formulations show excellent, initial release that should-facilitate rapid antibiotic action upon application. The gel formulations also, demonstrate good sustained release of drug. During the 22-24 hour collection, the average concentration of drug released into the receptor fluid ranged from 93 µgrams/ml (Gel 75A) to 124 µgrams/ml (Gel 76A)—well above the MIC values for sensitive organisms.

TABLE 5

Compositions of Gels and Creams Tested

| Ingredient | Gel 73A | Gel 75A | Gel 76A |
|---|---|---|---|
| Antimicrobial Cationic Peptide | 1.0 | 1.0 | 1.0 |
| Hydroxyethyl Cellulose, NF | 1.5 | 1.5 | 1.5 |
| Glycerin, USP | 10.0 | 10.0 | 10.0 |
| Polyvinylpyrrolidone 90 | — | 1.0 | — |
| 0.1M Lactate buffer, pH 4 | 5.0* | 5.0 | 5.0 |
| Dextran (40,000), USP | — | — | 1.0 |
| Purified Water, USP | 100.0 | 100.0 | 100.0 |

All entries are grams added/100 grams of gel.

Example 5

Antimicrobial Activity of an Aqueous 1.0% Cationic Peptide Gel

The objective of this study was to assess the antimicrobial activity of 1.0% antimicrobial cationic peptide gel against *Pseudomonas aeruginosa* PA004; *Candida albicans* CA002; *Staphylococcus aureus* SA016; and *Staphylococcus epidermidis* SE010. Briefly, a 2 g portion of 11B7CN 1.0% Gel was aseptically transferred into each of sixteen 50 mL tubes. Four tubes, one for each bacterium, were labeled as day 0, day 1, day 3, and day 7. As a control, a 2 g portion of vehicle (gel without antimicrobial cationic peptide 1.0%) was aseptically transferred into each of sixteen 50 mL tubes and labeled as described above.

An inoculum of $1 \times 10^8$ CFU/ml for each of the above listed organisms was prepared. For each of the series of tubes designated for each specific organism, 10 µl of undiluted inoculum was added to the gel in each of the tubes giving a final bacterial concentration of $5 \times 10^5$ CFU/g of gel. The contents of the tube were mixed using the handle of a sterile swab.

The tubes labeled days 1, 3, and 7 were held at ambient temperatures and sampled at the indicated time point. The day 0 tubes were sampled immediately. At the time of sampling, 1 g of gel from the test or control tube was removed and streaked on appropriate culture media. Growth of the appropriate organism was observed after 24 and 48 hours of incubation. The remaining 1 g of test or control gel was added to saline and serially diluted. Aliquots of 0.1 ml were plated in duplicate on appropriate medium and counted after 24 and 48 hours of incubation.

The results of this study are described in Table 6. The 1.0% antimicrobial cationic peptide gel has activity against *P. aeruginosa* PA004; *C. albicans* CA002; *S. aureus* SA016; and *S. epidermidis* SE010. Each of the organisms was killed immediately upon exposure to the 1.0% antimicrobial cationic peptide gel.

TABLE 6

Summary of Colony Counts for Four Organisms with 1.0% Antimicrobial Cationic Peptide Gel Organism Tested: *C. albicans* (CA002) MIC = 64 ug/ml

| | Formulation without 11B7CN (48 hour counts) | | | | 11B7CN in Formulation (48 hour counts) | | | |
|---|---|---|---|---|---|---|---|---|
| Dilution | Time 0 Avg. Colony Count (CFU/g) | 1 Day Avg. Colony Count (CFU/g) | 3 Days Avg. Colony Count (CFU/g) | 7 Days Avg. Colony Count (CFU/g) | Time 0 Avg. Colony Count (CFU/g) | 1 Day Avg. Colony Count (CFU/g) | 3 Days Avg. Colony Count (CFU/g) | 7 Days Avg. Colony Count (CFU/g) |
| Neat | TNTC | TNTC | TNTC | TNTC | 0 | 0 | 0 | 0 |
| $10^{-1}$ | $1.5 \times 10^5$ | TNTC | TNTC | TNTC | 0 | 0 | 0 | 0 |
| $10^{-2}$ | $1.2 \times 10^5$ | $3.3 \times 10^5$ | $5.0 \times 10^5$ | $4.1 \times 10^5$ | 0 | 0 | 0 | 0 |

TABLE 6-continued

Summary of Colony Counts for Four Organisms with 1.0% Antimicrobial Cationic Peptide Gel

| Dilution | | | | | | | | |
|---|---|---|---|---|---|---|---|---|
| $10^{-3}$ | $2.5 \times 10^5$ | $3.5 \times 10^5$ | $5.0 \times 10^5$ | $7.5 \times 10^5$ | 0 | 0 | 0 | 0 |
| $10^{-4}$ | 0 | 0 | $3.0 \times 10^6$ | $1.5 \times 10^6$ | 0 | 0 | 0 | 0 |

Organism Tested: *P. aeruginosa* (PA004) MIC = 128 ug/ml

| | Formulation without Antimicrobial cationic peptide (48 h counts) | | | | Antimicrobial cationic peptide in Formulation (48 h counts) | | | |
|---|---|---|---|---|---|---|---|---|
| Dilution | Time 0 Avg. Colony Count (CFU/g) | 1 Day Avg. Colony Count (CFU/g) | 3 Days Avg. Colony Count (CFU/g) | 7 Days Avg. Colony Count (CFU/g) | Time 0 Avg. Colony Count (CFU/g) | 1 Day Avg. Colony Count (CFU/g) | 3 Days Avg. Colony Count (CFU/g) | 7 Days Avg. Colony Count (CFU/g) |
| Neat | $5.3 \times 10^3$ | $1.0 \times 10^2$ | 0 | 0 | 0 | 0 | 0 | 0 |
| $10^{-1}$ | $5.5 \times 10^3$ | 0 | 0 | 0 | 0 | 0 | 0 | 0 |
| $10^{-2}$ | 0 | 0 | 0 | 0 | 0 | 0 | 0 | 0 |
| $10^{-3}$ | 0 | 0 | 0 | 0 | 0 | 0 | 0 | 0 |

Organism Tested: *S. aureus* (SA016) MIC = 2 ug/ml

| | Formulation without Antimicrobial cationic peptide (48 h counts) | | | | Antimicrobial cationic peptide in Formulation (48 h counts) | | | |
|---|---|---|---|---|---|---|---|---|
| Dilution | Time 0 Avg. Colony Count (CFU/g) | 1 Day Avg. Colony Count (CFU/g) | 3 Days Avg. Colony Count (CFU/g) | 7 Days$^a$ Avg. Colony Count (CFU/g) | Time 0 Avg. Colony Count (CFU/g) | 1 Day Avg. Colony Count (CFU/g) | 3 Days Avg. Colony Count (CFU/g) | 7 Days Avg. Colony Count (CFU/g) |
| Neat | TNTC | TNTC | TNTC | TNTC | 0 | 0 | 0 | 0 |
| $10^{-1}$ | TNTC | TNTC | TNTC | TNTC | 0 | 0 | 0 | 0 |
| $10^{-2}$ | $4.8 \times 10^5$ | $8.4 \times 10^5$ | $7.6 \times 10^5$ | $4.2 \times 10^5$ | 0 | 0 | 0 | 0 |
| $10^{-3}$ | $3.5 \times 10^5$ | $1.0 \times 10^6$ | $1.3 \times 10^6$ | $6.0 \times 10^5$ | 0 | 0 | 0 | 0 |

Organism Tested: *S. epidermidis* (SE010) MIC = 4 ug/ml

| | Formulation without Antimicrobial cationic peptide (48 h counts) | | | | Antimicrobial cationic peptide in Formulation (48 h counts) | | | |
|---|---|---|---|---|---|---|---|---|
| Dilution | Time 0 Avg. Colony Count (CFU/g) | 1 Day Avg. Colony Count (CFU/g) | 3 Days Avg. Colony Count (CFU/g) | 7 Days$^a$ Avg. Colony Count (CFU/g) | Time 0 Avg. Colony Count (CFU/g) | 1 Day Avg. Colony Count (CFU/g) | 3 Days Avg. Colony Count (CFU/g) | 7 Days Avg. Colony Count (CFU/g) |
| Neat | TNTC | TNTC | $2.1 \times 10^4$ | $1.2 \times 10^3$ | 0 | 0 | 0 | 0 |
| $10^{-1}$ | $8.2 \times 10^4$ | $5.5 \times 10^4$ | $1.9 \times 10^4$ | $3.0 \times 10^3$ | 0 | 0 | 0 | 0 |
| $10^{-2}$ | $1.3 \times 10^5$ | $4.5 \times 10^4$ | $1.0 \times 10^4$ | 0 | 0 | 0 | 0 | 0 |
| $10^{-3}$ | $1.0 \times 10^5$ | $5.0 \times 10^4$ | 0 | 0 | 0 | 0 | 0 | 0 |

All of the above U.S. patents, US. patent application publications, U.S. patent applications, foreign patents, foreign patent applications and non-patent publications referred to in this specification and/or listed in the Application Data Sheet, are incorporated herein by reference, in their entirety.

It will be appreciated that, although specific embodiments of the invention have been described herein for purposes of illustration, various modifications may be made without departing from the spirit and scope of the invention. Accordingly, the invention is not limited except, as by the appended claims.

The invention claimed is:

1. A method for preventing an infection caused by a prokaryotic or eukaryotic organism at a target site, comprising applying to the target site a composition comprising an antimicrobial cationic peptide at a concentration ranging from about 0.01% to about 10% (w/w), a viscosity-increasing agent, and a solvent, wherein the cationic peptide is a peptide of up to 35 amino acids comprising 11B7CN (SEQ ID NO: 23), the viscosity-increasing agent is hydroxyethyl cellulose at a concentration of about 0.5% to about 5% (w/w), and the solvent is water and glycerin, wherein the solvent comprises glycerin at a concentration up to about 20% (w/w), and wherein the composition is a gel.

2. The method of claim 1, wherein the infection is caused by a prokaryotic organism, wherein, the prokaryotic organism is a bacterium.

3. The method of claim 1, wherein the infection at a target site is associated with a medical device at the target site.

4. The method of claim 3, comprising applying the composition prior to or after inserting a medical device at the target.

5. The method of claim 3, wherein applying the composition to the target site comprises applying the composition to the medical device prior to inserting the device at the target site.

6. The method according to claim 4, wherein the medical device comprises a catheter.

7. The method according to claim 1, wherein the target site is a wound.

8. The method according to claim 1, wherein the cationic peptide 11B7CN (SEQ ID NO: 23) is at a concentration ranging from about 2.0% to about 4.0% (w/w).

9. The method according to claim 1, wherein the glycerin in the solvent is at a concentration ranging from 9% to 11% (w/w).

10. The method according to claim 1, wherein the hydroxyethyl cellulose is at a concentration ranging from 1% to 3% (w/w).

11. The method according to claim 1, wherein the composition further comprises benzoic acid.

12. The method according to claim 1, wherein the composition further comprises a monocarboxylate or dicarboxylate buffering agent at a concentration in a range of about 1 mM to about 200 mM and wherein the composition has a pH ranging from about 3.5 to about 7.

13. The method according to claim 12, wherein the buffering agent is selected from the group consisting of acetate, fumarate, lactate, malonate, succinate, and tartrate.

14. A method for preventing an infection caused by a prokaryotic or eukaryotic organism at a target site, comprising applying to the target site a composition comprising art antimicrobial cationic peptide at a concentration ranging from about 0.01% to about 10% (w/w), a viscosity-increasing agent at a concentration of about 0.5% to about 5% (w/w), a solvent, and a monocarboxylate buffering agent at a concentration ranging from about 1 mM to about 200 mM, wherein the cationic peptide is a peptide of up to 35 amino acids comprising 11B7CN (SEQ ID NO: 23), wherein the viscosity-increasing agent is hydroxyethyl cellulose, the solvent is water and glycerin, and the monocarboxylate buffering agent is lactate, wherein the solvent comprises glycerin at a concentration up to about 20% (w/w), and wherein the composition is a gel and has a pH ranging from about 3 to about 8.

15. The method according to claim 14, wherein the composition further comprises a preservative.

16. The method according to claim 15, wherein the preservative comprises benzoic acid, benzyl alcohol, phenoxyethanol, methylparaben, propylparaben, or a combination thereof.

17. The method according to claim 14, wherein the composition further comprises a second viscosity-increasing agent selected from dextran, polyvinylpyrrolidone, and hydroxypropyl methylcellulose.

18. The method according to claim 17, wherein the second viscosity-increasing agent is dextran at a concentration ranging from about 0.1% to about 5% (w/w).

19. A method for preventing an infection caused by a prokaryotic or eukaryotie organism at a target site, comprising applying to the target site a composition comprising an antimicrobial cationic peptide at a concentration ranging from about 0.01% to about 10% (w/w), a viscosity-increasing agent at a concentration of about 0.5% to about 5% (w/w), a solvent selected from one or more of water, glycerin, propylene glycol, isopropanol, ethanol, and methanol, and a monocarboxylate buffering agent at a concentration ranging from about 1 mM to about 200 mM, wherein the cationic peptide is a peptide of up to 35 amino acids comprising 11B7CN (SEQ ID NO: 23), wherein the viscosity-increasing agent is hydroxyethyl cellulose, and wherein the composition is a gel and has a pH ranging from about 3 to about 8.

20. The method according to claim 19, wherein the concentration of the antimicrobial cationic peptide is in a range from about 1% to about 3% (w/w).

21. The method according to claim 19, wherein the concentration of the antimicrobial cationic peptide is in a range from about 2.5% to about 3.5% (w/w).

22. The method according to claim 20, wherein the solvent is water and glycerin, wherein the solvent comprises glycerin at a concentration up to about 20% (w/w).

23. The method according to claim 22, wherein the concentration of glycerin in the solvent is in a range of about 9% to about 11% (w/w).

24. The method according to claim 22, wherein the concentration of hydroxyethyl cellulose is in a range of about 1% to about 3% (w/w).

25. The method according to claim 19, wherein the composition has a pH ranging from about 3.5 to about 7.

26. A method for preventing acne at a target site comprising applying to the target site a composition comprising an antimicrobial cationic peptide at a concentration ranging from about 0.01% to about 10% (w/w), a viscosity-increasing agent, and a solvent, wherein the cationic peptide is a peptide of up to 35 amino acids comprising 11B7CN (SEQ ID NO: 23), the viscosity-increasing agent is hydroxyethyl cellulose at a concentration of about 0.5% to about 5% (w/w) and the solvent is water and glycerin, wherein the solvent comprises glycerin at a concentration up to about 20% (w/w), and wherein the composition is a gel.

27. The method of claim 26, wherein the acne is acne vulgaris.

28. The method of claim 26, wherein the acne is caused by *Propionibacterium acne*.

29. A method for treating or preventing inflammation at a target site, comprising applying to the target site a composition comprising an antimicrobial cationic peptide at a concentration ranging from about 0.01% to about 10% (w/w), a viscosity-increasing agent, and a solvent, wherein the cationic peptide is a peptide of up to 35 amino acids comprising 11B7CN (SEQ ID NO: 23), the viscosity-increasing agent is hydroxyethyl cellulose at a concentration of about 0.5% to about 5% (w/w), and the solvent is water and glycerin, wherein the solvent comprises glycerin at a concentration up to about 20% (w/w), and wherein the composition is a gel.

30. The method according to claim 26, wherein the concentration of the antimicrobial cationic peptide is in a range from about 1% to about 3% (w/w).

31. The method according to claim 26, wherein the concentration of the antimicrobial cationic peptide is in a range from about 2.5% to about 3.5% (w/w).

32. The method according to claim 26, wherein the concentration of glycerin in the solvent is in a range of about 9% to about 11% (w/w).

33. The method according to claim 26, wherein the concentration of hydroxyethyl cellulose is in a range of about 1% to about 3% (w/w).

34. The method according to claim 26, wherein the composition has a pH ranging from about 3.5 to about 7.

35. The method according to claim 29, wherein the concentration of the antimicrobial cationic peptide is in a range from about 1% to about 3% (w/w).

36. The method according to claim 29, wherein the concentration of the antimicrobial cationic peptide is in a range from about 2.5% to about 3.5% (w/w).

37. The method according to claim 29, wherein the concentration of glycerin in the solvent is in a range of about 9% to about 11% (w/w).

38. The method according to claim 29, wherein the concentration of hydroxyethyl cellulose is in a range of about 1% to about 3% (w/w).

39. The method according to claim 29, wherein the composition has a pH ranging from about 3.5 to about 7.

* * * * *